United States Patent
Dillard et al.

(10) Patent No.: US 6,645,976 B1
(45) Date of Patent: Nov. 11, 2003

(54) INDOLIZINE SPLA$_2$ INHIBITORS

(75) Inventors: Robert D. Dillard, Zionsville, IN (US); Sanji Hagishita, Nara (JP); Mitsuaki Ohtani, Nara (JP)

(73) Assignees: Eli Lilly and Company, Indianapolis, IN (US); Shiongi and Company, Ltd., Osaka (JP)

(*) Notice: Subject to any disclaimer, the term of this patent is extended or adjusted under 35 U.S.C. 154(b) by 0 days.

(21) Appl. No.: 08/765,566
(22) PCT Filed: Jul. 20, 1995
(86) PCT No.: PCT/US95/09381
§ 371 (c)(1),
(2), (4) Date: Apr. 28, 1997
(87) PCT Pub. No.: WO96/03383
PCT Pub. Date: Feb. 8, 1996

Related U.S. Application Data

(63) Continuation-in-part of application No. 08/278,445, filed on Jul. 21, 1994.

(51) Int. Cl.$^7$ .................... C07D 221/04; A61K 31/435; A61K 31/675
(52) U.S. Cl. ........................ 514/299; 546/112
(58) Field of Search .................... 546/112; 514/299

(56) References Cited

U.S. PATENT DOCUMENTS 3,717,644 A    2/1973   Walter ................. 260/293.53

FOREIGN PATENT DOCUMENTS

GB    1174124    12/1969

OTHER PUBLICATIONS

Munford, R.S., "Spesis and Septic Shock" in: Isselbacher, K.J., et al. *Harrison's Principles of Internal Medicine*, (McGraw–Hill, New York, 1994), pp. 511–515.

Robertson, R.P., "Eicosanoids and Human Disease" in: Isselbacher, K.J., et al. *Harrison's Principles of Internal Medicine*, (McGraw–Hill, New York, 1994), pp. 431–435.

Ingram, R.H., Jr., "Adult Respiratory Distress Syndrome" in: Isselbacher, K.J., et al. *Harrison's Principles of Internal Medicine*, (McGraw–Hill, New York, 1994), pp. 1240–1243.

Greenberger, N.J., et al., "Acute and Chronic Pancreatitis" in: Isselbacher, K.J., et al. *Harrison's Principles of Internal Medicine*, (McGraw–Hill, New York, 1994), pp. 1520–1530.

*Primary Examiner*—Bruck Kifle
(74) *Attorney, Agent, or Firm*—Roger S. Benjamin

(57) ABSTRACT

A class of novel indolizine-1-functional compounds and indolizine-3-functional compounds is disclosed together with the use of such indolizine compounds for inhibiting sPLA$_2$ mediated release of fatty acids for treatment of conditions such as septic shock. The compounds are indolizine-1-acetamides, indolizine-1-acetic acid hydrazides, indolizine-1-glyoxylamides, indolizine-3-acetamides, indolizine-3-acetic acid hydraxides, and indolizine-3-glyoxylasides.

32 Claims, No Drawings

INDOLIZINE SPLA₂ INHIBITORS

CROSS REFERENCE TO RELATED APPLICATIONS

This application is a continuation-in-part of U.S. patent application Ser. No. 08/278,445 filed Jul. 21, 1994.

FIELD OF THE INVENTION

This invention relates to novel indolizine compounds useful for inhibiting sPLA₂ mediated release of fatty acids for conditions such as septic shock.

BACKGROUND OF THE INVENTION

The structure and physical properties of human non-pancreatic secretory phospholipase $A_2$ (hereinafter called, "sPLA₂") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; The Journal of Biological Chemistry, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; The Journal of Biological Chemistry, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid). Such compounds would be of value in general treatment of conditions induced and/or maintained by overproduction of sPLA₂; such as septic shock, adult respiratory distress syndrome, pancreatitis, trauma, bronchial asthma, allergic rhinitis, rheumatoid arthritis, gout, glomerulonephritis, and etc.

U.S. Pat. No. 2,825,734 describes the preparation of 3-(2-amino-1-hydroxyethyl) indoles using 3-indole glyoxylamide intermediates such as 1-phenethyl-2-ethyl-6-carboxy-N-propyl-3-indoleglyoxylamide (see, Example 30).

U.S. Pat. No. 2,890,233 describes several amide derivatives of 3-indoleacetic acids.

U.S. Pat. Nos. 3,196,162; 3,242,162; 3,242,163; and 3,242,193 (see, Col. 3, lines 55–60, Example 56) describe indolyl aliphatic acids together with their related esters and amides.

U.S. Pat. No. 3,271,416 describes indolyl aliphatic acids as sun screening agents and intermediates. These acids may be —NH₂ substituted.

U.S. Pat. No. 3,351,630 describes alpha-substituted 3-indolyl acetic acid compounds and their preparation inclusive of glyoxylamide intermediates.

U.S. Pat. No. 3,449,363 describes trifluoromethylindoles having glyoxylamide groups at the 3 position of the indole nucleus. These compounds are stated to be analgesics.

U.S. Pat. No. 5,132,319 describes certain 1-(hydroxylaminoalkyl)indoles derivatives as inhibitors of leukotriene biosynthesis.

The article, "Structure-activity relationships leading to WAY-121,520, a tris aryl-type, indomethacin-based, phospholipase A₂ (PLA₂)/leukotriene biosynthesis inhibitor", by A Kreft, et. al., Agents and Actions, Special Conference Issue Vol. 39 (1993),pp. C33–C35, ISSN 0065–4299, published by Birkhauser Verlag, Basel Switzerland; (Proceedings of the Sixth International Conference of the Inflammation Research Association, Sep. 20–24, 1992, at White Haven, Pa./USA, Guest Editors, D. W. Morgan and A. K. Welton) describes the inhibition of phospholipase A2 by indomethacin analogs. Indole compounds having benzyl and acidic substituents are described.

The article, (Short communication) entitled, "Indolizine derivatives with biological activity VI 1-(2-aminoethyl)-3-benzyl-7-methoxy-2-methylindolizine, benanserin structural analogue" by G M Cingolani, F. Claudi, M. Massi, and F. Venturi, Eur. J. Med. Chem. (1990) 25, pp. 709–712 publ. by Elsevier, Paris describes selected indolizines and their activity on smooth muscle.

The article, "Indolizine Analogues of Indomethacin" by C. Casagrande, A. Invernizzi, R. Ferrini, and G. Miragoli, Il Farmaco—Ed. Sc.—Vol. 26—fasc. 12, pp. 1059–1073, describes pharmacological tests with selected indomethacin analogues.

European Patent Application No. 0 519 353 (Application No. 92109968.5) describes indolizin derivatives which have pharmacological activities such as inhibitory activity on testosteron reductase.

European Patent Application No. 0 620 214 (Application No. 94302646.8 describes hydrazide derivatives of indoles having sPLA₂ inhibitory activity.

It is desirable to develop new compounds and treatments for sPLA₂ induced diseases.

SUMMARY OF THE INVENTION

This invention is a novel use of indolizine compounds having the nucleus and substituent numbering positions shown in the following formula:

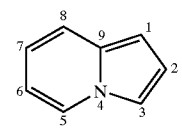

Moreover, this invention is a class of novel indolizine compounds having two general configurations shown in structural formulae "A" and "B" below:

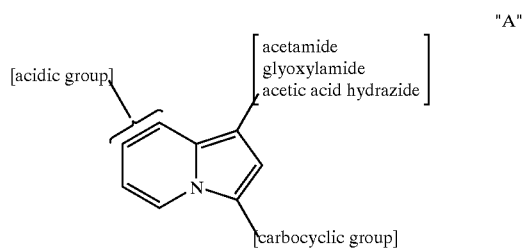

In configuration "A" an acetamide, acetic acid hydrazide or glyoxylamide moiety is present at the 1 position, a large ($C_7$–$C_{30}$) organic (e.g., carbocyclic) group is present at the 3 position and an acidic group is at the 7 or 8 positions.

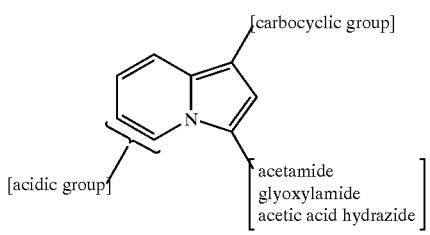

In configuration "B" an acetamide, acetic aced hydrazide or glyoxylamide moiety is present at the 3 position, a large ($C_7$–$C_{30}$) organic (e.g., carbocyclic) group is present at the 1 position and an acidic group is at the 5 or 6 positions.

These indolizine-1-functional and indolizine-3-functional compounds of the invention are effective in inhibiting human sPLA$_2$ mediated release of fatty acids.

This invention is also a pharmaceutical composition containing indolizine-1-functional or indolizine-3-functional compounds selected from the group consisting of the novel indolizine compounds represented by the general formulae "A" and "B" and mixtures thereof.

This invention is also a method of preventing and treating septic shock, adult respiratory distress syndrome, pancreatitis, trauma, bronchial asthma, allergic rhinitis, rheumatoid arthritis, gout, glomerulonephritis, and related diseases by contact with a therapeutically effective amount of indolizine-1-functional and indolizine-3-functional compounds selected from the group consisting of the novel indolizine compounds represented by the general formulae "A" or "B" and mixtures thereof.

DETAILED DESCRIPTION OF THE INVENTION

Definitions

The indolizine acetamides, acetic acid hydrazides (hereinafter called, "hydrazides"), and glyoxylamides of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number ange of carbon atoms, and typified by groups such as vinyl, propenyl, crotonyl, isopentenyl, and various butenyl isomers.

The term, "hydrocarbyl" means an organic group containing only carbon and hydrogen.

The term, "carbocyclic radical" refers to radicals derived from a saturated or unsaturated, substituted or unsubstituted 5 to 14 membered organic nucleus whose ring forming atoms (other than hydrogen) are solely carbon atoms.

The term, "halo" means fluoro, chloro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridinyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

Typical carbocyclic radicals are cycloalkyl, cycloalkenyl, phenyl, naphthyl, norbornanyl, bicycloheptadienyl, toluyl, xylenyl, indenyli stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

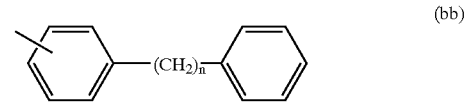

(bb)

where n is a number from 1 to 8.

The term, "non-interfering substituent", refers to radicals which do not prevent or significantly reduce the inhibition of sPLA$_2$ mediated release of fatty acids. Non-interfering substituents are suitable for substitution at positions 5, 6, 7 and/or 8 on the indolizine nucleus (as hereinafter depicted in Formula IA) and for radical(s) suitable for substitution on the heterocyclic radical and carbocyclic radical as defined above. Illustrative non-interfering radicals are $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

The term, "acidic group" means an organic group which when attached to an indolizine nucleus, through suitable linking atoms (hereinafter defined as the "acid linker"), acts as a proton donor capable of hydrogen bonding. Illustrative of an acidic group are the following:

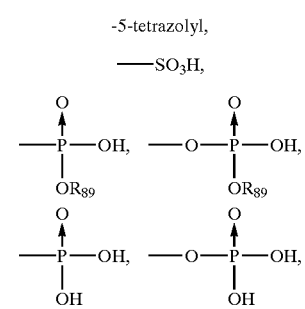

-continued

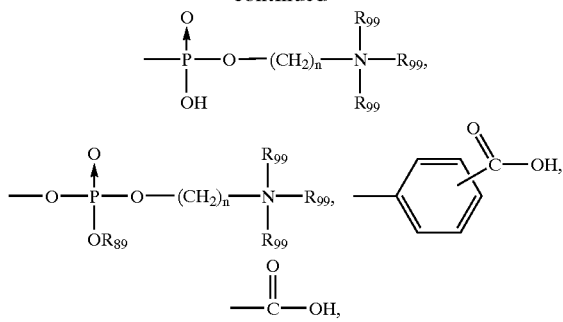

where n is 1 to 8, $R_{89}$ is a metal or $C_1$–$C_{10}$ alkyl, and $R_{99}$ is hydrogen or $C_1$–$C_{10}$ alkyl.

The words, "acid linker" refer to a divalent linking group symbolized as, —($L_a$)—, which has the function of joining the indolizine nucleus to an acidic group in the general relationship:

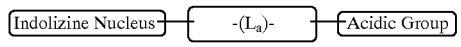

The words, "acid linker length", refer to the number of atoms (excluding hydrogen) in the shortest chain of the linking group —($L_a$)— that connects the indolizine nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

(a)
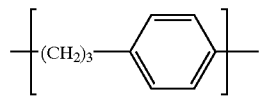

(b)
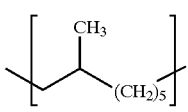

(c)
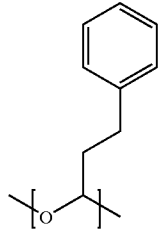

wherein, groups (a), (b), and (c) have acid linker lengths of 5, 7, and 2, respectively.

The term, "amine", includes primary, secondary and tertiary amines.

Type "A" Configuration Indolizine Comoounds of the Invention:

There are three types of Configuration type "A" indolizine compounds of the invention as represented by structural formulae (IA), (IIA), and (IIIA) below:

The indolizine-1-acetamides are represented by the formula (IA), below:

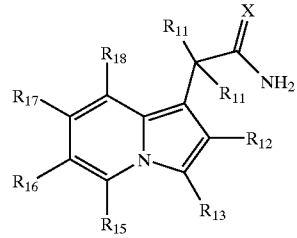
(IA)

where X is oxygen or sulfur and each $R_{11}$ is independently hydrogen, $C_1$–$C_3$ alkyl, or halo and all other groups are as hereinafter defined.

The indolizine-1-hydrazides are represented by the formula (IIA), as set out below:

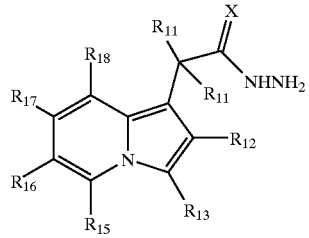
(IIA)

where X is oxygen or sulfur and each $R_{11}$ is independently hydrogen, $C_1$–$C_3$ alkyl, or halo and all other groups are as hereinafter defined.

The indolizine-1-glyoxylamides are represented by formula (IIIA), as set out below:

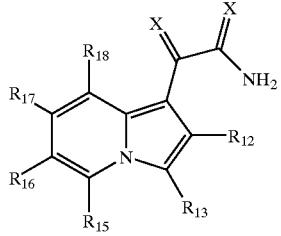
(IIIA)

where X is independently oxygen or sulfur and all other groups are as hereinafter defined.

For formulae (IA), (IIA), and (IIIA) above the remaining groups are defined as follows:

$R_{13}$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen; (that is, the $R_{12}$ radical may contain hydrogen atoms, but the remaining atoms comprising the total of 1 to 3 are non-hydrogen);

$R_{17}$ and $R_{18}$ are independently selected from hydrogen, a non-interfering substituent, or the group, —($L_a$)—(acidic group); wherein —($L_a$)—, is an acid linker having an acid linker length of 1 to 10; provided, that at least one of $R_{17}$ and $R_{18}$ must be the combined group, —($L_a$)—(acidic group); and $R_{15}$ and $R_{16}$ are each independently selected from hydrogen, non-interfering substituent, carbocyclic radical, carbocyclic radical substituted with non-interfering substituents, heterocyclic radical, and heterocyclic radical substituted with non-interfering substituents.

Preferred Subarouis of Type "A" Indolizine Compounds of the Invention:

A preferred subclass of compounds of formulae (IA), (IIA), and (IIIA) are those wherein all X are oxygen.

Another preferred subclass of compounds of formulae (IA), (IIA), and (IIIA) are those wherein $R_{12}$ is selected from the group; halo, cyclopropyl, methyl, ethyl, propyl, —O-methyl, and —S-methyl.

Another preferred subclass of compounds of formulae (IA), (IIA) and (IIIA) are those wherein for $R_{13}$, —(L)— is selected from the group consisting of:

—C≡C—, —CH=CH—, —CH$_2$—,
—(CH$_2$)$_2$—, —(CH$_2$)$_s$—S—, —(CH$_2$)$_s$—O—, and

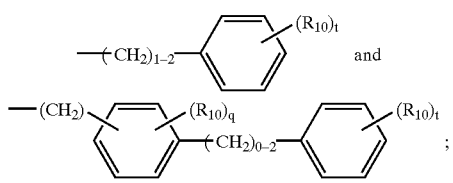

where s is 0 or 1.

Another preferred subclass of compounds of formulae (IA), (IIA), and (IIIA) are those wherein for $R_{13}$, group $R_{80}$ is carbocyclic and is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

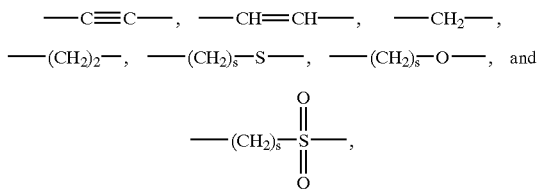

where n is a number from 1 to 8. Particularly preferred are compounds wherein $R_{13}$ is selected from the group consisting of

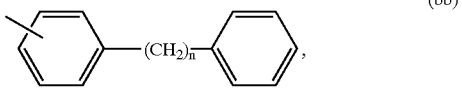

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5.

Another preferred subclass of compounds of formulae (IA), (IIA), and (IIIA) are those wherein $R_{18}$ is a substituent having an acid linker with an acid linker length of 2 or 3.

Another preferred subclass of compounds of formulae (IA), (IIA), and (IIIA) are those wherein $R_{18}$ comprises an acidic group and the acid linker for the acidic group has an acid linker length of 2 or 3 and the acid linker group, —($L_a$)—, for $R_{18}$ is selected from the group represented by the formula;

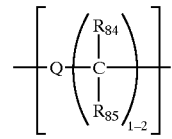

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo. Most preferred are compounds where the acid linker, —($L_a$)—, for $R_{18}$ is selected from the specific groups;

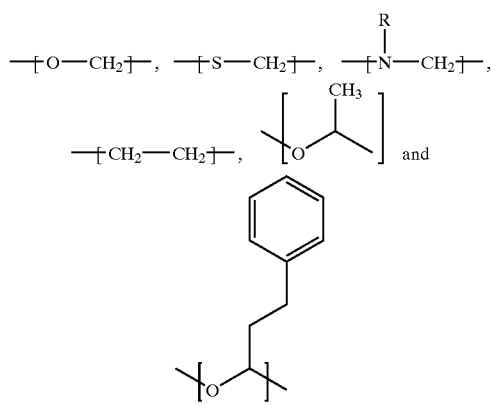

where R is H or $C_1$–$C_4$ alkyl.

Another preferred subclass of compounds of formulae (IA), (IIA), and (IIIA) are those wherein $R_{17}$ comprises an acidic group and the acid linker of the $R_{17}$ acidic group has an acid linker with an acid linker length of 3 to 10 atoms and the acid linker group, —($L_a$)—, for $R_{17}$ is selected from;

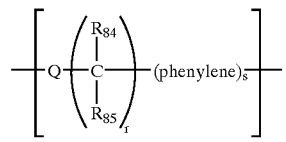

where r is a number from 1 to 7, s is 0 or 1, and Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo. Most preferred are compounds where the acid linker, —($L_a$)—, for $R_{17}$ is selected from the specific groups:

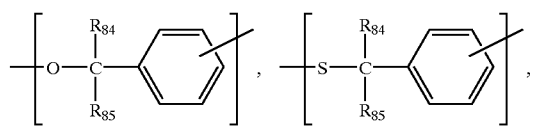

-continued

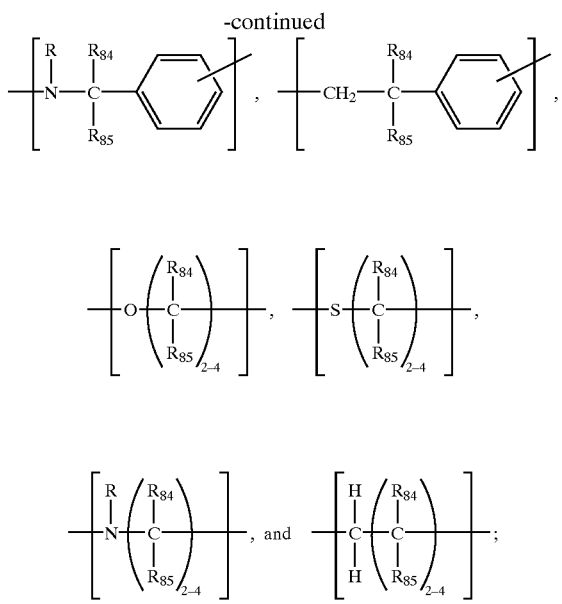

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

Another preferred subclass of compounds of formulae (IA), (IIA), (IIIA) are those wherein the acidic group (or salt, and prodrug derivatives thereof) on $R_{17}$ and/or $R_{18}$ is selected from the following:

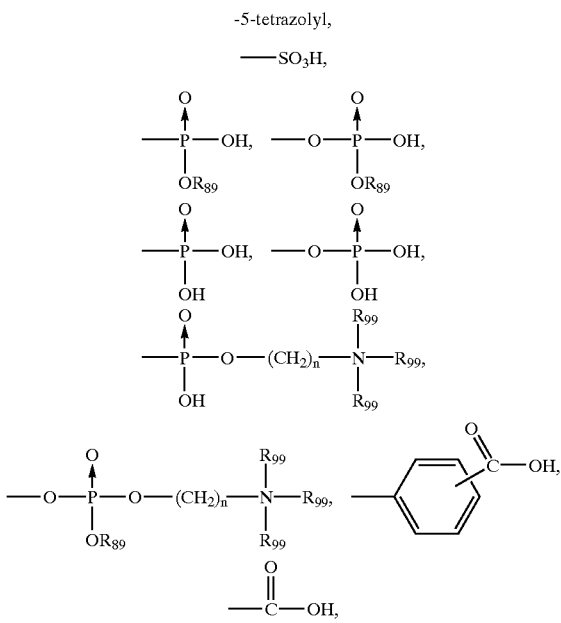

-5-tetrazolyl,
—SO$_3$H, where n is 1 to 8, $R_{89}$ is a metal or $C_1$–$C_{10}$ alkyl, and $R_{99}$ is hydrogen or $C_1$–$C_{10}$ alkyl. Particularly preferred are compounds wherein the acidic group of $R_{17}$ and $R_{18}$ is selected from;

—CO$_2$H,    —SO$_3$H,    —P(O)(OH)$_2$, or salt, and prodrug (e.g., ester) derivatives thereof. The carboxyl group is the most preferred acidic group. It is highly preferred that only one of $R_{17}$ or $R_{18}$ contain an acidic group.

Another preferred subclass of compounds of formula (IA), (IIA), and (IIIA) are those wherein $R_{15}$ and $R_{16}$ are each independently selected from hydrogen and non-interfering substituents, with the non-interfering substituents being selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

B) Type "B" Indolizine-3-acetamide Compounds of the Invention Having the General Formula (IB):

A) The Indolizine-3-acetamides are Represented by the Formula (IB), below:

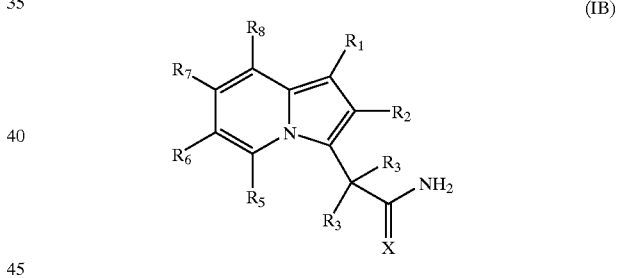

(IB)

where each $R_3$ is independently hydrogen, $C_1$–$C_3$ alkyl, or halo; X is selected from oxygen or sulfur; and all other groups are as hereinafter defined.

B) The Indolizine-3-hydrazides are Represented by the Formula (IIB), below:

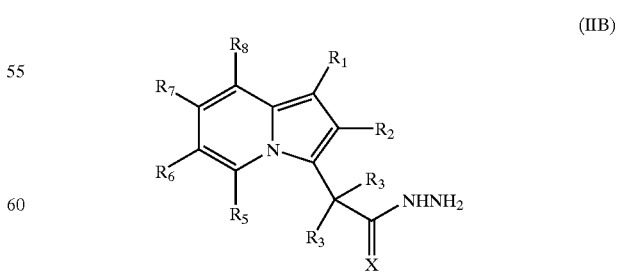

(IIB)

each $R_3$ is independently, hydrogen, $C_1$–$C_3$ alkyl, or halo; X is selected from oxygen or sulfur; and all other groups are as hereinafter defined.

C) The Indolizine-1-glyoxylamides are Represented by the Formula (IIIB), below:

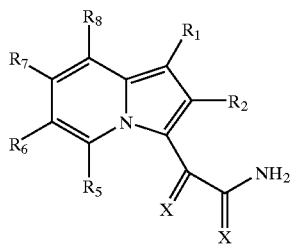
(IIIB)

where each X is independently selected from oxygen and sulfur, and all other groups are as hereinafter defined.

For formulae (IB), (IIB), and (IIIB) above the remaining groups are defined as follows:

$R_1$ is selected from groups (a), (b) and (c) where;
  (a) is $C_7$–$C_{20}$ alkyl, $C_7$–$C_{20}$ alkenyl, $C_7$–$C_{20}$ alkynyl, carbocyclic radicals, or heterocyclic radicals, or
  (b) is a member of (a) substituted with one or more independently selected non-interfering substituents; or
  (c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen; (that is, the $R_2$ radical may contain hydrogen atoms, but the remaining atoms comprising the total of 1 to 3 are non-hydrogen);

$R_5$ and $R_6$ are independently selected from hydrogen, a non-interfering substituent, or the group, —($L_a$)—(acidic group); wherein —($L_a$)—, is an acid linker having an acid linker length of 1 to 10; provided, that at least one of $R_5$ and $R_6$ must be the group, —($L_a$)—(acidic group);

$R_7$ and $R_8$ are each independently selected from hydrogen, non-interfering substituent, carbocyclic radicals, carbocyclic radicals substituted with non-interfering substituents, heterocyclic radicals, and heterocyclic radicals substituted with non-interfering substituents.

Preferred Subgroups of Type "B" Indolizine Compunds of the Invention:

A preferred subclass of compounds of formulae (IB), (IIB), and (IIIB) are those wherein all X are oxygen.

Another preferred subclass of compounds of formulae (IB), (IIB), and (IIIB) are those wherein $R_2$ is selected from the group; halo, cyclopropyl, methyl, ethyl, propyl, —O-methyl, and —S-methyl.

Another preferred subclass of compounds of formulae (IB), (IIB) and (IIIB) are those wherein for $R_1$ —(L)— is selected from the group consisting of:

—C≡C—, —CH=CH—, —CH$_2$—,

—(CH$_2$)$_2$—, —(CH$_2$)$_s$—S—, —(CH$_2$)$_s$—O—, and

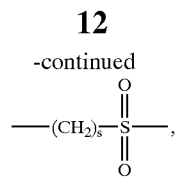

where s is 0 or 1.

Another preferred subclass of compounds of formulae (IB), (IIB), and (IIIB) are those wherein for $R_1$, group $R_{80}$ is carbocyclic and is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

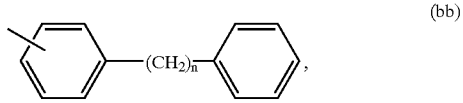
(bb)

where n is a number from 1 to 8. Particularly preferred are compounds wherein $R_1$ is selected from the group consisting of

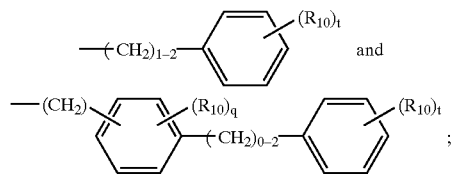

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5.

Another preferred subclass of compounds of formulae (IB), (IIB), and (IIIB) are those wherein $R_5$ is a substituent having an acid linker with an acid linker length of 2 or 3.

Another preferred subclass of compounds of formulae (IB), (IIB), and (IIIB) are those wherein $R_5$ comprises an acidic groupand the acid linker for the acidic group has an acid linker length of 2 or 3 and the acid linker group, —($L_a$)—, for $R_5$ is selected from the group represented by the formula;

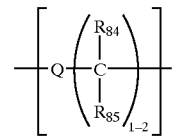

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo. Most preferred are compounds where the acid linker, —($L_a$)—, for $R_5$ is selected from the specific groups;

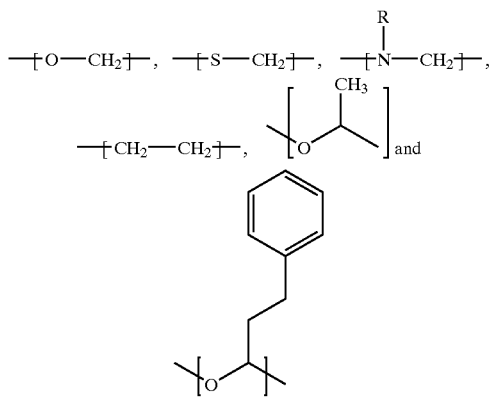

where R is H or $C_1$–$C_4$ alkyl.

Another preferred subclass of compounds of formulae (IB), (IIB), and (IIIB) are those wherein $R_6$ comprises an acidic group and the acid linker of the $R_6$ acidic group has an acid linker with an acid linker length of 3 to 10 atoms and the acid linker group, —$(L_a)$—, for $R_6$ is selected from;

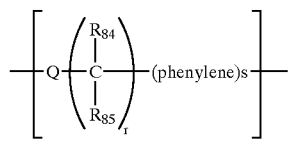

where r is a number from 1 to 7, s is 0 or 1, and Q is selected from the group —$(CH_2)$—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo. Most preferred are compounds where the acid linker, —$(L_a)$—, for $R_6$ is selected from the specific groups;

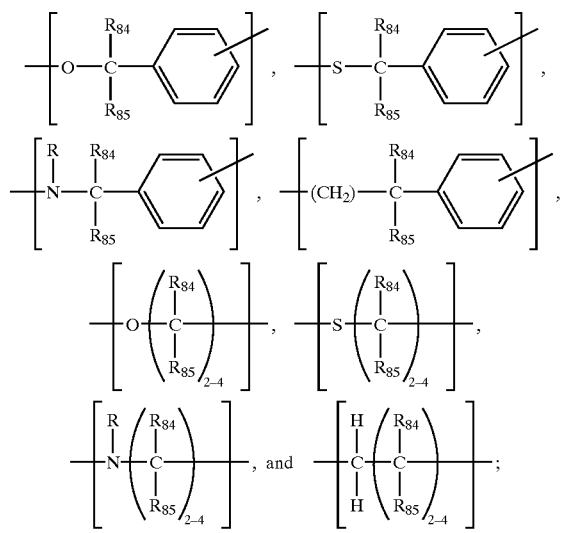

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

Another preferred subclass of compounds of formulae (IB), (IIB), (IIIB) are those wherein the acidic group (or salt, and prodrug derivatives thereof) on $R_5$ and/or $R_6$ is selected from the following:

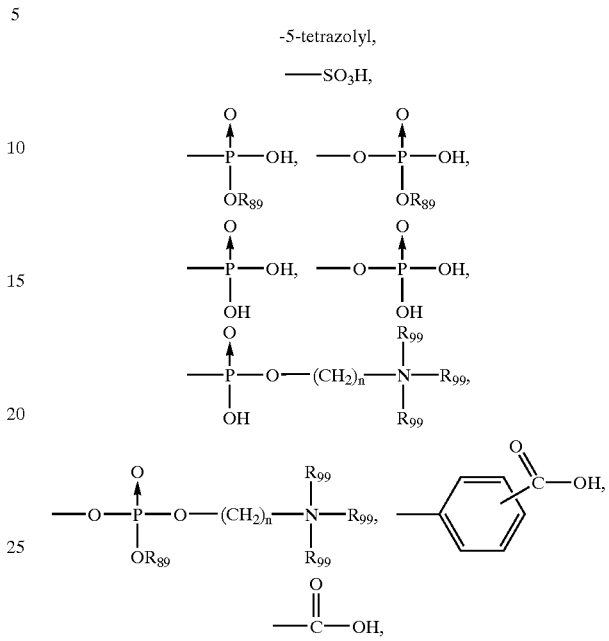

where n is 1 to 8, $R_{89}$ is a metal or $C_1$–$C_{10}$ alkyl, and $R_{99}$ is hydrogen or $C_1$–$C_{10}$ alkyl. Particularly preferred are compounds wherein the acidic group of $R_5$ and/or $R_6$ is selected from;

or salt, and prodrug (e.g., ester) derivatives thereof. The carboxyl group is the most preferred of all acidic groups. It is also highly preferred that only one of $R_5$ or $R_6$ contain an acidic group.

Another preferred subclass of compounds of formulae (IB), (IIB) and (IIIB) are those wherein $R_7$ and $R_8$ are each independently selected from hydrogen and non-interfering substituents, with the non-interfering substituents being selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

Specific preferred compounds (inclusive of all pharmaceutically acceptable salts, solvates and prodrug derivatives thereof) of the invention are represented by formulae shown in Sections (AA), (AB), and (AC) below:

(AA) Indolizine Compounds of Type "A" Having Acetamide Functionality
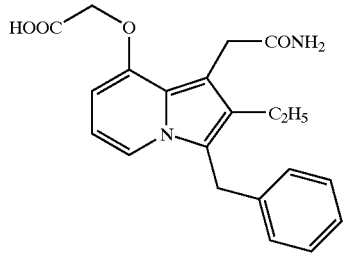
(22v)
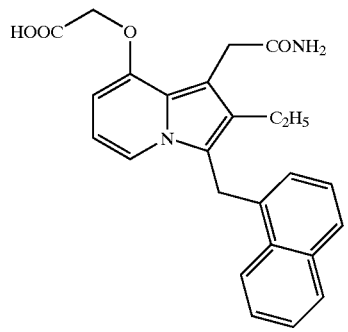
(22w)
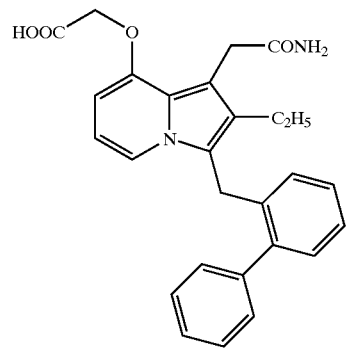
(22x)
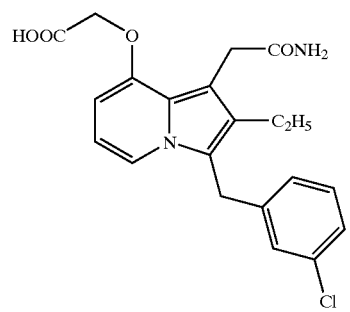
(22y)
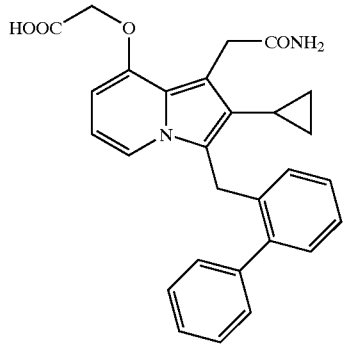
(22z)
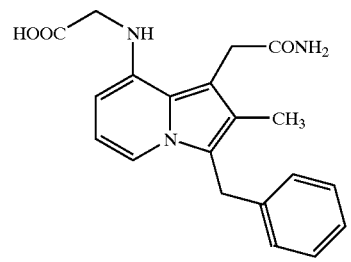
(92)
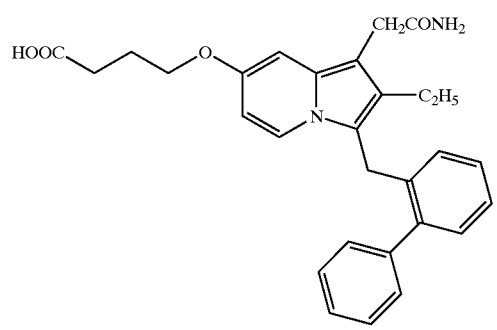
(71b)
and mixtures of the above compounds.
(AB) Indolizine Compounds of Type "A"—With Glyoxylamide Functionality
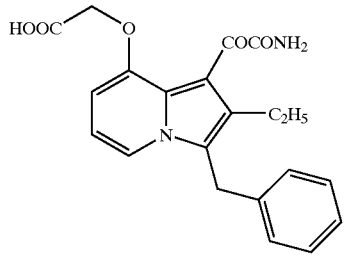
(40a)

(40d) (40g) (40h) (40i) (40j) (40k) (40l) (42) (52a) (52b)

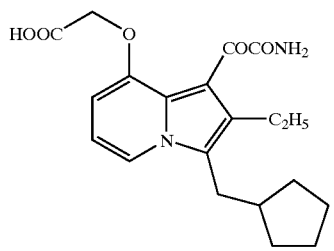
(52c)
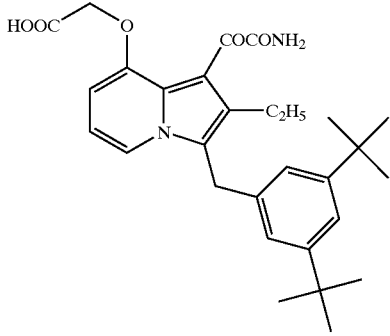
(52h)
(52d)
(52i)
(52e)
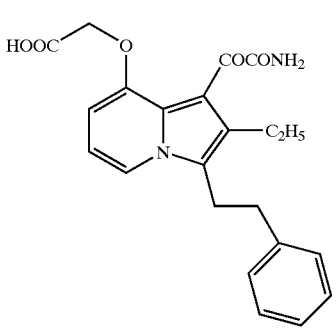
(52j)
(52f)
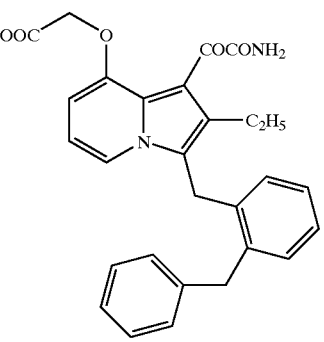
(52k)
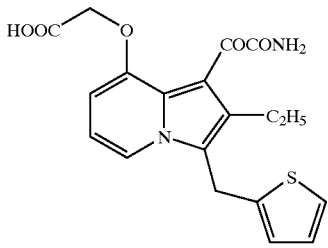
(52g)
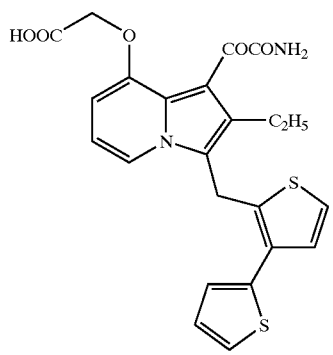
(52l)

(52m) 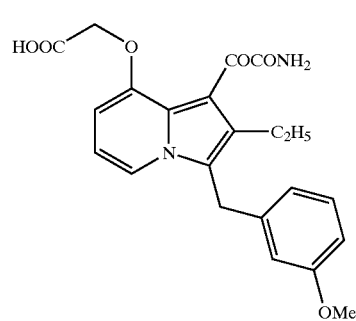
(52n) 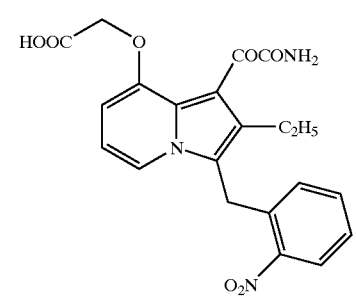
(52o) 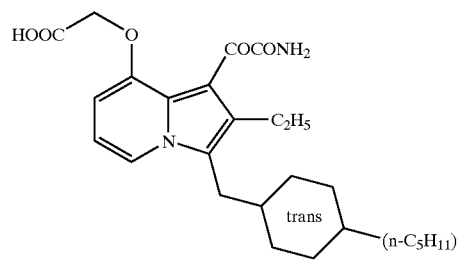
(52p) 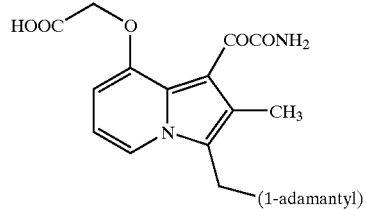
(52q) 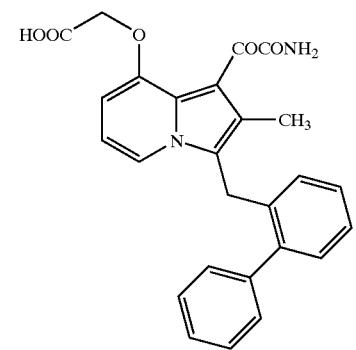
(52r) 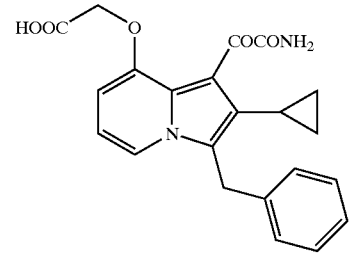
(52s) 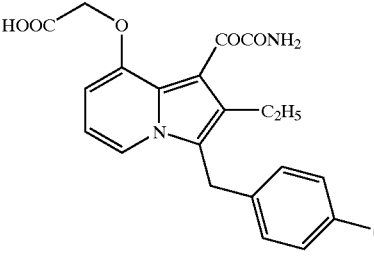
(52t) 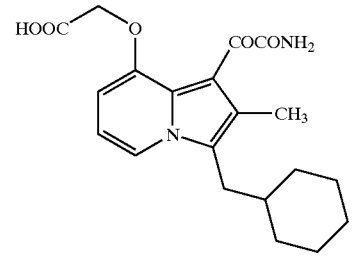
(52u) 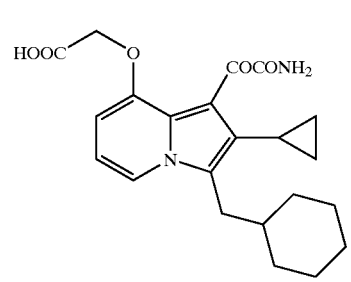
(52v) 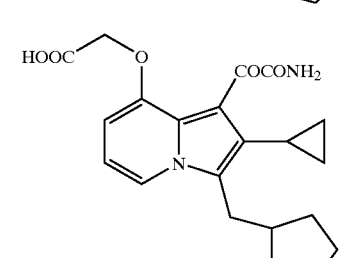
(52w) 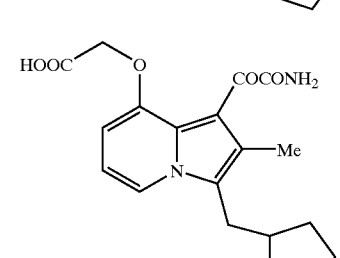

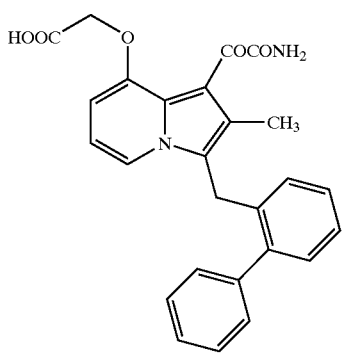
(58a)
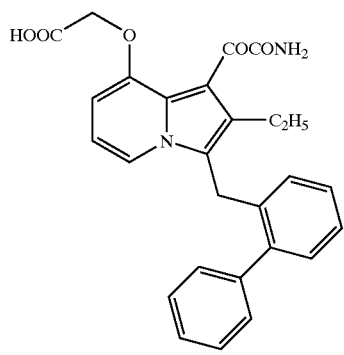
(58b, 40d)
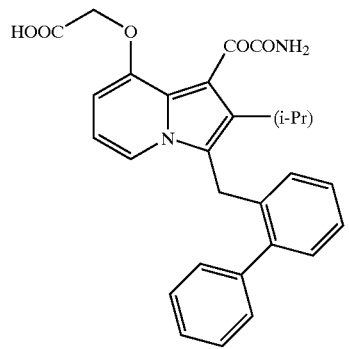
(58c)
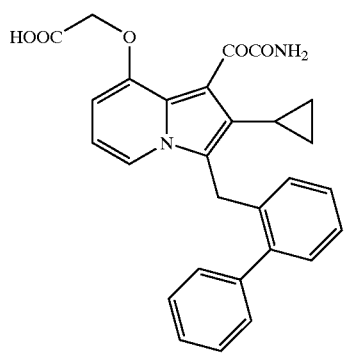
(58d, 40k)
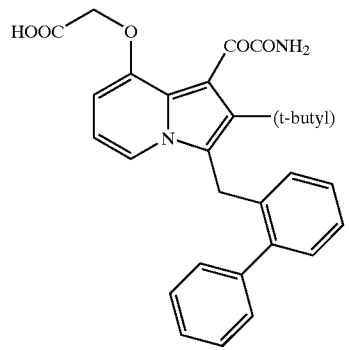
(58e)
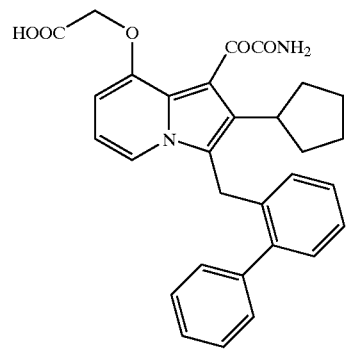
(58f)
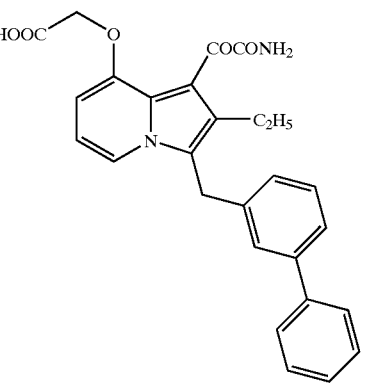
(58g)
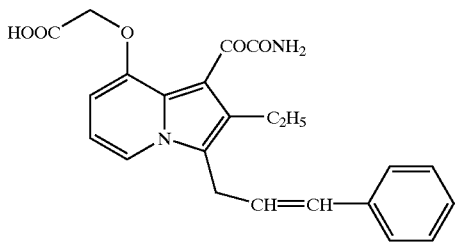
(58h)
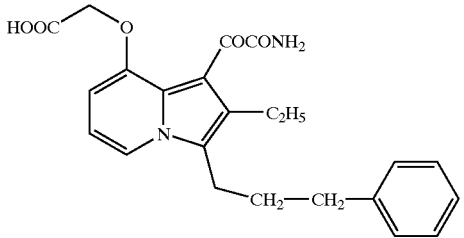
(58i)

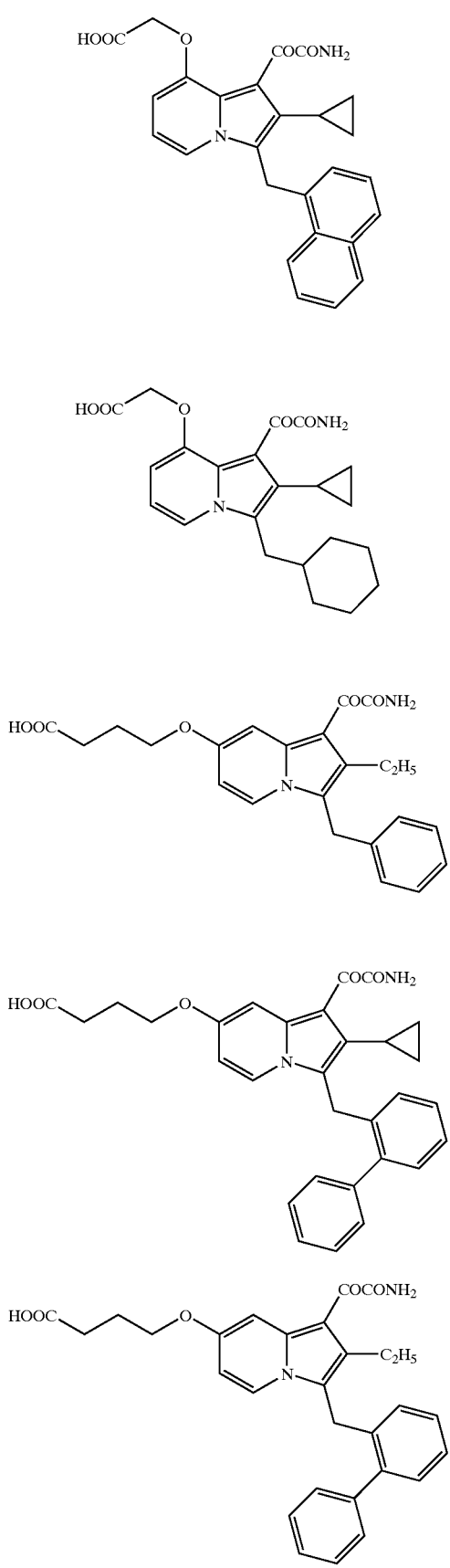

-continued

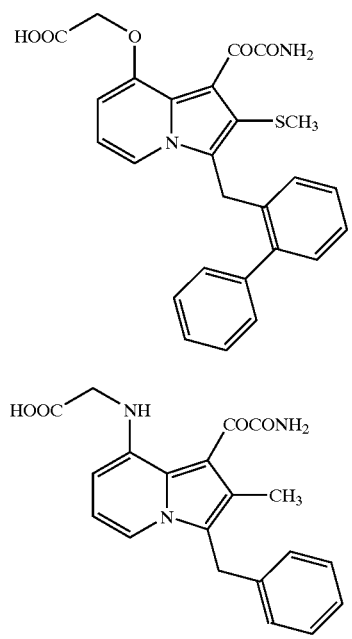

(70b)

(83)

(90b)

(97)

and mixtures of the above compounds.

(AC) Indolizine Comoounds of Type "B"—With Glyoxyla-mide Functionality

An indolizine-3-acetamide functional compound and a pharmaceutically acceptable salt, solvate or prodrug derivative thereof; wherein said compound is selected from the group represented by the following formulae:

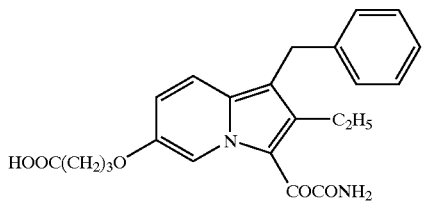

(11)

and mixtures of the above compounds.

The salts of the above indolizine-1-funcrional and indolizine-3-functional compounds represented by formulae (IA), (IIA), (IIIA), (IB), (IIB), (IIIB) and the individual formulae of Sections (AA), (AB) and (AC), supra, are an additional aspect of the invention. In those instances where the compounds of the invention possess acidic or basic functional groups various salts may be ormed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: pp.1–19 (1977)). Moreover, the basic group(s) of the compounds of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans- isomeric forms of the compounds. The R- and S- isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. The prodrug derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

Synthesis Methods

The following abbreviations are used throughout the synthesis Schemes and Examples:

| | |
|---|---|
| Bn | benzyl |
| THF | tetrahydrofuran |
| LAH | lithium aluminum hydride |
| LDA | lithium diiopropyl amine |
| DBU | 1,8-diazabicyclo 5.4.0]undec-7-une |

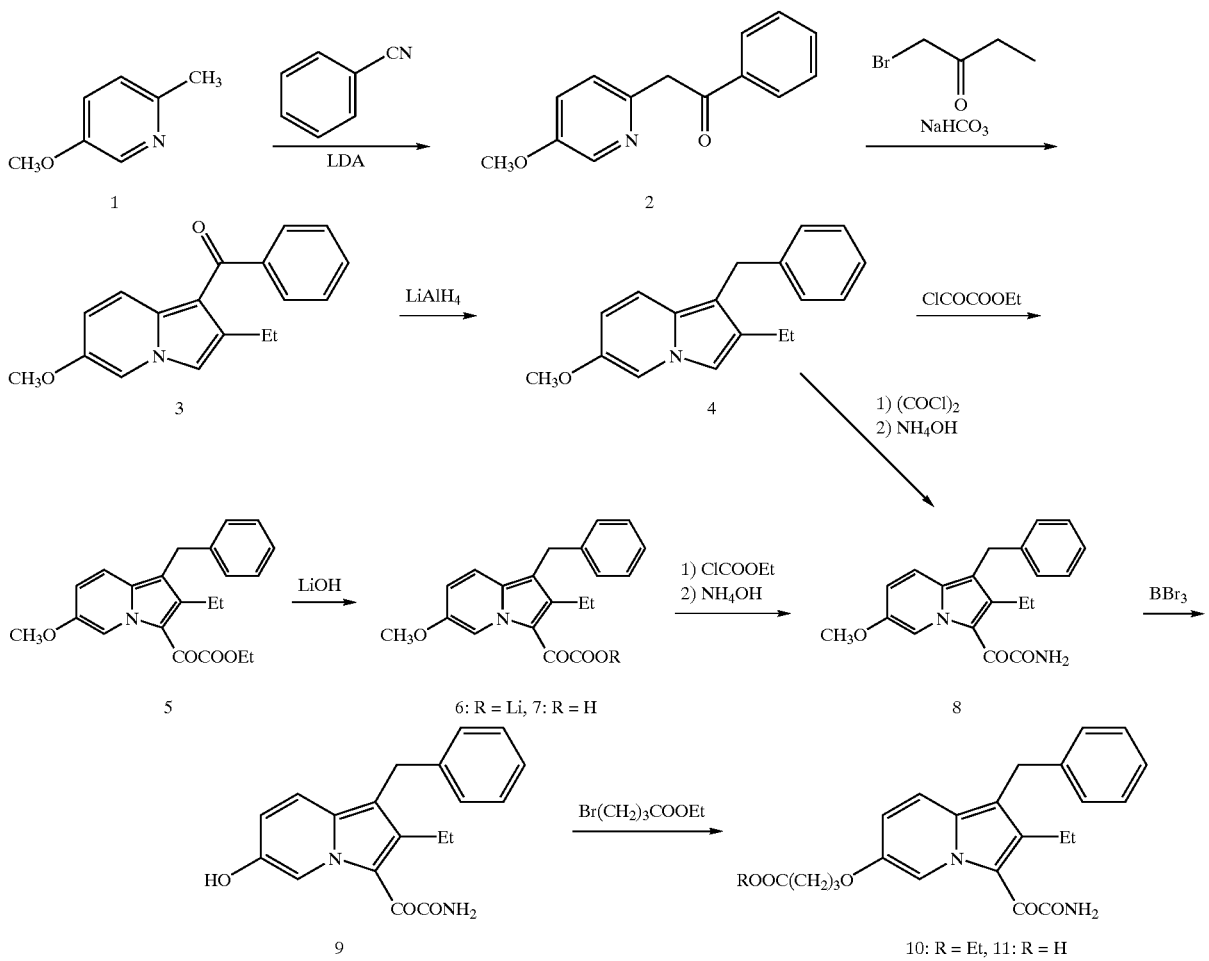

Scheme 1 - Part 1

The anion of 2-methyl-5-methoxypyridine is formed in THF using lithium diisopropyl amide and reacted with benzonitrile to produce 2. Alkylation of the nitrogen of 2 by 1-bromo-2-butanone followed by base catalyzed cyclization forms 3 which is reduced by LAH to 4. Sequential treatment of 4 with oxalyl chloride and ammonia gives 8. Alternatively, 4 is acylated with ethyl oxalyl chloride to give 5 which is converted to 6 with lithium hydroxide and then to 8 by sequential treatment with ethyl chloroformate and ammonium hydroxide. Demethylation of 8 by BBr$_3$ yields 9 which is O-alkylated using base and ethyl 4-bromobutyrate to form 10. Hydrolysis of 10 by aqueous base produces 11.

Scheme 2 - Part 1

12

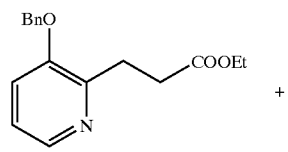

+

13

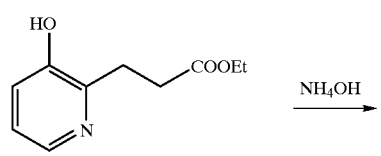

14

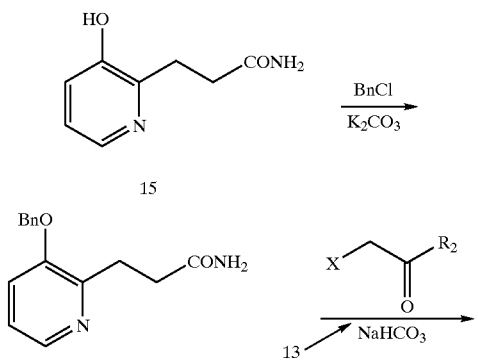

15

16

17a–d

| 17 | R₁ | R₂ | R₃ |
|---|---|---|---|
| a: | OEt | Et | Bn |
| b: | NH₂ | Et | Bn |
| c: | NH₂ | Et | CH₂COEt |
| d: | NH₂ | cyclo-Pr | Bn |

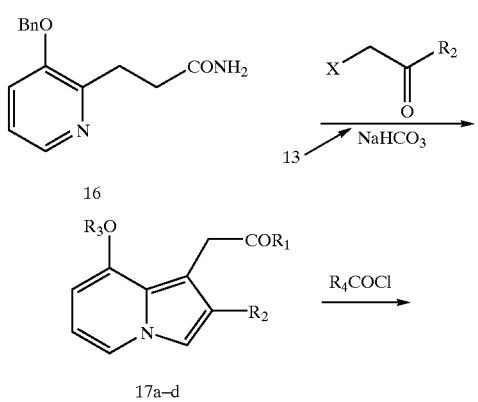

18a–g

-continued

| 18 | R₁ | R₂ | R₃ | R₄ |
|---|---|---|---|---|
| a: | OEt | Et | Bn | o-Ph—Ph |
| b: | NH₂ | Et | Bn | o-Ph—Ph |
| c: | NH₂ | Et | Bn | m-Cl—Ph |
| d: | NH₂ | Et | CH₂COEt | m-Cl—Ph |
| e: | NH₂ | cyclo-Pr | Bn | o-Ph—Ph |
| f: | NH₂ | Et | Bn | Ph |
| g: | NH₂ | Et | Bn | 1-Naphthyl |

Compound 12 (N. Desidiri, A. Galli, I. Sestili, and M. L. Stein, *Arch. Pharm.* (Weinheim) 325, 29, (1992)) is reduced by hydrogen in the presence of Pd/C to 14 which gives 15 on ammonolysis using ammonium hydroxide. O-alkylation of 15 using benzyl chloride and base affords 16. Alkylation of the nitrogen atom of 13 or 16 by 1-bromo-2-ketones followed by base catalyzed cyclization yields indolizines 17 which are acylated by aroyl halides to form 18.

Scheme 2-Part 2

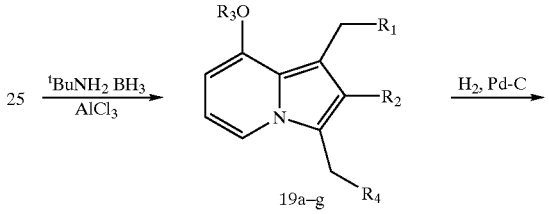

19a–g

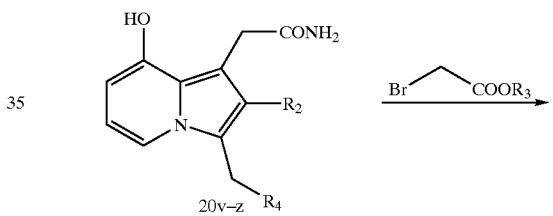

20v–z

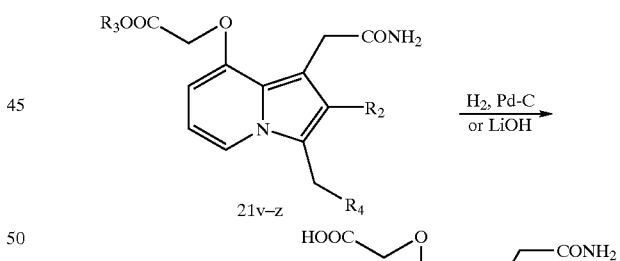

21v–z

22v–z

| 19 | R₁ | R₂ | R₃ | R₄ |
|---|---|---|---|---|
| a: | CH₂OH | Et | Bn | o-Ph-Ph |
| b: | CONH₂ | Et | Bn | o-Ph-Ph |
| c: | CONH₂ | Et | CH₂CH(OH)Et | m-Cl-Ph |
| d: | CONH₂ | Et | Bn | m-Cl-Ph |
| e: | CONH₂ | cyclo-Pr | Bn | o-Ph-Ph |
| f: | CONH₂ | Et | Bn | Ph |
| g: | CONH₂ | Et | Bn | 1-Naphthyl |

-continued

| 20–22 | $R_2$ | $R_3$ | $R_4$ |
|---|---|---|---|
| v: | Et | Et | Ph |
| w: | Et | Me | 1-Naphthyl |
| x: | Et | Bn | o-Ph-Ph |
| y: | Et | Bn | m-Cl-Ph |
| z: | cyclo-Pr | Me | o-Ph-Ph |

Reduction of 18 by tert-butylamine-borohydride and aluminum chloride yields 19 which is reduced by hydrogen in the presence of Pd/C to give 20. O-alkylation of 20 by benzyl bromoacetate and base forms 21 which is converted to the acid 22 by debenzylation using hydrogen in the presence of Pd/C.

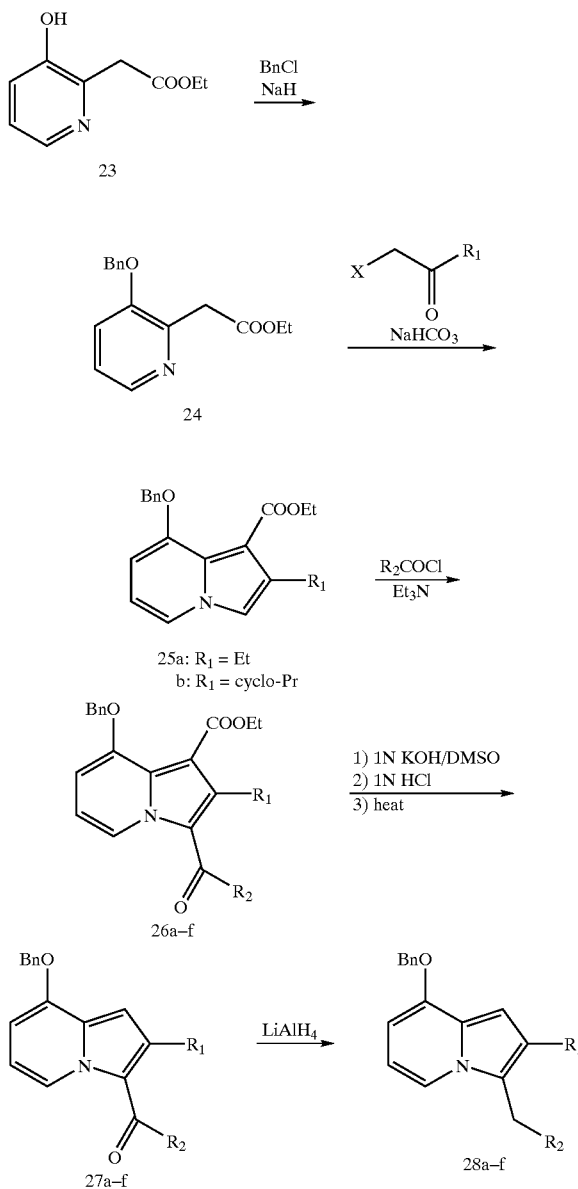

Scheme 3-Part 1

-continued

| 26–28 | $R_1$ | $R_2$ |
|---|---|---|
| a: | Et | Ph |
| b: | Et | o-Ph-Ph |
| c: | Et | m-Cl-Ph |
| d: | Et | m-$CF_3$-Ph |
| e: | Et | 1-Naphthyl |
| f: | cyclo-Pr | o-Ph-Ph |

Compound 23 (N. Desideri F. Manna, M. L. Stein, G. Bile, W. Filippeelli, and E. Marmo, *Eur. J. Med. Chem. Chim. Ther.*, 18, 295, (1983)) is O-alkylated using sodium hydride and benzyl chloride to give 24. N-alkylation of 24 by 1-bromo-2-butanone or chloromethylcyclopropyl ketone and subsequent base catalyzed cyclization gives 25 which is acylated by aroyl halide to give 26. Hydrolysis of the ester function of 26 followed by acidification forms an acid which is thermally decarboxylated to give 27. Reduction of the ketone function of 27 by LAH yields indolizines 28.

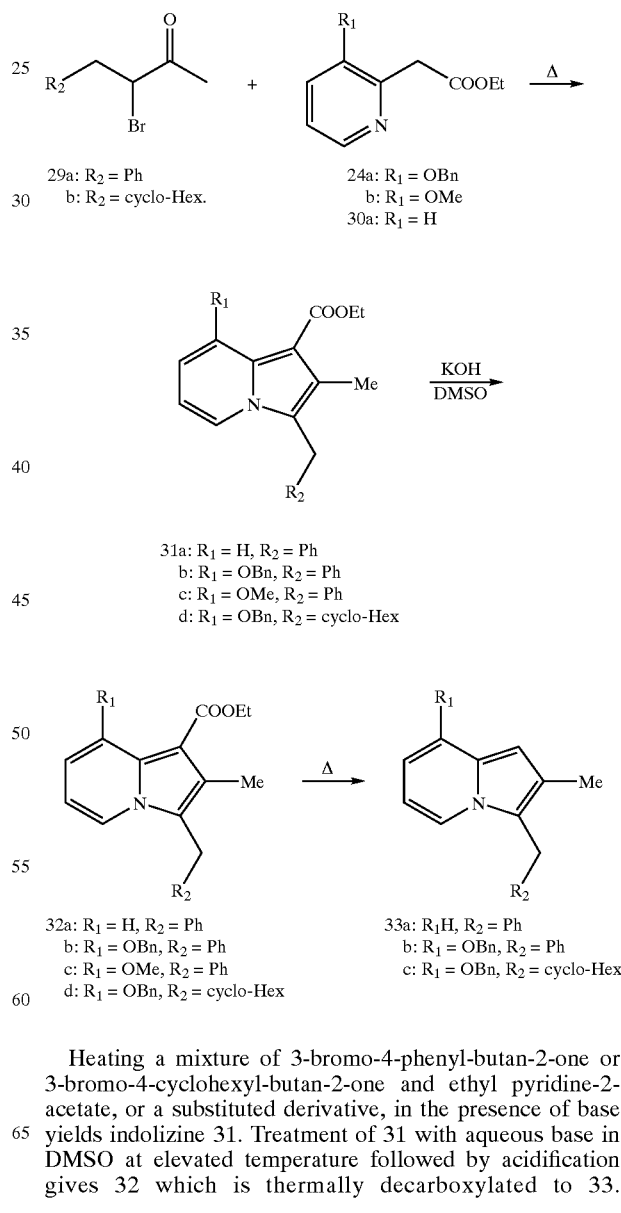

Scheme 3-Part 2

Heating a mixture of 3-bromo-4-phenyl-butan-2-one or 3-bromo-4-cyclohexyl-butan-2-one and ethyl pyridine-2-acetate, or a substituted derivative, in the presence of base yields indolizine 31. Treatment of 31 with aqueous base in DMSO at elevated temperature followed by acidification gives 32 which is thermally decarboxylated to 33.

Scheme 4-Part 1

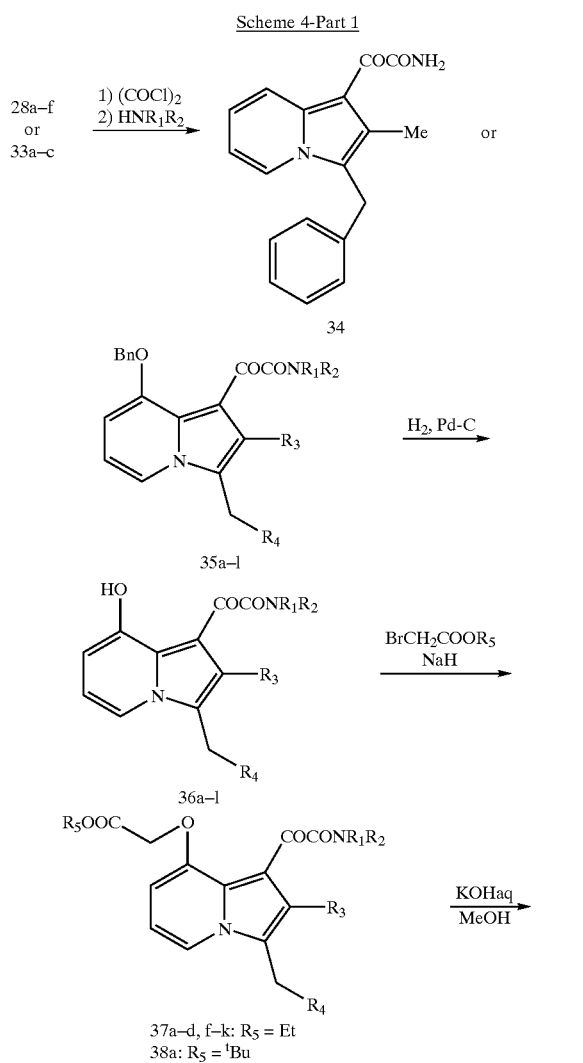

Sequential treatment of 28 or 33 with oxalyl chloride and ammonium hydroxide forms 35 which is debenzylated by hydrogen in the presence of Pd/C to give 36. Indolizines 36 are O-alkylated using sodium hydride and bromoacetic acid esters to form 37, 38, or 39 which are converted to indolizines 40 by hydrolysis with aqueous base followed by acidification.

Scheme 4-Part 2

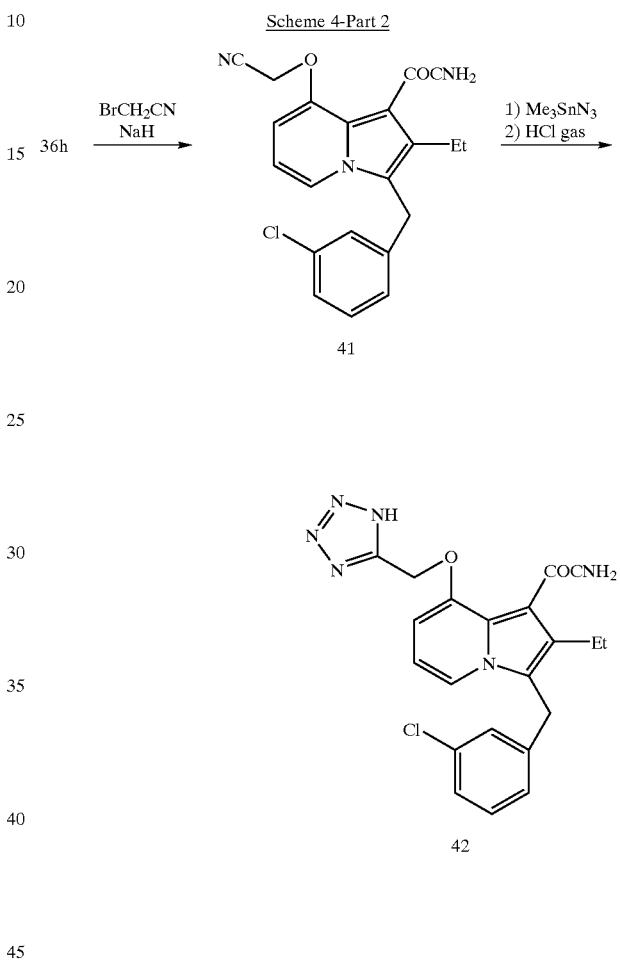

The O-alkylation of 36 h produces nitrite 41 which is converted to 42 on reaction with trialkyltin azide.

| 35–40 | $R_1$ | $R_2$ | $R_3$ | $R_4$ |
|---|---|---|---|---|
| a: | H | H | Et | Ph |
| b: | H | Me | Et | Ph |
| c: | Me | Me | Et | Ph |
| d: | H | H | Et | o-Ph-Ph |
| e: | H | Me | Et | o-Ph-Ph |
| f: | Me | Me | Et | o-Ph-Ph |
| g: | H | H | Me | Ph |
| h: | H | H | Et | m-Cl-Ph |
| i: | H | H | Et | m-CF$_3$-Ph |
| j: | H | H | Et | 1-Naphthyl |
| k: | H | H | cyclo-Pr | o-Ph-Ph |
| l: | H | H | Me | cyclo-Hex |

Scheme 5

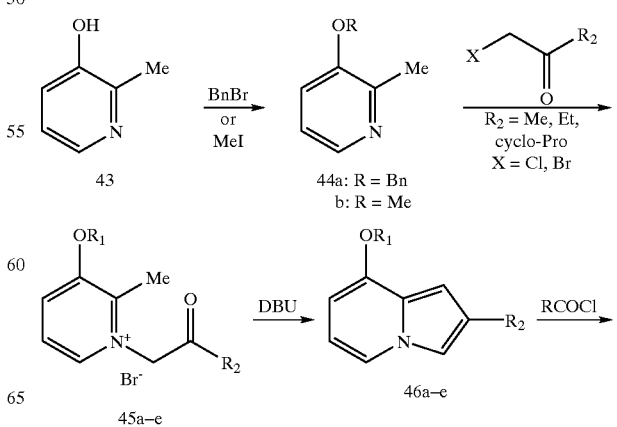

-continued
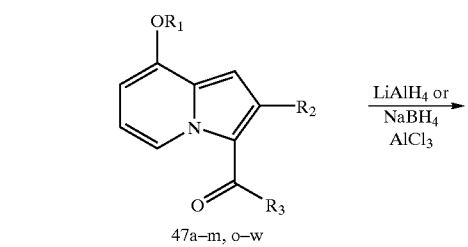
47a–m, o–w
| 45, 46 | $R_1$ | $R_2$ | | 47–52 | $R_1$ | $R_2$ | $R_3$ |
|---|---|---|---|---|---|---|---|
| a: | Bn | Et | | a–o | Bn | Et | a–o (see below) |
| b: | Me | Et | | p | Bn | Me | 1-adamantyl |
| c: | Bn | Me | | q | Bn | Me | o-biphenyl |
| d: | Me | cyclo-Pro | | r | Bn | cyclo-Pro | phenyl |
| e: | Bn | cyclo-Pro | | s | Me | Et | p-n-$C_4H_9$-Ph |
| | | | | t | Bn | Me | cyclo-Hex |
| | | | | u | Me | cyclo-Pro | cyclo-Hex |
| | | | | v | Bn | cyclo-Pro | cyclophenyl |
| | | | | w | Bn | Me | cyclolphenyl |
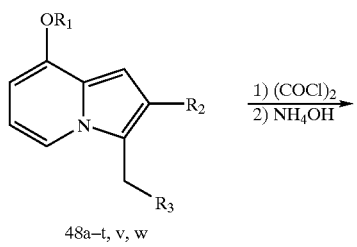
48a–t, v, w
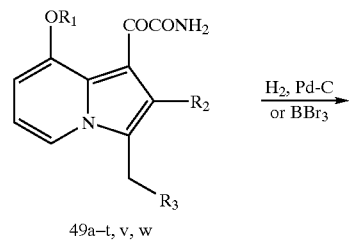
49a–t, v, w
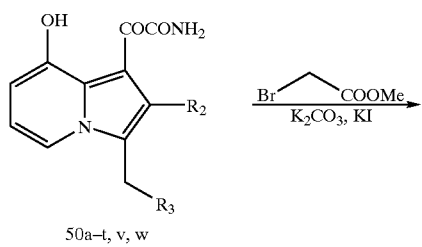
50a–t, v, w
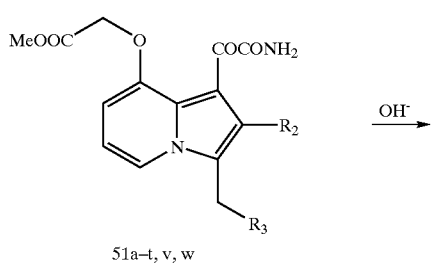
51a–t, v, w
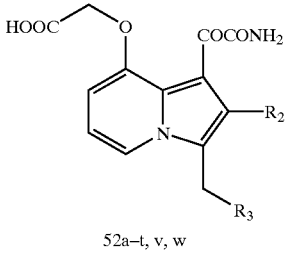
52a–t, v, w
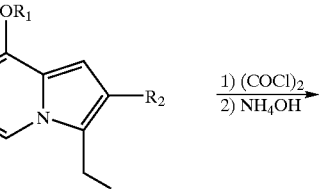
48a–t,
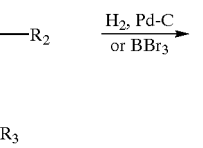
49a–t
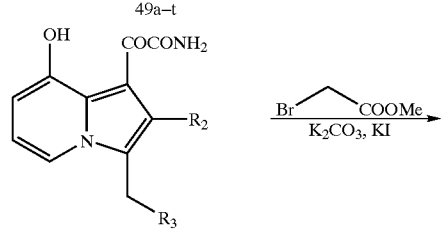
50a–t
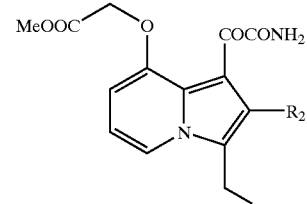
51a–t
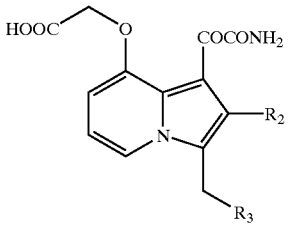
52a–t
47–52 $R_3$ =
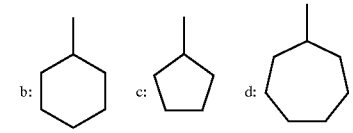

e: n-C₄H₉

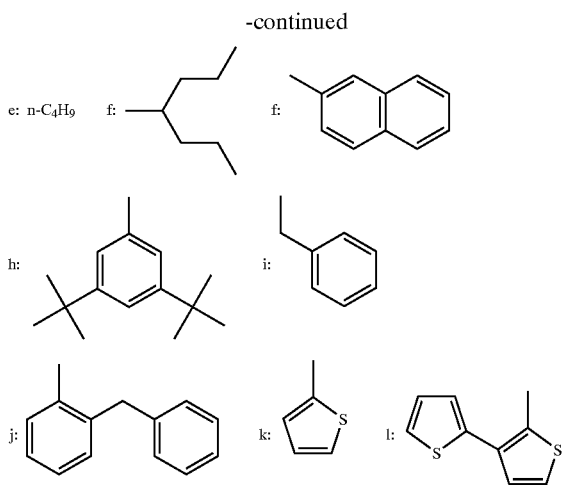

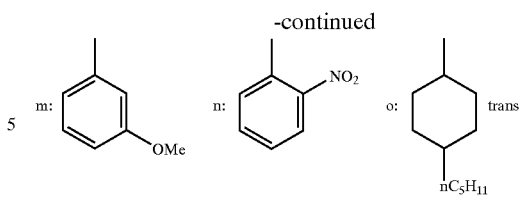

The hydroxypyridine is O-alkylated to give 44 which is heated with 2-haloketones to produce 45. Treatment of 45 with base causes cyclization to 46 which on heating with acid chlorides yields acylindolizines 47 which are reduced by aluminum hydride to the corresponding alkylindolizines 48. Sequential treatment of 48 with oxalyl chloride and then ammonia gives 49. Cleavage of the ether functionality of 49 yields 50. The oxyacetic ester derivatives 51 are formed by O-alkylation of 50 and then hydrolyzed to the oxyacetic acids 52.

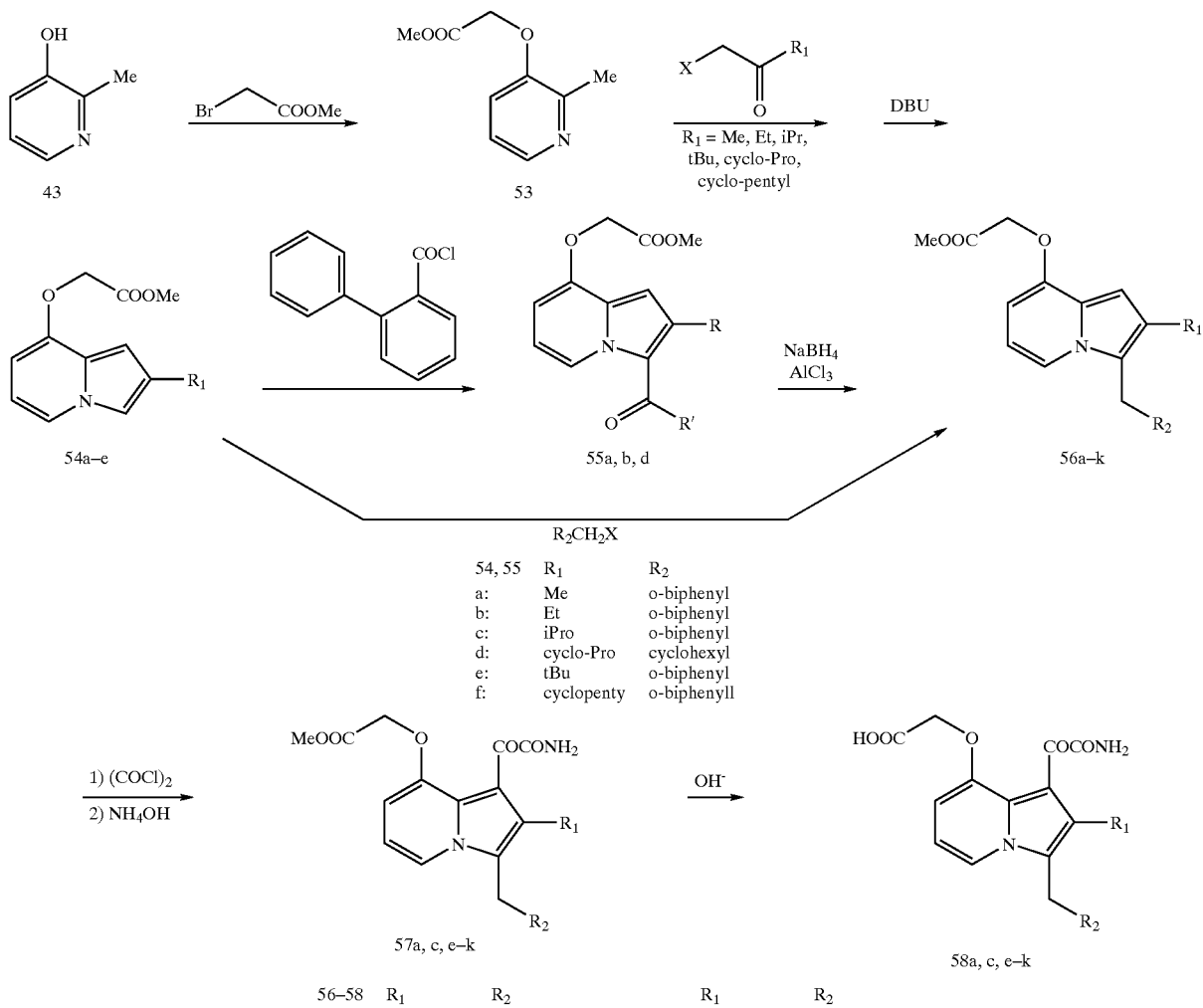

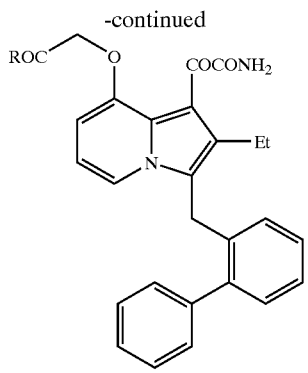

59a–k

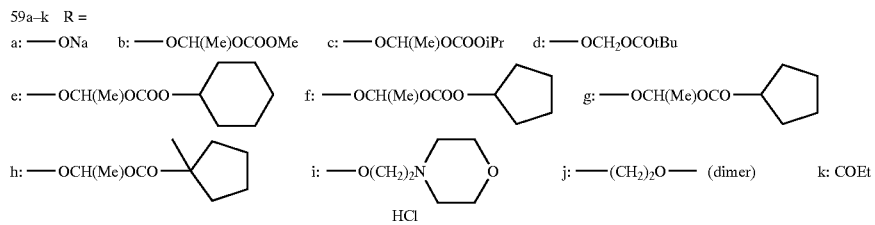

Pyridine 43 is O-alkylated to produce 53. Heating 53 with 2-haloketones gives intermediate N-alkylated pyridinium compounds which are cyclized to 54 on treatment with base. Heating 54 with acyl chlorides gives the acylindolizines 55 which are reduced to the alkylindolizines 56 by sodium borohydride-aluminum chloride. Alternatively, 56 are produced by C-alkylation of 54 using alkyl halides. Sequential treatment of 56 with oxalyl chloride and then ammonia gives 57 which are hydrolyzed to produce 58. Compound 58b is converted to its sodium salt 59a which yields 59b-k on reaction with the appropriate alkyl halide.

Compound 36b is O-alkylated to give 59l-p.

Scheme 7

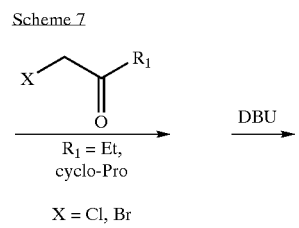

Scheme 6 - Part 2

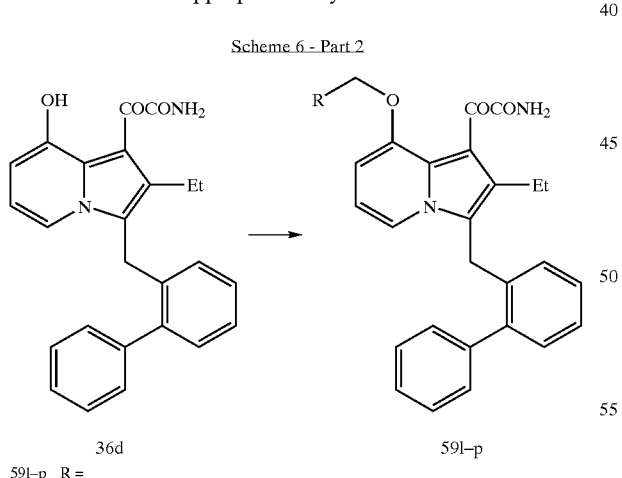

59l–p R =

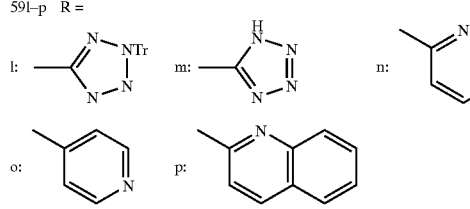

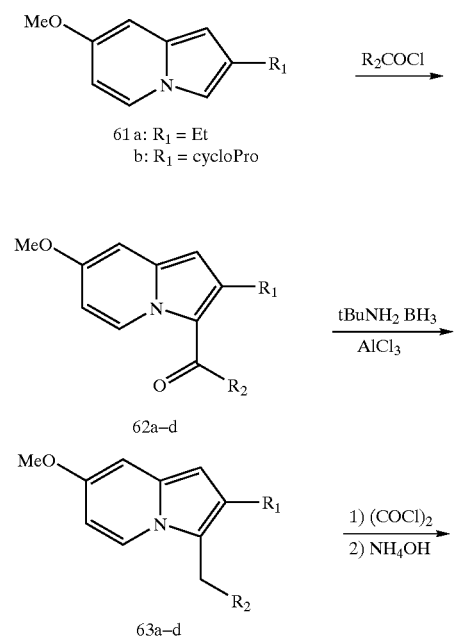

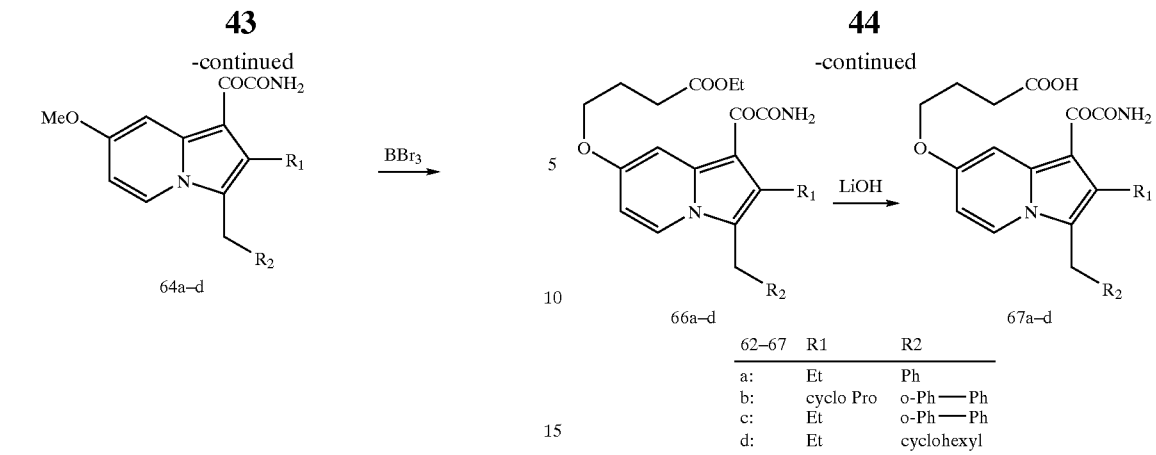
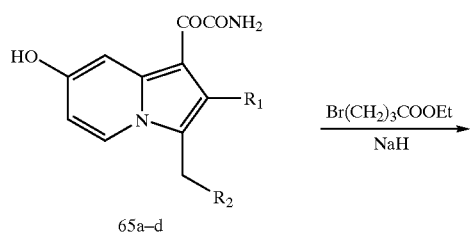

| 62–67 | R1 | R2 |
|---|---|---|
| a: | Et | Ph |
| b: | cyclo Pro | o-Ph—Ph |
| c: | Et | o-Ph—Ph |
| d: | Et | cyclohexyl |

Pyridine 60 is N-alkylated by 2-haloketones to produce intermediate pyridinium compounds which are cyclized by base to give 61. Reaction of 61 with acyl chlorides produces 62 which are reduced to 63 by tert butylamine-borane and aluminum chloride. Sequential treatment of 63 with oxalyl chloride and then ammonia yields 64 which are O-demethylated by BBr$_3$ to give 65. The sodium salt of 65 is reacted with ethyl 4-bromobutyrate to give 66 which is hydrolyzed to the acid 67.

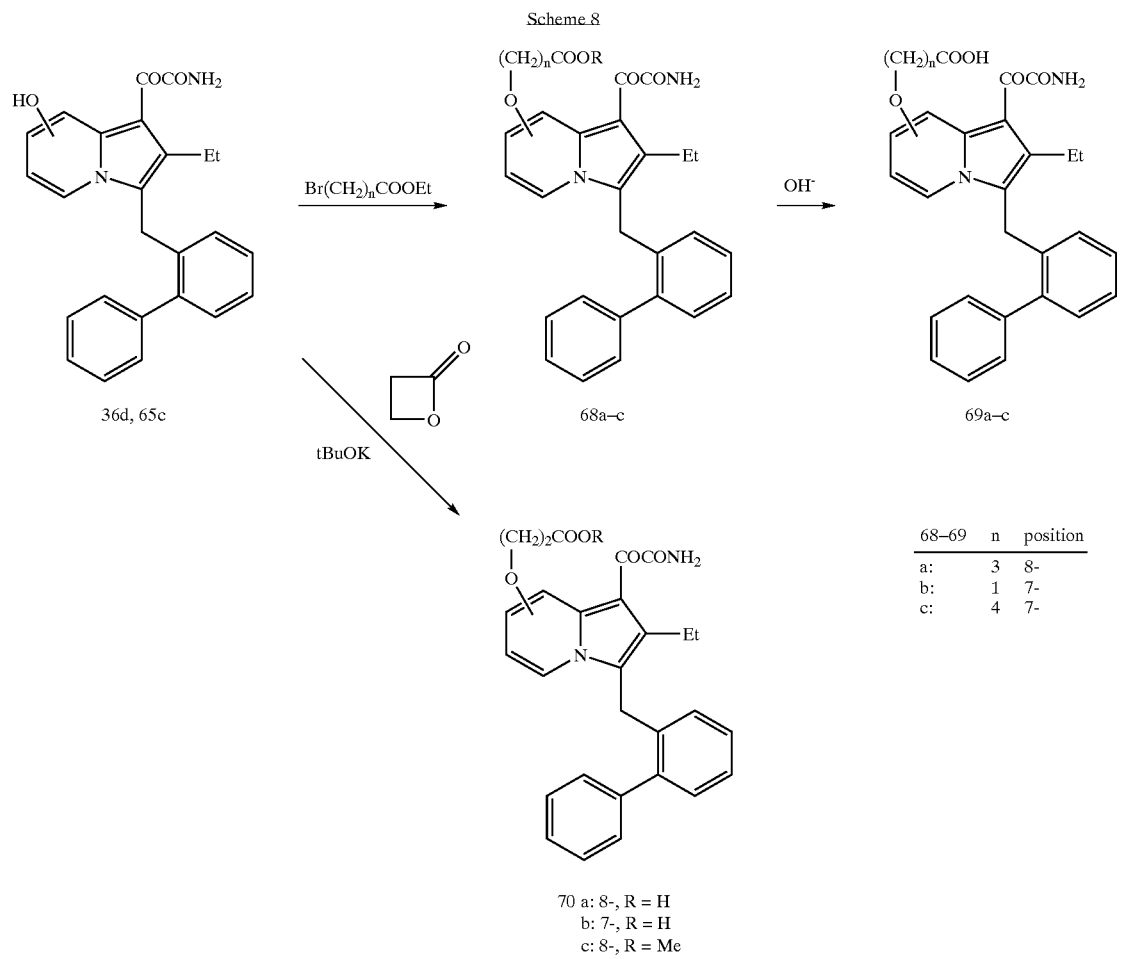

| 68–69 | n | position |
|---|---|---|
| a: | 3 | 8- |
| b: | 1 | 7- |
| c: | 4 | 7- |

Compounds 36d and 65c are O-alkylated by omega-bromnocarboxylic esters to give 68 which are hydrolyzed to the acids 69. Compounds 36d and 65c produce 70 on treatment with propiolactone and base.
Scheme 9
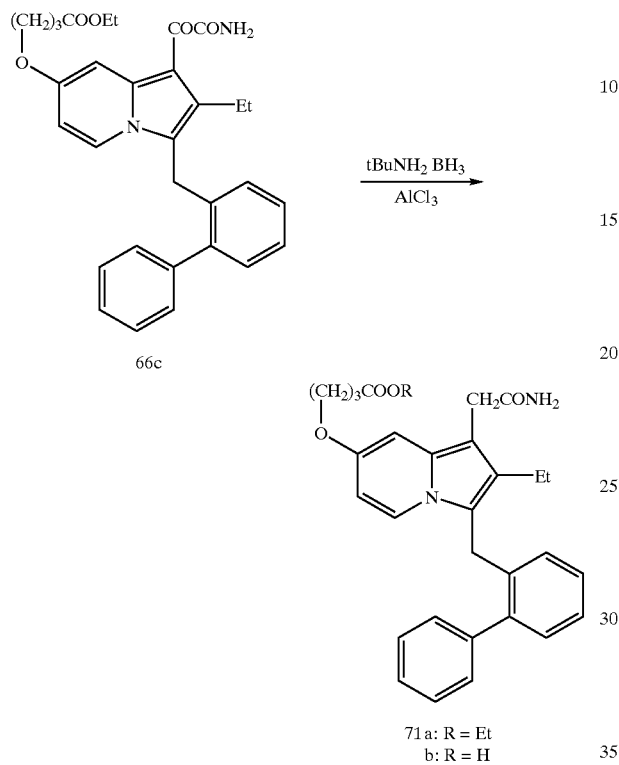
66c
71a: R = Et
b: R = H
Compounds 66 are reduced to 71 by tert-butylamine-borane and aluminum chloride.
Scheme 10
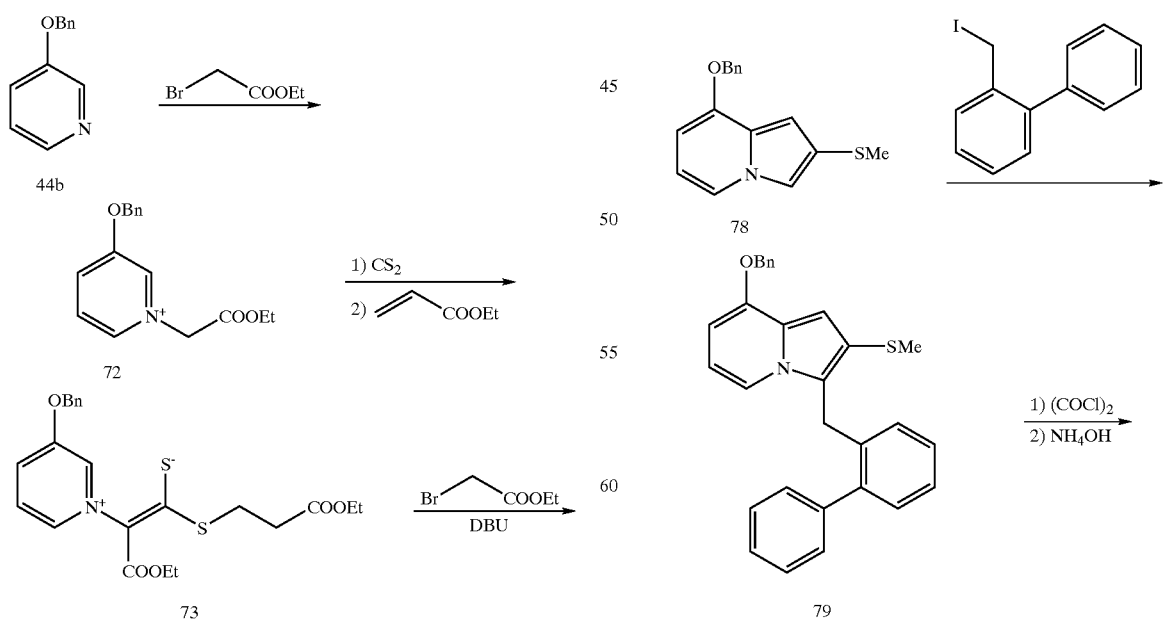
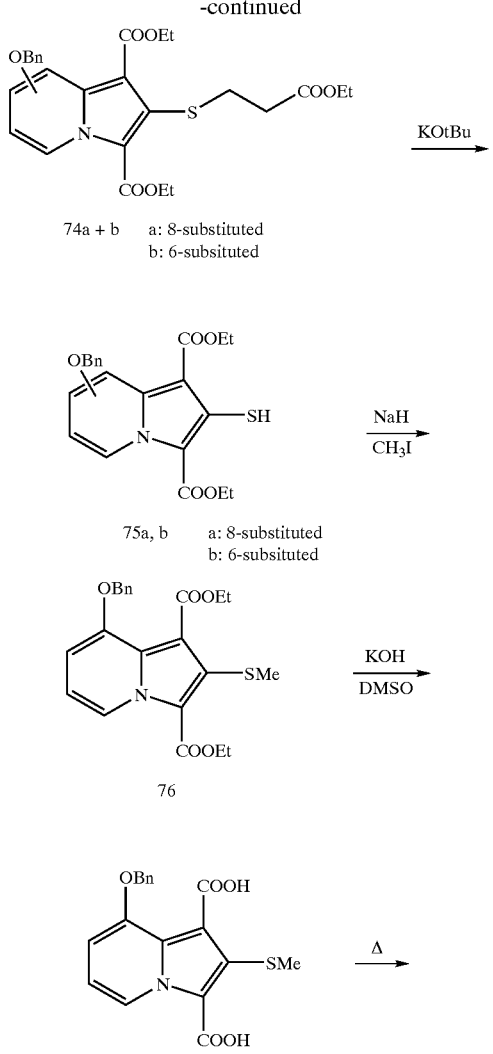
74a + b   a: 8-substituted
         b: 6-substituted
75a, b   a: 8-substituted
         b: 6-substituted

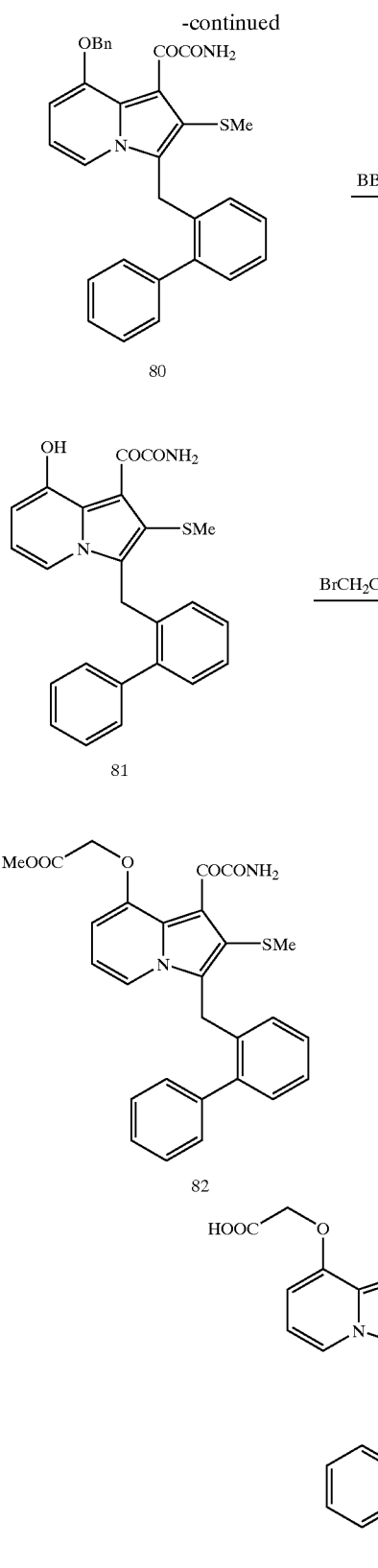

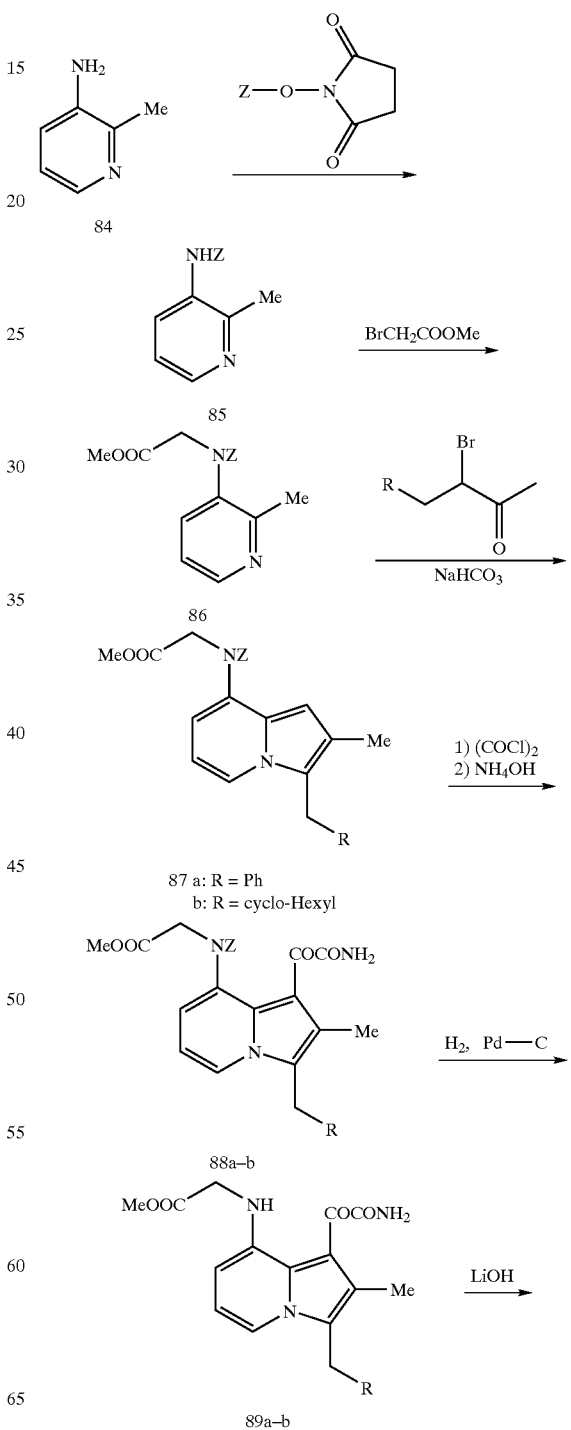

8-benzyloxy compounds. Base treatment of 74a+b eliminates ethyl acrylate to form 75 which is separated from the isomer of 6-benzyloxy derivative and S-alkylated to give 76. Hydrolysis of 76 forms 77 which is thermally decarboxylated to yield 78. Compound 78 is C-alkylated to form 79 which on sequential treatment with oxalyl chloride and then ammonia forms 80. Ether cleavage of 80 gives 81 whose sodium salt is alkylated by methyl bromoacetate to form 82 which are hydrolyzed to acids 83.

Scheme 11 - Part 1

Pyridine 44b reacts with ethyl bromoacetate to produce 72 which is treated with $CS_2$ and base and then with ethyl acrylate to form 73. Reaction of 73 with base and ethyl bromoacetate yields a mixture of regioisomers 74a+b, 6- and -continued

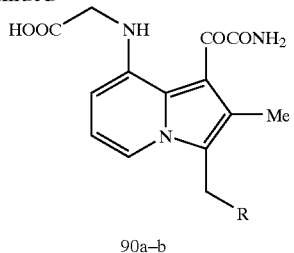

90a–b

Aminopicoline 84 is converted to its N-CBZ derivative 85 whose anion is alkylated by methyl bromoacetate to produce 86. Reaction of 86 with methyl alpha-bromoalkyl ketones in the presence of base yields 87. Sequential treatment of 87 with oxalyl chloride and then ammonia gives 88 which is converted to 89 by hydrogenolysis of the N-CBZ function. Hydrolysis of 89 yields acids 90.

Scheme 11
Part 2

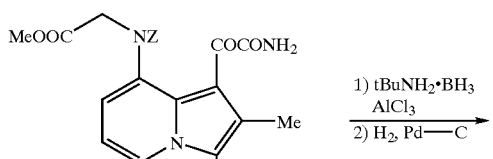

88a

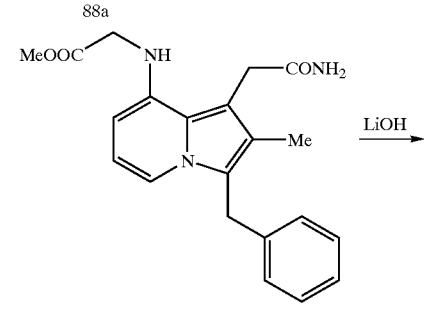

91

92

Compounds 88 are reduced by tert-butylamine-borane and aliuminum chloride to 91 which are hydrolyzed to acids 92.

Scheme 12

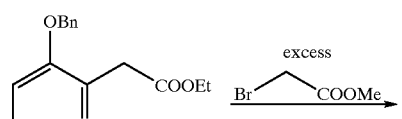

24

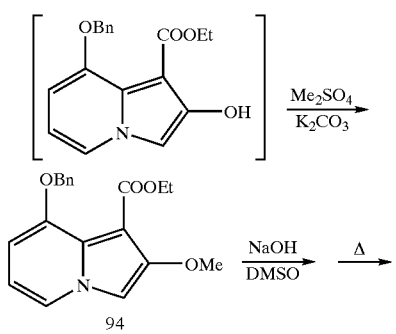

93

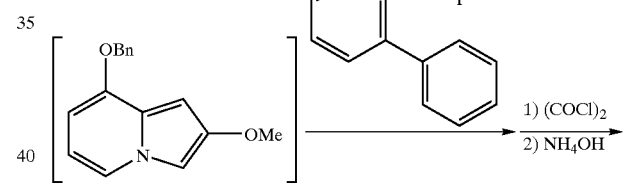

94

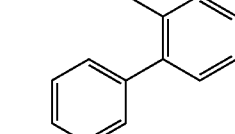

95

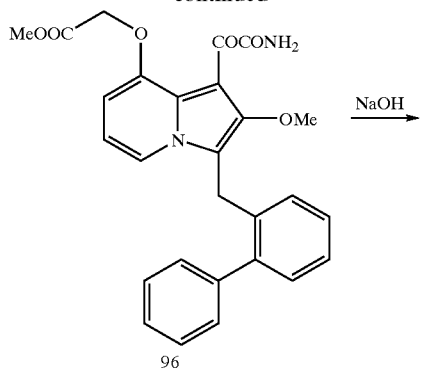

96

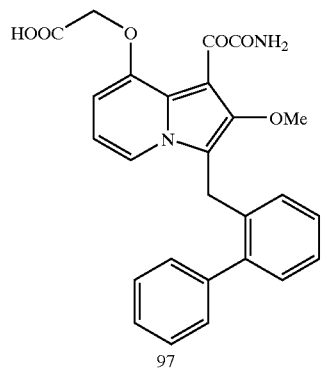

97

Pyridine 24 is N-alkylated by methyl bromoacetate, cyclized with base, and o-methylated using dimethysulfate to give 94. Hydrolysis of the ester function of 94 followed by thermal decarboxylation yields 2-methoxy-8-benzyloxyindolizine which is C-alkylated at position 3 and then reacted sequentially with oxalyl chloride and ammonia to produce 95. Hydrogenolysis of the 8-benzyloxy group followed by O-alkylation gives 96 which is hydrolyzed to 97.

EXAMPLES

Reference numbers in the following Examples refer to compounds shown in the preceding Schemes.

Example 1
Part A: Preparation of 5-Methoxy-2-phenacyl-pyridine 2

A solution of n-butyllithium in hexane (1.6 M, 11.4 ml, 18.2 m mol) was added dropwise to a solution of diisopropylamine (1.81 g, 17.9 m mol) in tetrahydrofuran (50 ml) at −60—−70° C. under nitrogen. The mixture was stirred for 10 min. A solution of 5-methoxy-2-methylpyridine (1, L. Marion and W. F. Cockburn, J. Am. Chem. Soc.,71, 3402 (1949)) (2.20 g, 17.9 m mol) in tetrahydrofuran (4 ml) was added dropwise. The mixture was stirred for 10 min. A solution of benzonitrile (1.84 g, 17.9 m mol) in tetrahydrofuran (8 ml) was added dropwise at −70° C. The mixture was stirred at −78° C. for 1 hour and at room temperature for 2 hours and poured to ice-cold aqueous ammonium chloride. The organic phase was separated and the aqueous phase was extracted with ether. The combined organic phases were extracted with dilute hydrochloric acid. The extracts were washed with ether, basified with 10% aqueous sodium hydroxide and extracted with ether. The extracts were washed with water, dried over $Na_2SO_4$. After removing the solvent at reduced pressure, the residue was chromatographed on silica gel eluting with hexane:AcOEt (3:2) and crystallized from benzene:hexane to give 2.32 g (57.0% yield) of the titled compound.

The NMR showed to be a mixture of the keto and the enol tautomers. IR $v_{max}$ (nujol) 1685, 1630 cm$^{-1}$. $^1$H NMR (CDCl$_3$) δ 3.84–3.88 (3H, m), 4.45 (2H, m), 7.0–7.3 (3H, m), 7.82 (1H, m), 8.07 (2H, m), 8.27 (1H, m). Analyses: Calc'd for $C_{14}H_{13}NO_2$: C, 73.99; H, 5.77; N, 6.16. Found: C, 74.08; H, 5.85; N, 6.20.

Part B: Preparation of 1-Benzoyl-2-ethyl-6-methoxyindolizine 3

A mixture of the pyridine derivative (2, 2.146 g, 9.44 m mol), 1-bromo-2-butanone (2.14 g, 14.2 m mol) and sodium hydrogencarbonate (1.60 g, 19 m mol) in acetone (50 ml) was heated under reflux for 20 hours. The insoluble materials were removed off by filtration. The filtrate was concentrated under reduced pressure. The residue was recrystallized from benzene:hexane to give 2.39 g (90.7% yield) of the titled compound, mp, 138–139° C.

IR $v_{max}$ (nujol) 1600, 1592, 1505 cm$^{-1}$. $^1$H NMR (CDCl$_3$) δ 1.19 (3H, t, J=7.5 Hz), 2.72 (2H, q, J=7.4 Hz), 3.80 (3H, s), 6.69 (1H, dd, J=2.0, 9.8 Hz), 7.10 (1H, s), 7.26 (1H, d, J=9.6 Hz), 7.35–7.55 (4H, m), 7.67 (2H, m). Analyses: Calc'd for $C_{14}H_{14}NO_2$: C, 77.40; H, 6.13; N, 5.01. Found: C, 77.53; H, 6.27; N, 5.06.

Part C: Preparation of 1-Benzyl-2-ethyl-6-methoxyindolizine 4

The benzoyl derivative (3, 1.37 g, 4.90 m mol) was added in small portions to a slurry of lithiumaluminumhydride (1.03 g, 27.1 m mol) in ether (100 ml) with cooling in ice under nitrogen. The mixture was then heated under reflux for 4.5 hours. After cooling, the mixture was poured into ice-cold 5% aqueous sodium hydroxide and extracted with ether. The extracts were washed with water and dried over $Na_2SO_4$. The solvent was removed at reduced pressure to give 1.23 g (94.5% yield). The oily residue was used to the next preparation without further purification owing to the unstability.

IR $v_{max}$ (film) 1642, 1550, 1218 cm$^{-1}$. $^1$H NMR (CDCl$_3$) δ 1.18 (3H, t, J=7.6 Hz), 2.57 (2H, q, J=7.5 Hz), 3.75 (3H, s), 4.06 (2H, s), 6.38 (1H, dd, J=9.6, 2.2 Hz), 7.0–7.3 (7H, m), 7.39 (1H, d, J=2.2 Hz).

Part D: Preparation of Ethyl (1-Benzyl-2-ethyl-6-methoxyindolizin-3-yl)glyoxylate 5

A solution of ethyl oxalylchloride (0.67 g, 4.91 m mol) in benzene (10 ml) was added dropwise to a solution of the indolizine compound (4, 1.23 g, 4.64 m mol) in benzene (20 ml) with cooling in ice under nitrogen. The solution was stirred at room temperature for 2 hours, washed with aqueous sodium hydrogencarbonate and then water and dried over $Na_2SO_4$. After removing the solvent at reduced pressure, the residue was chromatographed on alumina (grade II) eluting with hexane:AcOEt (10:1) to give 1.66 g (98.5% yield) of the titled compound.

IR $v_{max}$ (film) 1732, 1582, 1530, 1224 cm$^{-1}$. $^1$H NMR (CDCl$_3$) δ 1.12 (3H, t, J=7.6 Hz), 1.42 (3H, t, J=7.3 Hz), 2.71 (2H, q, J=7.5 Hz), 3.87 (3H, s), 4.07 (2H, s), 4.42 (2H, q, J=7.1 Hz), 7.00 (1H, dd, J=1.8, 9.4 Hz), 7.05–7.3 (6H, m), 9.77 (1H, d, J=1.8 Hz).

Part E: Preparation of Lithium (1-Benzyl-2-ethyl-6-methoxyindolizin-3-yl)glyoxylate 6 and the Carboxylic Acid 7

A solution of LiOH 1H$_2$O (1.0 g) in water (10 ml) was added to a solution of the ester (1.46 g) in methanol (10 ml). The mixture was stirred at room temperature for 4 hours. The solid was collected by filtration washed with small amount of water and with ether and dried to give the salt (670 mg), mp >300° C. IR $v_{max}$ (nujol) 1608, 1579, 1530, 1372 cm⁻¹ The filtrate was acidified to pH 4 with dilute hydrochloric acid and extracted with ether. The extracts were washed with water and dried over Na$_2$SO$_4$. After removing the solvent at reduced pressure, the titled carboxylic acid was obtained and unstable on standing at room temperature.

¹H NMR (CDCl$_3$) δ 1.16 (3H, t, J=7.5 Hz), 2.89 (2H, q, J=7.4 Hz), 3.86 (3H, s), 4.07 (2H, s), 7.0–7.3 (7H, m), 9.72 (1H, d, J=1.6 Hz).

Part F: Preparation of (1-Benzyl-2-ethyl-6-methoxyindolizin-3-yl)glyoxylamide 8

1) A solution of ethyl chlorocarbonate (220 mg, 2.03 m mol) in acetone (3 ml) was added dropwise to a mixture of the salt (7, 569 mg, 1.66 m mol) in water (2 ml) and acetone (5 ml) with cooling in ice. The mixture was stirred at 0° C. for 30 min and poured to 28% ammonium hydroxide. The mixture was stirred at room temperature for 2 hours and extracted with dichloromethane. The extracts were washed with water and dried over Na$_2$SO$_4$. After removing the solvent at reduced pressure, the residue was chromatographed on silica gel eluting with hexane:AcOEt (1:1) to give the titled compound, mp 159–160° C.

IR ν$_{max}$ (nujol) 3342, 3166, 1664, 1571 cm⁻¹.

2) A solution of the indolizine compound (4, 1.288 g, 4.85 m mol) in tetrahydrofuran (25 ml) was added dropwise to a solution of oxalyl chloride (3.18 g, 25 m mol) in tetrahydrofuran (5 ml) with cooling in ice. The mixture was stirred at 0° C. for 1 hour and added dropwise to 28% ammonium hydroxide (50 ml) with cooling in ice. The mixture was stirred for 1 hour at room temperature. Water was added. The mixture was extracted with dichloromethane. The extracts were washed with water and dried over Na$_2$SO$_4$. After removing the solvent at reduced pressure, the residue was crystallized from ethyl acetate:benzene to give 1.27 g (73.6% yield) of the titled compound.

Part G: Preparation of (1-Benzyl-2-ethyl-6-hydroxyindolizin-3-yl)glyoxylamide 9

A solution of borontribromide (976 mg, 3.89 m mol) in dichloromethane (5 ml) was added to a solution of the methoxy compound (8, 437 mg, 1.30 m mol) in dichloromethane (50 ml) at −20° C. The mixture was stirred at room temperature for 24 hours and poured to ice-water. A smal amount of methanol was added. The organic phase was separated and washed with water. After removing the solvent at reduced pressure, The residue was crystallized from dichloromethane, mp, 219–220° C. (dec.).

IR ν$_{max}$ (nujol) 3388, 3261, 3193, 1678, 1530 cm⁻¹.

Part H: Preparation of (1-Benzyl-6-(3-carbethoxypropyloxy)-2-ethylindolizin-3-yl)glyoxylamide 10

60% Sodium hydride (52 mg, 1.32 m mol) was added to a solution of the alcohol (9, 213 mg, 0.661 m mol) and ethyl 4-bromo-2-butyrate (283 mg, 1.45 m mol) in dimethylformamide (5 ml) with cooling in ice under nitrogen. The mixture was stirred at room temperature for 8.5 hours, poured so ice-water and extracted with ethyl acetate. The extracts were washed with water and dried over Na$_2$SO$_4$. After removing the solvent at reduced pressure, the residue was chromatographed on silica gel eluting with hexane:ethyl acetate (1:2) and recrystallized from benzene to give 162 mg (56.2% yield) of the titled compound, mp, 143–144° C.

Part P Preparation of (1-Benzyl-6-(3-carboxypropyloxy)-2-ethylindolizin-3-yl)glyoxylamide 11

A mixture of the ester (10, 125 mg, 0.286 m mol) in methanol (1.2 ml) and 10% aqueous lithium hydroxide (1.2 ml) was stirred at room temperature for 3 hours, acidified with dilute hydrochloric acid and extracted with dichloromethane. The extracts were washed with water and dried over Na$_2$SO$_4$. After removing the solvent at reduced pressure, the residue was chromatographed on silica gel eluting with chloroform:methanol (10:1) and recrystallized from ethyl acetate to give 58.4 mg (49.9% yield) of the titled compound, mp, 176–178° C.

Example 2

Part A: Preparation of Ethyl 3-(3-Benzyloxy-2-pyridinyl)propanoate 13

A mixture of (E)-ethyl 3-(3-benzyloxy-2-pyridinyl)propenoate (12, N. Desideri, A. Galli, I. Sestili, and M. L. Stein, Arch. Pharm. (Weinheim) 325, 29 (1992)) (12.2 g, 43.0 m mol) and 10% palladium-coal (0.5 g) in ethyl acetate (250 ml) was stirred in hydrogen atmosphere until no more starting material remained. The catalyst was filtered and the filtrate was concentrated under reduced pressure. The residue was chromatographed on silica gel eluting with hexane:AcOEt (2:1) and (1:2). The fraction of the laraer Rf value (6.0 g (48.8% yield)) was the titied compound.

Part B: Preparation of 3-(3-Hydroxy-2-pyridinyl)propanamide 15

A solution of the ester (14, 7.47 g) in 28% ammonium hydroxide (50 ml) was allowed to stand at room temperature overnight and the volatile materials were removed by distillation under reduced pressure. The residue was crystallized from ethyl acetate to give 6.49 g (94.7% yield) of the titled compound, mp, 130–134° C.

Part C: Preparation of 3-(3-Benzyloxy-2-pyridinyl)propanamide 16

A mixture of the hydroxy compound (15, 4.85 g, 29.2 m mol), benzyl chloride (4.06 g, 32.1 m mol) and potassium carbonate (8.07 g, 58.4 m mol) in methylethylketone (100 ml) was heated under reflux for 9 hours. The insoluble materials were removed by filtration. The filtrate was concentrated under reduced pressure. The residue was dissolved in dichloromethane. The solution was washed with water and dried over Na$_2$SO$_4$. After removing the solvent, the residue was crystalized from benzene to give 5.10 g (68.2% yield) of the titled compound, mp, 126–127° C.

Part D-1: Preparation of Ethyl 2-(8-Benzyloxy-2-ethylindolizin-1-yl)acetate 17a

A mixture of the ester (13, 1.0 g, 3.51 m mol), 1-bromo-2-butanone (0.79 g, 5.23 m mol) and sodium hydrogencarbonate (0.70 g, 8.23 m mol) in methylethylketone (10 ml) was heated under reflux for 20 hours. The solid was filtered off. After removing the solvent of the filtrate at reduced pressure, the residue was chromatographed on silica gel elutlng with hnexane:AcOEt (5:1) to give 283 mg (23.9% yield) of the titled compound as an oil.

¹H NMR (CDCl$_3$) δ 1.15 (3H, t, J=7.2 Hz), 1.25 (3H, t, J=7.5 Hz), 2.61 (2H, q, J=7.6 Hz), 3.97 (2H, s), 4.04 (2H, q, J=7.2 Hz), 5.11 (2H, s), 5.93 (1H, d, J=7.4 Hz), 6.23 (1H, t, J=7.0 Hz), 7.08 (1H, s), 7.3–7.5 (6H, m).

Part D-2: Preparation of 2-(8-Benzyloxy-2-ethylindolizin-1-yl)acetamide 17b and 2-(2-Ethyl-3-(2-oxobutyloxy)-indolizin-1-yl)acetamide 17c A mixture of the pyridine derivative (16, 4.00 g, 15.6 m mol), 1-bromo-2-butanone (3.53 g, 23.4 m mol) and sodium hydrogencarbonate (6.55 g, 78 m mol) in methylethylketone (30 ml) was heated under reflux for 60 hours. The solid was filtered off. The volatile materials were removed by distillation under reduced pressure. The residue was chromatographed on silica gel eluting with hexane:ethyl acetate (1:2) and with ethyl acetate. The first fraction was crystallized from benzene:hexane to give 2.32 g (48.2% yield) of the titled compound 17b and, mp, 117–119° C.

The second fraction was crystallized from AcOEt:hexane to give 0.208 g (4.6% yield) of the titled compound 17c and, mp, 156–157° C.

Part D-3: Preparation of 2-(8-Benzyloxy-2-cyclopropylindolizin-1-yl)acetamide 17d Chloroacetylcyclopropane was treated by the procedure described above and crystallized from benzene:hexane (30.8% yield), mp, 128–131° C.

Part E: General Procedure for Preparation of 3-(Substituted benzoyl)indolizine 18

The indolizine derivative (17, 1 eq) and substituted benzoylchloride (1.5 eq) in benzene was heated under reflux for 4 hours and washed with aqueous sodium hydrogencarbonate and dried over $Na_2SO_4$. After removing the solvent at reduced pressure, the residue was purified by recrystallization or column chromatography.

Other Preparations:

Ethyl 2-(8-benzyloxy-2-ethyl-3-(o-phenylbenzoyl)-indolizin-1-yl)acetate 18a. This was purified by column chromatography on silica gel eluting with hexane:AcOEt (5:1). 73.2% Yield. Amorphous solid.

2-(8-Benzyloxy-2-ethyl-3-(o-phenylbenzoyl)-indolizin-1-yl)acetamide 18b. This compound was purified by column chromatography on silica gel eluting with hexane:AcOEt (1:2). 71.3% Yield. Amorphous solid.

2-(8-Benzyloxy-3-(m-chlorobenzoyl)-2-ethyl-indolizin-1-yl)acetamide 18c. Mp, 239–240° C. (dec.) (Benzene). 96.2% Yield.

2-(3-(m-Chlorobenzoyl)-2-ethyl-8-(2-oxobutyloxy)-indolizin-1-yl)acetamide 18d Mp, 191–192° C. (AcOEt-benzene). 68.4% Yield.

2-(8-Benzyloxy-2-cyclopropyl-3-(o-phenylbenzoyl)-indolizin-1-yl)acetamide 18e. This compound was purified by column chromatography on silica gel eluting with hexane:AcOEt (1:2). 56.6% Yield. Amorphous solid.

Part F: General Procedure for Preparation of 3-(Substituted Benzyl)indolizine 19

Boron-t-butylamine complex (6 eq) was added in small portions to a mixture of pulverized aluminumchloride (3 eq) in dichloromethane with cooling in ice. After stirring for 10 min, the mixture became clean. A solution of the ketone (18, 1 eq) in dichloromethane was added dropwise to the solution. The reddish orange-coloured solution was stirred for 5 hours. Dilute hydrochloric acid was added dropwise. The organic phase was separated, washed with aqueous sodium hydrogencarbonate and water successively and dried over $Na_2SO_4$. After removing the solvent at reduced pressure, the residue was purified by chromatography or recrystallization.

Other Preparations:

2-(8-Benzyloxy-2-ethyl-3-(o-phenylbenzoyl)indolizin-3-yl)ethanol 19a

This was purified by silica gel column chromatography eluting with hexane:AcOEt (1:1). Viscous oil. 45.1% Yield.
$^1$H NMR (CDCl$_3$) δ 1.09 (3H, t, J=7.6 Hz), 2.61 (2H, q, J=7.5 Hz), 3.16 (2H, t, J=6.9 Hz), 3.73 (2H, q, J=6.3 Hz), 4.10 (2H, s), 5.11 (2H, s), 5.94 (1H, d, J=7.5 Hz), 6.16 (1H, t, J=7.2 Hz), 6.66 (1H, d, J=7.8 Hz), 6.91 (1H, d, J=7.2 Hz), 7.1–7.6 (13H, m).

2-(8-Benzyloxy-2-ethyl-3-(o-phenylbenzyl)-indolizin-1-yl)acetamide 19b. Mp, 134–136° C. (benzene-hexane). 59.7% Yield.

2-(3-(m-Chlorobenzyl)-2-ethyl-8-(2-hydroxybutyloxy)-indolizin-1-yl)acetamide 19c. Mp, 131° C. (benzene-hexane). 73.0% Yield.

2-(8-Benzyloxy-3-(m-chlorobenzyl)-2-ethyl-indolizin-1-yl)acetamide 19d. Mp, 167–168° C. (benzene-hexane). 69.7% Yield.

2-(8-Benzyloxy-2-cyclopropyl-3-(o-phenylbenzyl)-indolizin-1-yl)acetamide 19e. Mp, 208–210° C. (benzene). 37.9% Yield.

2-(3-Benzyl-8-benzyloxy-2-ethylindolizin-1-yl)acetamide 19f.

Mp, 174–176° C. (ether-hexane). 77.3% Yield.

2-(3-Naphthyl-8-benzyloxy-2-ethylindolizin-1-yl) acetamide 19g. Mp, 166–169° C. (dec.) (ether-hexane). 43.5% Yield.

Part I: General Procedure for Preparation of 8-Hydroxyindolizine Compounds 20

A mixture of the 8-benzyloxy-indolizine derivative (19) and 10% palladium-coal in ethyl acetate was stirred in hydrogen for 9 hours to 3 days.

Other Preparations:

2-(3-Benzyl-8-hydroxy-2-ethylindolizin-1-yl)acetamide 20v.

Mp, 138–141° C. (ether-hexane). 45% Yield.

2-(3-Naphthyl-8-hydroxy-2-ethylindolizin-1-yl)acetamide 20w.

30 Mp, 138–142° C. (ether-hexane-AcOEt). 32% Yield.

2-(2-Ethyl-8-hydroxy-3-(o-phenylbenzyl)-indolizin-1-yl) acetamide 20x. 59.6% Yield.

2-(3-(m-Chlorobenzyl)-2-ethyl-8-hydroxy-indolizin-1-yl) acetamide 20y. 58.3% Yield.

2-(2-Cyclopropyl-8-hydroxy-3-(o-phenylbenzyl)-indolizin-1-yl)acetamide 20z. 55.8% Yield.

Part H: General Procedure for Preparation of Indolizine-8-oxyacetate Compounds 21

60% Sodium hydride (1.5 eq) was added in small portions to a mixture of the 8-hydroxyindolizine compound (20, 1.0 eq) and benzyl, ethyl or methyl bromoacetate (3.0 eq) in dimethylformamide. The mixture was stirred at room temperature for 4–10 hours. Dilute hydrochloric acid was added. The mixture was extracted with ethyl acetate. The extracts were washed with water and dried over $Na_2SO_4$. After removing the solvent at reduced pressure, the residue was purified by chromatography.

Other Preparations:

Methyl (3-Benzyl-1-carbamoylmethyl-2-ethylindolizin-8-yloxy)acetate 21v

Mp, 159–163° C. (ether-hexane). 42.2% Yield. IR $v_{max}$ (nujol) 3402, 3166, 1731, 1678, 1649 cm$^{-1}$. $^1$H NMR (CDCl$_3$) δ 1.17 (3H, t, J=7.6 Hz), 2.79 (2H, q, J=7.6 Hz), 3.83 (3H, s), 3.99 (2H, s), 4.23 (2H, s), 4.72 (2H, s), 5.35 (1H, br.s), 5.82 (1H, d, J=7.0 Hz), 6.20 (1H, t, J=7.0 Hz), 6.44 (1H, br.s), 7.00–7.29 (6H, m). Analyses: Calcd. for $C_{22}H_{24}N_2O_4 \cdot 0.2H_2O$: C, 68.80; H, 6.40; N, 7.29. Found: C, 68.67; H, 6.40; N, 7.18.

Methyl (3-Naphthyl-1-carbamoylmethyl-2-ethylindolizin-8-yloxy)acetate 21w. Foam. 38% Yield. IR $v_{max}$ (CHCl$_3$) 3498, 3384, 1754, 1671, 1596 cm$^{-1}$.

2-(8-(Benzyloxycarbonylmethyloxy)-2-ethyl-3-(o-phenylbenzyl)indolizin-1-yl)acetamide 21x. 45.4% Yield.

2-(8-(Benzyloxycarbonylmethyloxy)-3-(m-chlorobenzyl)-2-ethylindolizin-1-yl)acetamide 21y. Mp, 157–158° C. (benzene). 38.8% Yield.

2-(8-(Carbomethoxymethyloxy)-2-cyclopropyl-3-(o-phenylbenzyl)-indolizin-1-yl)acetamide 21z. 43.8% Yield.

Part I: Preparation of Indolizine-8-oxyacetic Acid Compounds 22

A mixture of the benzyl ester (21) and 10% palladiumcoal in ethyl acetate was stirred in hydrogen for 3hours. The catalyst was filtered and washed well with ethyl acetate. The solvent of the filtrate was removed at reduced pressure and the residue was crystallized from ethyl acetate.

Other Preparations:
2 2-(3-Benzyl-8-(carboxymethyloxy)-2-ethylindolizin-1-yl)acetamide 22v Mp, 213–218° C. (dec.) (ether-hexane). 79% Yield. IR $v_{max}$ (nujol) 3418, 1735, 1718, 1638, 1618 cm$^{-1}$. $^1$H NMR (CDCl$_3$+CD$_3$OD=7:1) δ 1.16 (3H, t, J=7.7 Hz), 2.77 (2H, q, J=7.7 Hz), 3.99 (2H, s), 4.24 (2H, s), 4.69 (2H, s), 5.89 (1H, d, J=7.0 Hz), 6.23 (1H, t, J=7.0 Hz), 7.01–7.25 (6H, m). Analyses: Calcd. for C$_{21}$H$_{22}$N$_2$O$_4$ 0.2H$_2$O: C, 68.17; H, 6.10; N, 7.57. Found: C, 67.99; H, 6.07; N, 7.65.

2-(8-(Carboxymethyloxy)-2-ethyl-3-(1-naphthyl)indolizin-1-yl)acetamide 22w. Mp, 129–133° C. (hexane-AcOEt). 65% Yield.

Preparation of 2-(8-(Carboxymethyloxy)-2-ethyl-3-(o-phenylbenzyl)indolizin-1-yl)acetamide 22x. Mp, 164–165° C. (AcOEt). 61.1% Yield.

2-(8-(Carboxymethyloxy)-3-(m-chlorobenzyl)-2-ethylindolizin-1-yl)acetamide 22y. Mp, 216–219° C. (dec.) (AcOEt). 57.5% Yield.

2-(8-(Carboxymethyloxy)-2-cyclopropyl-3-(o-phenylbenzyl)-indolizin-1-yl)acetamide 22z. 65.5% Yield. $^1$H NMR (CDCl$_3$) δ 0.51 (2H, m), 0.89 (2H, m), 1.76 (1H, m), 4.06 (2H, s), 4.22 (2H, s), 4.63 (2H, s), 5.82 (1H, d, J=7.5 Hz), 6.16 (1H, t, J=7.2 Hz), 6.56 (1H, d, J=7.5 Hz), 6.88 (1H, d, J=7.2 Hz), 7.11 (1H, dt, J=7.5, 1.5 Hz), 7.26 (2H, m), 7.3–7.5 (5H, m).

Example 3
Part A: Preparation of Ethyl 3-Hydroxy-2-pyridineacetate 24

60% Sodium hydride (2.69 g, 66.2 m mol) was added in small portions to a solution of ethyl 3-hydroxy-2-pyridineacetate (23, 12.0 g, 66.2 m mol) (N. Desideri, F. Manna, M. L. Stein, G. Bile, W. Filippeelli, and E. Marmo. Eur. J. Med. Chem. Chim. Ther., 18, 295 (1983)) in dimethylformamide (220 ml) at 0° C. The mixture was stirred at 0° C. for 50 min. Benzyl chloride (8.4 ml, 72.8 m mol) was added dropwise to the mixture, which was stirred overnight. Ethyl acetate was added. The mixture was washed with 5% aqueous sodium hydrogencarbonate and water and dried over Na$_2$SO$_4$. After removing the solvent at reduced pressure, the residue was chromatographed on silica gel eluting with AcOEt:toluene (1:19 to 1:1) to give 16.17 g (90.0% yield) of the titled compound as an oil.

IR $v_{max}$ (film) 1736, 1446, 1278 cm$^{-1}$. $^1$H NMR (CDCl$_3$) δ 1.21 (3H, t, J=7.2 Hz), 3.93 (2H, s), 4.14 (2H, q, J=7.2 Hz), 5.10 (2H, s), 7.13–7.22 (2H, m), 7.32–7.43 (5H, m), 8.16 (1H, dd, J=4.0, 3.0 Hz). Analyses: Calc'd for C$_{16}$H$_{17}$NO$_3$: C, 70.83; H, 6.32; N, 5.16. Found: C, 70.65; H, 6.37; N, 5.20.

Part B: Preparation of Ethyl (8-Benzyloxy-2-ethylindolizin-1-yl)carboxylate 25a

A mixture of pyridine derivative (24, 15.15 g, 55.8 m mol) sodium hydrogencarbonate (23.45 g, 279 m mol) and 1-bromo-2-butanone (11.4 ml, 113 m mol) in methylethylketone (250 ml) was heated under reflux for 24 hour, washed with water and dried over Na$_2$SO$_4$. After removing the solvent at reduced pressure, The residue was chromatographed on silica gel eluting with AcOEt:hexane (1:19 to 1:9) to give 16.66 g, (92.0% yield) of the titled compound as an oil.

IR $v_{max}$ (film) 1690, 1227, 1092 cm$^{-1}$. $^1$H NMR (CDCl$_3$) δ 1.15 (3H, t, J=7.2 Hz), 1.26 (3H, t, J=7.5 Hz), 2.82 (2H, q, J=7.5 Hz), 4.11 (2H, q, J=7.2 Hz), 5.16 (2H, s), 6.22 (1H, d, J=7.6 Hz), 6.44 (1H, t, J=7.1 Hz), 7.07 (1H, s), 7.27–7.57 (6H, m). Analyses: Calc'd for C$_{20}$H$_{21}$NO$_3$ 0.1H$_2$O: C, 73.87; H, 6.57; N, 4.31. Found: C, 73.75; H, 6.66; N, 4.30.

Preparation of Ethyl (8-Benzyloxy-2-cyclopropylindolizin-1-yl)carboxylate 25b. 78% Yield.

Part C: General Procedure for Preparation of Ethyl (8-Benzyloxy-2-ethyl-3-(substituted benzoyl)indolizin-1-yl)carboxylate 26

A mixture of the indolizine (25, 1 eq), substituted benzoyl chloride (2.0 eq) and triethylamine (5.0 eq) was heated at 90° C. (bath temp.) for 2–8 hours. Ethyl acetate was added. The mixture was washed with dilute hydrochloric acid and water and dried over Na$_2$SO$_4$. After removing the solvent at reduced pressure, the residue was chromatographed on silica gel eluting with AcOEt:hexane (1:2) and recrystallized.

Other Preparations:
Ethyl (3-benzoyl-8-benzyloxy-2-ethylindolizin-1-yl)carboxylate 26a Mp, 124–125° C. (AcOEt-hexane). 79% Yield. Ethyl (8-benzyloxy-2-ethyl-3-(o-phenylbenzoyl)indolizin-1-yl)carboxylate 26b. Mp, 110–112° C. (ether-hexane). 46.0% Yield.

Ethyl (8-benzyloxy-3-(m-chlorobenzoyl)-2-ethylindolizin-1-yl)carboxylate 26c. Mp, 115.0–116.5° C. (ether-hexane). 92% Yield.

Ethyl (8-benzyloxy-2-ethyl-3-(m-trifluoromethylbenzoyl)indolizin-1-yl)carboxylate 26d. Mp, 129.0–129.5° C. (ether-hexane). 82% Yield.

Ethyl (8-benzyloxy-2-ethyl-3-(1-naphthoyl)indolizin-1-yl)carboxylate 26e. Mp, 169–170° C. (benzene-hexane). 59.3% Yield.

Ethyl (8-benzyloxy-2-cyclopropyl-3-(o-phenylbenzoyl)indolizin-1-yl)carboxylate 26f. Mp, 143–145° C. (AcOEt-hexane). 52% Yield.

Part D: General Procedure for Preparation of (8-Benzyloxy-2-ethyl-3-(substituted benzoyl)indolizin-1-yl)carboxylic Acid and 8-Benzyloxy-2-ethyl-3-(substituted benzoyl) indolizine 27

To a solution of the ester (26, 1.0 m mol) in dimethylsulfoxide (10 ml), 50% aqueous potassium hydroxide (3 ml) was added. The mixture was heated at 140° C. for 2–24 hours. After cooling, the mixture was acidified with dilute hydrochloric acid and extracted with ethyl acetate. The extracts were washed with water dried over Na$_2$SO$_4$. After removing the solvent under reduced pressure, the residue was purified by recrystallization to give the carboxylic acid. The acid in toluene was heated under reflux for 1 hour and the solvent was removed by distillation at reduced pressure. The residue was purified by recrystallization to give 27.

Other Preparations:
3-Benzoyl-8-benzyloxy-2-ethyl-indolizine 27a

Mp, 92–93° C. (AcOEt-hexane). IR $v_{max}$ (KBr) 2965, 1593, 1571, 1552, 1326, 1275, 1045 cm$^{-1}$. $^1$H NMR (CDCl$_3$) δ 1.05 (3H, t, J=7.4 Hz), 2.42 (2H, q, J=7.4 Hz), 5.21 (2H., s), 6.47 (1H, d, J=7.4 Hz), 6.62–6.71 (2H, m), 7.25–7.52 (8H, m), 7.61–7.65 (2H, m), 9.23 (1H, d, J=7.2 Hz). [EIMS] m/z 355 [M+]. Analyses: Calc'd for C$_{24}$H$_{21}$NO$_2$ 0.1H$_2$O: C, 80.69; H, 5.98; N, 3.92. Found: C, 80.67; H, 5.98; N, 3.92.

8-Benzyloxy-2-ethyl-3-(o-phenylbenzoyl)indolizine 27b

Quantitative yield. IR $v_{max}$ (nujol) 1735, 1597, 742 cm$^{-1}$.

8-Benzyloxy-3-(m-chlorobenzoyl)-2-ethyl-indolizine 27c

Mp, 95.5–96.5° C. (ether-hexane). 87% Yield.

8-Benzyloxy-2-ethyl-3-(m-trifluoromethylbenzoyl) indolizine 27d. Mp, 97–98° C. (ether-hexane). 84% Yield.

8-Benzyloxy-2-ethyl-3-(1-naphthoyl)indolizine 27e. 66.1% Yield.

8-Benzyloxy-2-cyclopropyl-3-(o-phenylbenzoyl)indolizine 27f 82% Yield.

Part E: General Procedure for Preparation of 8-Benzyloxy-2-ethyl-3-(substituted benzyl)indolizine 28

Compound 27 was treated by the procedure described for the preparation of 4.

Other Preparations:

3-Benzyl-8-benzyloxy-2-ethyl-indolizine 28a. $^1$H NMR (CDCl$_3$) δ 1.28 (3H, t, J=7.4 Hz), 2.71 (2H, q, J=7.4 Hz), 4.22 (2H, s), 5.16 (2H, s), 5.99 (1H, d, J=7.4 Hz), 6.24 (1H, dd, J=7.4, 7.4 Hz), 6.61 (1H, s), 7.02–7.51 (11H, m).

8-Benzyloxy-2-ethyl-3-(o-phenylbenzyl)indolizine 28b Quantitative yield. IR $v_{max}$ (CHCl$_3$) 1525, 1259 cm$^{-1}$.

8-Benzyloxy-3-(m-chlorobenzyl)-2-ethyl-indolizine 28c. Quantitative yield. IR $v_{max}$ (CHCl$_3$) 1551, 1258 cm$^{-1}$.

8-Benzyloxy-2-ethyl-3-(m-trifluoromethylbenzyl)indolizine 28d. Mp, 73–75° C. (hexane). Quantitative yield. IR $v_{max}$ (nujol) 1332, 1163, 1114 cm$^{-1}$.

(8-Benzyloxy-2-ethyl-3-(1-naphthylmethyl)indolizin-1-yl) carboxylate 28e. Mp, 119–120° C. (hexane). 89.0% Yield.

8-Benzyloxy-2-cyclopropyl-3-(o-phenylbenzyl)indolizine 28f 91% Yield. IR $v_{max}$ (CHCl$_3$) 1527, 1448, 1259 cm$^{-1}$.

Part F: General Procedure for Preparation of Ethyl (3-Benzyl-2-methylindolizin-1-yl)carboxylate 31a, Ethyl (3-Benzyl-8-benzyloxy-2-methylindolizin-1-yl)carboxylate 31b and Ethyl (3-Benzyl-8-methoxy-2-methylindolizin-1-yl)carboxylate 31c.

A mixture of 3-bromo-4-phenyl-butan-2-one (29, F. Bellesia, F. Ghelfi, K. Grandi and M. Ugo, J. Chem. Res. (S), S 428 (1986)) (1.3 eq) and ethyl pyridine-2-acetate or its 3-substituted compounds (1.0 eq) and sodium hydrogencarbonate (10 eq) were heated at 165° C. for 1 to 4 hours and chromatographed on silica gel eluting with hexane:AcOEt (5–2:1).

Other Preparations:

Ethyl (3-benzyl-2-methylindolizin-1-yl)carboxylate 31a Mp, 75° C. (hexane). 37.1% Yield.

Ethyl (3-benzyl-8-benzyloxy-2-methylindolizin-1-yl) carboxylate 31b. Mp, 117–118° C. (hexane). 47.4% Yield.

Ethyl (3-benzyl-8-methoxy-2-methylindolizin-1-yl) carboxylate 31c. Mp, 105° C. (hexane). 23.4% Yield.

Part G: General Procedure for Preparation of (3-Benzyl-2-methylindolizin-1-yl)carboxylic Acid 32a and (3-Benzyl-8-benzyloxy-2-methylindolizin-1-yl)carboxylic Acid 32b The ester 31 (2 m mol) was dissolved in a solution of KOH (0.5 g) in water (5 ml) and dimethylsulfoxide (5 ml). The solution was heated at 140° C. (bath temp.) for 5 hours. Ice-water was added. The mixture was washed with ether, acidified with dilute hydrochloric acid and extracted with ethyl acetate. The extracts were washed with water and dried over Na$_2$SO$_4$. After removing the solvent at reduced pressure, the residue was crystallized from AcOEt.

Other Preparations:

(3-Benzyl-2-methylindolizin-1-yl)carboxylic acid 32a Mp, 182–183° C. (dec.). 60.3% Yield.

(3-Benzyl-8-benzyloxy-2-methylindolizin-1-yl)carboxylic acid 32b. Mp, 132° C. (dec.). 68.4% Yield.

Part H: General Procedure for Preparation of 3-Benzyl-2-methylindolizine 33a and 3-Benzyl-8-benzyloxy-2-methylindolizine 33b A mixture of the carboxylic acid in xylene was heated under reflux for 2 hours. After removing the solvent at reduced pressure, the residue was crystallized or used to the next preparation.

Preparation of 3-Benzyl-2-methylindolizine 33a

Mp, 96–97 0C. Quantitative yield.

Preparation of 3-Benzyl-8-benzyloxy-2-methylindolizine 33b

Quantitative yield. $^1$H NMR (CDCl$_3$) δ 2.34 (3H, s), 4.22 (2H, s), 5.17 (2H, s) 6.00 (1H, d, J=7.6 Hz), 6.25 (1H, t, J=7.1 Hz), 6.56 (1H, s), 7.0–7.5 (11H, m).

Part J: General Procedure for Preparation of (Indolizin-1-yl)glyoxylamide 34 and 35a-k These compounds were prepared according to the procedure described for the synthesis of compound 8 from compound 4.

Preparation of (3-Benzyl-2-methylindolizin-1-yl)glyoxylamide 34

Mp, 198–199° C. (benzene). 49.3% Yield.

(3-Benzyl-8-benzyloxy-2-ethylindolizin-1-yl)glyoxylamide 35a.

Mp, 188–189° C. 63% Yield.

Other Preparations:

(3-Benzyl-8-benzyloxy-2-ethylindolizin-1-yl)glyoxyl-N-methylamide 35b. Mp, 190–191° C. 80% Yield.

(3-Benzyl-8-benzyloxy-2-ethylindolizin-1-yl)glyoxyl-N,N-dimethylamide 35c. Mp, 199–200° C. (AcOEt). 43% Yield.

(8-Benzyloxy-2-ethyl-3-(o-phenylbenzyl)indolizin-1-yl) glyoxylamide 35d. Mp, 183–185° C. (ether-hexane). 79.0% Yield.

(8-Benzyloxy-2-ethyl-3-(o-phenylbenzyl)indolizin-1-yl) glyoxyl-N-methylamide 35e. Mp, 200–201° C. (ether-hexane). 71% Yield.

(8-Benzyloxy-2-ethyl-3-(o-phenylbenzyl)indolizin-1-yl) glyoxyl-N,N-dimethylamide 35f. Mp, 201–202° C. (ether-hexane). 88% Yield.

(3-Benzyl-8-benzyloxy-2-methylindolizin-1-yl) glyoxylamide 35g. Mp, 212–214° C. 96.2% Yield. IR $v_{max}$ (nujol) 3472, 3197, 1678, 1627 cm$^{-1}$. $^1$H NMR (CDCl$_3$) δ 2.44 (3H, s), 4.21 (2H, s), 4.75 (1H, br.s), 5.13 (2H, s), 6.14 (1H, br.s) 6.39 (1H, d, J=7.4 Hz), 6.51 (1H, t, J=7.3 Hz), 7.05–7.15 (2H, m), 7.20–7.5 (9H, m). Analyses: Calc'd for C$_{25}$H$_{22}$N$_2$O$_3$: C, 75.36; H, 5.57; N, 7.03. Found: C, 75.12; H, 5.66; N, 7.06.

(8-Benzyloxy-3-(m-chlorobenzyl)-2-ethylindolizin-1-yl) glyoxylamide 35h. Mp, 145–148° C. (ether-hexane). 80% Yield.

(8-Benzyloxy-2-ethyl-3-(m-trlfluoromethylbenzyl) indolizin-1-yl)glyoxylamide 35i. Mp, 182–185° C. (CH$_2$Cl$_2$-hexane). 76% Yield.

(8-Benzyloxy-2-ethyl-3-(l-naphthylmethyl)indolizin-1-yl) glyoxylamide 35j. Mp, 189–190° C. (benzene). 76.0% Yield.

(8-Benzyloxy-2-cyclopropyl-3-(o-phenylbenzyl)indolizin-1-yl)glyoxylamide 35k. Mp, 185–186° C. (CH$_2$Cl$_2$-hexane). Quantitative yield.

Part K: General Procedure for Preparation of (8-Hydroxyindolizin-1-yl)glyoxylamide 36a,d-k These compounds were prepared according to the procedure described for the synthesis of compound 20 from 19.

Other Preparations:

(3-Benzyl-2-ethyl-8-hydroxyindolizin-1-yl)glyoxylamide 36a.

Mp, 194–195° C. (AcOEt).

Other Preparations (2-Ethyl-8-hydroxy-3-(o-phenylbenzyl)indolizin-1-yl) glyoxylamide 36d. Mp, 195–196° C. (dec.) (ether-hexane). 95.0% Yield.

(2-Ethyl-8-hydroxy-3-(o-phenylbenzyl)indolizin-1-yl) glyoxyl-N-methylamide 36e. Mp, 186–189° C. (ether-hexane). 89% Yield.

(2-Ethyl-8-hydroxy-3-(o-phenylbenzyl)indolizin-1-yl) glyoxyl-N,N-dimethylamide 36f. Mp, 177–180° C. (ether-hexane). 95% Yield.

(3-Benzyl-8-hydroxy-2-methylindolizin-1-yl)glyoxylamide 36g.

Mp, 189–192° C. 94.9% Yield.

(3-(m-Chlorobenzyl)-2-ethyl-8-hydroxyindolizin-1-yl) glyoxylamide 36h. Mp, 144–146° C. (AcOEt-hexane). 88% Yield.

(2-Ethyl-8-hydroxy-3-(m-trifluoromethylbenzyl)indolizin-1-yl)glyoxylamide 36i. Mp, 142–146° C. (AcOEt-hexane). 96% Yield.

(2-Ethyl-8-hydroxy-3-(1-naphthylmethyl)indolizin-1-yl)glyoxylamide 36j. Mp, 176–178° C. (benzene). 84.5% Yield.

(2-Cyclopropyl-8-hydroxy-3-(o-phenylbenzyl)indolizin-1-yl)glyoxylamide 36k. Mp, 189–191° C. (AcOEt-hexane). 95% Yield.

Part L: General Procedure for Preparation of (8-(Carboalkoxymethyloxy)indolizin-1-yl)glyoxylamide 37a-d,f,g-j, 38a and 39d,i,k These compounds were prepared according to the procedure described for the synthesis of compound 21 from 20.

Other Preparations:

(3-Benzyl-8-(carbethoxymethyloxy)-2-ethylindolizin-1-yl)glyoxylamide 37a

Mp, 191–192° C. (AcOEt-hexane). 23% Yield.

(3-Benzyl-8-(carbethoxymethyloxy)-2-ethylindolizin-1-yl)glyoxyl-N-methylamide 37b. Mp, 197–198° C. (AcOEt-hexane). 72% Yield.

(3-Benzyl-8-(carbethoxymethyloxy)-2-ethylindolizin-1-yl)glyoxyl-N,N-dimethylamide 37c. Mp, 140–141° C. (AcOEt-hexane). 39% Yield.

(8-(Carbethoxymethyloxy)-2-ethyl-3-(o-phenylbenzyl)indolizin-1-yl)glyoxylamide 37d. Mp, 127–129° C. (ether-hexane). 86.0% Yield.

(8-(Carbethoxymethyloxy)-2-ethyl-3-(o-phenylbenzyl)indolizin-1-yl)glyoxyl-N,N-dimethylamide 37f. Mp, 109.5–110.0° C. (ether-hexane). 79% Yield.

(3-Benzyl-8-(carbethoxymethyloxy)-2-methylindolizin-1-yl)glyoxylamide 37g. Mp, 193–195° C. 41.4% Yield.

(8-(Carbethoxymethyloxy)-3-(m-chlorobenzyl)-2-ethylindolizin-1-yl)glyoxylamide 37h. Mp, 172–175° C. (AcOEt-hexane). 73% Yield.

(8-Carbethoxymethyloxy-2-ethyl-3-(1-naphthylmethyl)indolizin-1-yl)glyoxylamide 37j. 37.8% Yield. IR $v_{max}$ (CHCl$_3$) 3513, 3400, 1761, 1698, 1638, 1497 cm$^{-1}$.

(3-Benzyl-8-(t-butoxycarbonylmethyloxy)-2-ethylindolizin-1-yl)glyoxylamide 38a. Mp, 161–162° C.

(8-(Carbomethoxymethyloxy)-2-ethyl-3-(o-phenylbenzyl)indolizin-1-yl)glyoxylamide 39d. Mp, 73–75° C. (dec.) (ether-hexane). 84% Yield.

(8-(Carbmethoxymethyloxy)-2-ethyl-3-(m-trifluoromethylbenzyl)indolizin-1-yl)glyoxylamide 39i. Mp, 136–137° C. (AcOEt-hexane). 59% Yield.

(8-(Carbmethoxymethyloxy)-2-cyclopropyl-3-(o-phenylbenzyl)indolizin-1-yl)glyoxylamide 39k. Mp, 178–179° C. (AcOEt-hexane). 69% Yield.

Part M: General Procedure for Preparation of (8-(Carboxymethyloxy)indolizin-1-yl)glyoxylamide 40a-d,f, g-k 1N-Aqueous potassium hydroxide (4 ml) was added to a solution of the ester (37–39, 2 m mol) in methanol (21 ml). The solution was stirred at room temperature for 40 min, washed with ether, acidified with 2N-HCl and extracted with ethyl acetate. The extracts were washed with water and dried over Na$_2$SO$_4$. After removing the solvent at reduced pressure, the residue was recrystallized.

Other Preparations:

(3-Benzyl-8-(carboxymethyloxy)-2-ethylindolizin-1-yl)glyoxylamide 40a

Mp, 244–245° C. (AcOEt-ether). 42% Yield. IR $v_{max}$ (KBr) 3855, 2974, 2931, 1703, 1660, 1625, 1312, 1092 cm$^{-1}$. $^1$H NMR (CDCl$_3$+CD$_3$OD) δ 1.22 (3H, t, J=7.4 Hz), 2.90 (2H, q, J=7.4 Hz), 4.27 (2H, s), 4.73 (2H, s), 6.37 (1H, d, J=7.8 Hz), 6.73 (1H, dd, J=6.6, 7.8 Hz), 7.06–7.43 (6H, m). [EIMS] m/z 380 [M+]. Analyses: Calc'd for C$_{21}$H$_{20}$N$_2$O$_5$ 0.7H$_2$O: C, 64.18; H, 5.49; N, 7.13. Found: C, 64.26; H, 5.27; N, 7.05.

(3-Benzyl-8-(carboxymethyloxy)-2-ethylindolizin-1-yl)glyoxyl-N-methylamide 40b. Mp, 212–213° C. (AcOEt). 47% Yield. (3-Benzyl-8-(carboxymethyloxy)-2-ethylindolizin-1-yl)glyoxyl-N,N-dimethylamide 40c. Mp, 166–167° C. (AcOEt). 49% Yield.

(8-(Carboxymethyloxy)-2-ethyl-3-(o-phenylbenzyl)indolizin-1-yl)glyoxylamide 40d. Mp, 209–212° C. (dec.) (ether-hexane). 93% Yield. IR $v_{max}$ (nujol) 3316, 1704, 1601, 1493 cm$^{-1}$. $^1$H NMR (d$_6$-DMSO) δ 1.01 (3H, t, J=7.5 Hz), 2.67 (2H, q, J=7.5 Hz), 4.18 (2H, s), 4.71 (2H, s), 6.41 (1H, d, J=7.8 Hz), 6.57–6.59 (2H, m), 7.14–7.57 (10H, m), 7.34 (1H, s), 13.09 (1H, br.s). Analyses: Calc'd for C$_{27}$H$_{24}$N$_2$O$_5$ 0.3H$_2$O: C, 70.21; H, 5.37; N, 6.06. Found: C, 70.17; H, 5.35; N, 5.98.

(8-(Carboxymethyloxy)-2-ethyl-3-(o-phenylbenzyl)indolizin-1-yl)glyoxyl-N,N-dimethylamide 40f. Mp, 208–209° C. (ether-hexane). 93% Yield.

(3-Benzyl-8-(carboxymethyloxy)-2-methylindolizin-1-yl)glyoxylamide 40g. Mp, 245–246° C. (dec.). 86.7% Yield. IR $v_{max}$ (nujol) 3417, 1736, 1650, 1629, 1495 cm$^{-1}$. $^1$H NMR (CDCl$_3$+CD$_3$OD) δ 2.47 (3H, s), 4.24 (2H, s), 4.73 (2H, s), 6.38 (1H, d, J=7.5 Hz), 6.59 (1H, t, J=7.2 Hz), 7.10 (2H, m), 7.2–7.3 (3H, m), 7.44 (1H, d, J=6.9 Hz). Analyses: Calc'd for C$_{20}$H$_{18}$N$_2$O$_5$ 0.2H$_2$O: C, 64.93; H, 5.01; N, 7.57. Found: C, 64.87; H, 5.02; N, 7.56.

(8-(Carboxymethyloxy)-3-(m-chlorobenzyl)-2-ethylindolizin-1-yl)glyoxylamide 40h. Mp, 230–233° C. (dec.) (ether-hexane). 79% Yield.

(8-(Carboxymethyloxy)-2-ethyl-3-(m-trifluoromethylbenzyl)indolizin-1-yl)glyoxylamide 40i Mp, 235–237° C. (dec.) (CH$_2$Cl$_2$-hexane). 97% Yield.

(8-Carboxymethyloxy-2-ethyl-3-(1-naphthylmethyl)indolizin-1-yl)glyoxylamide 40j. 68.4% Yield. IR $v_{max}$ (nujol) 3429, 3338, 1730, 1649, 1612, 1588, 1493 cm$^{-1}$.

(8-(Carboxymethyloxy)-2-cyclopropyl-3-(o-phenylbenzyl)indolizin-1-yl)glyoxylamide 40k. Mp, 205–207° C. (dec.) (AcOEt-hexane). 93% Yield.

Example 4

Part A: Preparation of (8-(Cyanomethyloxy)-2-ethyl-3-(1-naphthylmethyl)indolizin-1-yl)glyoxylamide 41

The hydroxy compound (36h) was treated with bromoacetonitrile by the procedure cited for the synthesis of 37 from 36. Mp, 212–215° C. (ether). 45% Yield. IR $v_{max}$ (nujol) 3484, 3226, 1659, 1629, 1497, 1305, 755 cm$^1$. $^1$H NMR (d$_6$-DMSO) δ 1.08 (3H, t, J=7.1 Hz), 2.80 (2H, q, J=7.2 Hz), 4.36 (2H, s), 5.18 (2H, s), 6.74 –6.85 (2H, m), 7.01 (1H, d, J=6.9 Hz), 7.21 (1H, s), 7.23–7.39 (3H, m), 7.78 (1H, s), 7.83 (1H, d, J=6.3 Hz). Analyses: Calc'd for C$_{21}$H$_{18}$N$_3$O$_3$Cl: C, 63.72; H, 4.58; N, 10.62; Cl, 8.96. Found: C, 63.54; H, 4.69; N, 10.79; Cl, 8.69.

Part B: Preparation of (8-(1H-Tetrazol-5-yl Methyloxy)-2-ethyl-3-(1-naphthylmethyl)indolizin-1-yl)glyoxylamide 42

A mixture of the nitrile derivative (41, 100 mg, 0.253 m mol) and trimethyltinazide (68 mg, 0.329 m mol) in toluene (2.5 ml) was heated under reflux for 23 hours. The precipitate was collected by filtration and suspended in toluene (2 ml). Hydrogen chloride gas was introduced. The mixture was stirred at room temperature for 20 min and then concentrated at reduced pressure. Ethyl acetate was added. The mixture was extracted with 1N-potassium hydroxide. The aqueous phase was washed with dichloromethane, acidified with dilute hydrochloric acid and extracted with ethyl acetate. The extracts were washed with water and dried over Na$_2$SO$_4$. After removing the solvent at reduced pressure, the residue was dissolved in ether. The insoluble materials were removed by filtration and hexane was added to the filtrate to give 25 mg (23% yield) of the titled compound, mp, 140–143° C. (dec.) (ether-hexane).

IR $v_{max}$ (nujol) 3468, 3222, 3153, 1718, 1651, 1612, 1594, 1489 cm$^{-1}$. $^1$H NMR (CDCl$_3$) δ 1.23 (3H, t, J=7.5 Hz), 2.88 (2H, q, J=7.5 Hz), 4.22 (2H, s), 5.65 (2H, s), 6.04 (1H, s), 6.29 (1H, d, J=7.8 Hz), 6.50 (1H, t, J=7.2 Hz), 6.92 (1H, br.s), 7.06–7.37 (5H, m).

Example 5

Part A: Preparation of 3-Benzyloxy-2-methylpyridine 44a

A mixture of 2-methyl-3-pyridinol (43, 16.4 g, 0.15 mol), pulverized potassium hydroxide (12.72 g, 0.195 mol), tetrabutylammonium bromide (2.42 g, 7.5 m mol) and benzyl bromide (18.7 ml, 0.158 mol) in tetrahydrofuran (380 ml) was stirred at room temperature for 1.5 hours. Water (38 ml) was added. The mixture was concentrated at reduced pressure and then extracted with ethyl acetate. The extracts were washed with water and dried (Na$_2$SO$_4$). After removing the solvent at reduced pressure, 28.3 g (90% yield) of the titled compound was obtained.

$^1$H NMR (CDCl$_3$) δ 2.56 (3H, s), 5.11 (2H, s), 7.04–7.16 (2H, m), 7.35–7.45 (5H, m), 8.08 (1H, dd, J=4.5, 1.5 Hz).

Part B: Preparation of 3-Methoxy-2-methyl-1-(2-oxobutyl)-pyridinium Bromide 45b

A mixture of 3-methoxypicoline (J. Yorgensen, H. C. Nielsen, N. Malhotra and J. Becher, J. Heterocyclic Chem., 29, 1841 (1992) (343 mg, 2.78 m mole) and 1-bromo-2-butanone (504 mg, 3.34 m mole) was heated at 70° C. for 10 min. The solid was washed with ethyl acetate to give a hygroscopic solid 711 mg (93.8%). Mp, 157–158° C.

Part C-1: Preparation of 8-Benzyloxy-2-ethylindolizine 46a

A mixture of 3-benzyloxy-2-methylpyridine (44a, 29.7 g, 0.149 mol) in ethyl acetate (17 ml) and 1-bromo-2-butanone (22.5 g, 0.149 mol) was stirred at 70° C. for 0.5 hours. Ethyl acetate (23 ml) was added to the reaction mixture and the solid was recrystallized from ethyl acetate to give 47.04 g (90.1%) of 45a. Quaternary salt 45a (47.04 g, 0.134 mol) in benzene (150 ml) and DBU (44.2 ml, 0.295 mol) were refluxed for 0.75 hours, poured into ice-water and extracted with ethyl acetate. The extracts were washed with water and dried (Na$_2$SO$_4$). After removing the solvent at reduced pressure, the titled oily compound 46a, 26.62 g (79% yield) was obtained. $^1$H NMR (CDCl$_3$) δ 1.28 (3H, t, J=7.6 Hz), 2.70 (2H, q, J=7.6 Hz), 5.16 (2H, s), 5.99 (1H, d, J=7.5 Hz), 6.29 (1H, t, J=7.1 Hz), 6.48 (1H, s), 7.10–7.52 (7H, m).

Compounds 46b-e were prepared according to the procedure cited above.

Part C-2: Preparation of 2-Ethyl-8-methoxy-indolizine 46b

A solution of 1, 8-diazabicyclo[5.4.0]-7-undecene (DBU) (341 mg, 2.24 m mole) in benzene (1 ml) was added to a mixture of the salt (45b, 277 mg, 1.02 m mole) in benzene (4 ml). The mixture was heated under reflux for 3 hours in nitrogen. After cooling, the mixture was filtered and washed with benzene. The filtrate was concentrated under reduced pressure to give an oil 178 mg (quantitative yield). $^1$H NMR (CDCl$_3$) d 1.28 (3H, t, J=7.5 Hz), 2.70 (2H, q, J=7.5 Hz), 3.91 (3H, s), 5.93 (1H, d, J=7.2 Hz), 6.32 (1H, t, J=7.0 Hz), 6.40 (1H, s), 7.10 (1H, s), 7.50 (1H, d, J=6.8 Hz).

Other Preparations:

8-Benzyloxy-2-methylindolizine 46c

92% Yield. Oil. $^1$H NMR (CDCl$_3$) δ 2.31 (3H, s), 5.16 (2H, s), 5.98 (1H, d, J=7.6 Hz), 6.28 (1H, t, J=7.0 Hz), 6.44 (1H, s), 7.08 (1H, s), 7.34–7.55 (6H, m).

2-Cyclopropyl-8-methoxyindolizine 46d

72% Yield. $^1$H NMR (CDCl$_3$) δ 0.60–0.68 (2H, m), 0.86–0.96 (2H, m), 1.83–1.97 (1H, m), 3.89 (3H, s), 5.92 (1H, d, J=7.4 Hz), 6.25–6.34 (1H+1H, m), 7.11 (1H, d, J=1.6 Hz), 7.47 (1H, d, J=7.0 Hz).

8-Benzyloxy-2-cyclopropylindolizine 46e

69% Yield. $^1$H NMR (CDCl$_3$) δ 0.61–0.69 (2H, m), 0.86–0.96 (2H, m), 1.84–1.97 (1H, m), 5.15 (2H, s), 5.98 (1H, d, J=7.6 Hz), 6.25–6.32 (1H+1H, m), 7.12 (1H, d, J=2.0 Hz), 7.35–7.49 (6H, m).

Part D: General Procedure for Preparation of 8-Benzyloxy-2-ethyl-3-(substituted carbonyl)indolizine 47

This compound was prepared from 46, according to the procedure described for the preparation of 18 from 17.

Other Preparations:

8-Benzyloxy-2-ethyl-3-(p-phenylbenzoyl)indolizine 47a
Mp, 114–115° C. 80% Yield.

8-Benzyloxy-3-cyclohexylcarbonyl-2-ethylindolizine 47b.
Mp, 88–89 C, (Hexane-EtOAc). 77% Yield.

8-Benzyloxy-3-cyclopentylcarbonyl-2-ethylindolizine 47c.
Mp, 63–64 C, (Hexane). 68% Yield.

8-Benzyloxy-3-cycloheptylcarbonyl-2-ethylindolizine 47d.
Mp, 85–86 C, (Hexane). 74% Yield.

8-Benzyloxy-2-ethyl-3-(2-oxopentyl)indolizine 47e. Mp, 84 C, (Hexane-EtOAc). 89% Yield.

8-Benzyloxy-2-ethyl-3-(1-oxo-2-propylpentyl)indolizine 47f.
Mp, 137–138° C. (hexane-EtOAc). 25% Yield.

8-Benzyloxy-2-ethyl-3-(naphth-2-ylcarbonyl)indolizine 47g. 70% Yield.

8-Benzyloxy-3-(3,5-di-t-butyl)benzoyl-2-ethylindolizine 47h.
Mp, 131° C. (Hexane:EtOAc). 82% Yield.

8-Benzyloxy-2-ethyl-3-(1-oxo-2-phenylethyl)indolizine 47i.
Mp, 139–140° C. (Hexane:EtOAc). 58% Yield.

3-(o-Benzylbenzoyl)-8-benzyloxy-2-ethylindolizine 47j
Yellow oil 58% Yield. IR $v_{max}$ (neat) 2964, 1590, 1548, 1438, 1302 cm$^{-1}$.

8-Benzyloxy-2-ethyl-3-(thiophen-2-yl)indolizine 47k. Mp, 141–142° C. (Hexane/EtOAc). 82% Yield.

Other Preparations:

8-Benzyloxy-2-ethyl-3-(3-(thiophen-2-yl)thiophen-2-yl)lindolizine 47l 3-(Thiophen-2-yl)thiophene-2-carboxylic acid was prepared by hydrolysis of the methyl ester (Y. Hamanaka, S, Fukushima and T. Hiyama, Heterocycles, 30, 303 (1990)). Mp, 137–138° C. (Hexane:EtOAc). $^1$H NMR (CDCl$_3$) δ 7.10 (1H, dd, J=3.6, 5.0 Hz), 7.26 (1H, d, J=5.0 Hz), 7.39 (1H, dd, J=1.0, 5.0 Hz), 7.55–7.60 (2H, m). IR $v_{max}$ (KBr) 2845, 2606, 1671, 1273, 1245 cm$^{-1}$. Analyses: Calc'd for C$_9$H$_6$O$_2$S: C, 51.41; H, 2.88; N, 30.50. Found: C, 51.39; H, 3.06; N, 30.24.

The acid chloride was treated as above but the product could not be purified and used to the next preparation without further purification.

8-Benzyloxy-2-ethyl-3-(m-methoxybenzoyl)indolizine 47m. Mp, 64–67° C. 77% Yield.

8-Benzyloxy-2-ethyl-3-(1-oxo-2-(4-n-pentylcyclohexyl)ethyl)indolizine 47o. Mp, 64–65° C. (Hexane). 41% Yield.

8-Benzyloxy-2-methy-3-(o-phenylbenzoyl)lindolizine 47q. Mp, 114–116 0C. 66.9% Yield.

8-Benzyloxy-3-benzoyl-2-cyclopropylindolizine 47r. Mp, 144–146° C. 81.4% Yield. 3-(p-n-Butylbenzoyl)-2-ethyl-8-methoxyindolizine 47s. Mp, 90–91° C., (hexane). 72.8% Yield.

8-Benzyloxy-2-methyl-3-(1-oxo-2-cyclohexylethyl)lindolizine 47t. Mp, 105–106° C. (Hexane:EtOAc). 61% Yield.

3-Cyclohexylcarbonyl-2-cyclopropyl-8-methoxy-indolizine 47u.
Mp, 122–123° C. 38.9% Yield.

8-Benzyloxy-3-cyclopentylcarbonyl-2-methylindolizine 47w
Mp, 93.5–94.5° C. 24% Yield.

Part E: Preparation of 8-Benzyloxy-3-(substituted methyl)-2-ethylindolizine 48
General procedure 1)
These compound were prepared from 47, according to the procedure described for the preparation of 28 from 27.
General procedure 2)
A mixture of 47, sodium borohydride (5eq. mol), pulverized aluminum trichloride (3 eq. mol) in tetrahydrofuran was heated under reflux for 45 min. Ice-water was added. The mixture was extracted with ethyl acetate. The extracts were washed with water and dried ($Na_2SO_4$). After removing the solvent at reduced pressure, the residue was purified by recrystallization or column chromatography.

Other Preparations:

8-Benzyloxy-2-ethyl-3-(p-phenylbenzyl)indolizine 48a
Quantitative vield. $^1$H NMR ($CDCl_3$) δ 1.26 (3H, t, J=7.2 Hz), 2.74 (2H, q, J=7.8 Hz), 4.28 (2H, s), 5.18 (2H, s), 6.02 (1H, d, J=7.2 Hz), 6.28 (1H, t, J=7.2 Hz), 7.11 (1H, d, J=8.4 Hz), 7.23–7.71 (14H, m).

8-Benzyloxy-3-cyclopentylmethyl-2-ethylindolizine 48c.
$^1$H NMR ($CDCl_3$) δ 1.15–1.34 (5H, m), 1.41–1.74 (6H, m), 2.18 (1H, quint, J=7.8 Hz), 2.65 (2H, q, J=7.4 Hz), 2.82 (2H, d, J=7.2 Hz), 5.17 (2H, s), 5.98 (1H, d, J=7.0 Hz), 6.34 (1H, dd, J=7.0, 7.4 Hz), 6.53 (1H, s), 7.3–7.5 (6H, m).

8-Benzyloxy-2-ethyl-3-pentylindolizine 48e
IR $\nu_{max}$ (KBr) 2950, 2920, 1550, 1520, 1365, 1250 $cm^{-1}$.

8-Benzyloxy-2-ethyl-3-(2-propylpentyl)indolizine 48f. 25% Yield.

8-Benzyloxy-2-ethyl-3-(naphth-2-ylmethyl)indolizine 48g.

8-Benzyloxy-3-(o-benzylbenzyl)-2-ethylindolizine 48j. 91% Yield. IR $\nu_{max}$ (neat) 2922, 1523, 1371, 1312 $cm^{-1}$.

8-Benzyloxy-2-ethyl-3-((3-thiophen-2-yl)thiophen-2-ylmethyl)indolizine 48l. $^1$H NMR ($CDCl_3$) δ 1.22 (3H, t, J=7.4 Hz), 2.63 (2H, q, J=7.4 Hz), 4.41 (2H, s), 5.06 (2H, s), 5.92 (1H, d, J=7.0 Hz), 6.17 (1H, dd, J=7.0, 7.2 Hz), 6.51 (1H, s), 6.91–7.42 (11H, m).

8-Benzyloxy-2-ethyl-3-(m-methoxybenzyl)indolizine 48m. Quantitative yield. $^1$H NMR ($CDCl_3$) δ 1.29 (3H, t, J=7.5 Hz), 2.72 (2H, q, J=7.5 Hz), 3.72 (3H, s), 4.21 (2H, s), 5.17 (2H, s), 6.01 (1H, d, J=7.2 Hz), 6.26 (1H, t, J=7.2 Hz), 6.58–6.75 (4H, m), 7.11–7.44 (5H, m), 7.46–7.63 (2H, m).

8-Benzyloxy-2-ethyl-3-(4-n-pentylcyclohexyl)methylindolizine 48o. $^1$H NMR ($CDCl_3$) δ 0.70–1.80 (24H, m), 2.57–2.71 (4H, m), 5.17 (2H, s), 5.98 (1H, d, J=7.4 Hz), 6.34 (1H, dd, J=7.0, 7.4 Hz), 6.53 (1H, s), 7.26–7.51 (6H, m).

8-Benzyloxy-3-(biphenyl-2-ylmethyl)-2-methylindolizine 48q.
Mp, 98–99° C. Quantitative yield.

3-Benzyl-8-benzyloxy-2-cyclopropylindolizine 48r. 94% Yield.

3-(p-n-Butylbenzyl)-2-ethyl-8-methoxyindolizine 48s. Method 2). Oil. 67.9% Yield.

8-Benzyloxy-2-ethyl-3-cyclohexylmethylindolizine 48t.
$^1$H NMR ($CDCl_3$) δ 1.00–1.26 (5H, m), 1.55–2.25 (6H, m), 2.25 (3H, s), 2.68 (2H, d, J=6.9 Hz), 5.16 (2H, s), 5.98 (1H, d, J=7.2 Hz), 6.34 (1H, dd, J=6.9, 7.2 Hz), 6.47 (1H, s), 7.30–7.49 (6H, m).

Part F: Preparation of
2-(8-Benzyloxy-2-ethyl-3-(substituted methyl)-indolizin-1-yl)-glyoxylamide 49

These compounds were prepared from 48, according to the procedure described for the synthesis of 35 from 34.

Other Preparations:

2-(8-Benzyloxy-2-ethyl-3-(p-phenylbenzyl)indolizine-1-yl) glyoxylamide 49a
Mp, 196–199° C. 61% Yield.

2-(8-Benzyloxy-3-cyclohexylmethyl-2-ethylindolizin-1-yl) glyoxylamide 49b. Mp, 176 C, (Hexane-EtOAc). 85% Yield.

2-(8-Benzyloxy-3-cyclopentylmethyl-2-ethylindolizin-1-yl) glyoxylamide 49c. Mp, 161–162 C, (Hexane-AcOEt). 77% Yield.

2-(8-Benzyloxy-3-cycloheptylmethyl-2-ethylindolizin-1-yl) glyoxylarnide 49d. Mp, 144–145 C, (Hexane). 76% Yield.

2-(8-Benzyloxy-2-ethyl-3-oxopentylindolizin-1-yl) glyoxylamide 49e. Mp, 141–142 C, (Hexane-EtOAc). 77% Yield.

2-(8-Benzyloxy-2-ethyl-3-(2-propylpentyl)indolizin-1-yl) glyoxylamide 49f. Mp, 159–160 C, (Hexane-EtOAc). 82% Yield.

2-(8-Benzyloxy-2-ethyl-3-(naphth-2-ylmethyl)indolizin-1-yl)glyoxylamide 49g. Mp, 209–210 C, (EtOAc). 77% Yield.

2-(8-Benzyloxy-3-(3,5-di-t-butylbenzyl-2-ethylindolizin-1-yl)glyoxylamide 49h. Mp, 230–231° C. (EtOAc). 59% Yield.

2-(8-Benzyloxy-2-ethyl-3-(2-phenylethyl)indolizin-1-yl) glyoxylamide 49i. Mp, 188–189° C. (EtOAc). 79% Yield.

2-(8-Benzyloxy-3-(o-benzylbenzyl)-2-ethylindolizin-1-yl) glyoxylamide 49j. Mp, 178–179° C. (hexane:EtOAc). 93% Yield.

2-(8-Benzyloxy-2-ethyl-3-(thiophen-2-yl methyl)indolizin-1-yl)glyoxylamide 49k. Mp, 191–192° C. (EtOAc). 73% Yield.

2-(8-Benzyloxy-2-ethyl-3-((3-thiophen-2-yl)thiophen-2-ylmethyl)indolizin-1-yl)glyoxylamide 49l. Mp, 208–209° C. (EtOAc). 10% Yield (2 steps).

2-(8-Benzyloxy-2-ethyl-3-(m-methoxybenzyl)indolizine-1-yl)glyoxylamide 49m. Mp, 180–182° C. 61% Yield.

2-(8-Benzyloxy-2-ethyl-3-(o-nitrobenzyl)indolizine-1-yl) glyoxylamide 49n. Mp, 205–208° C. 8% Yield.

2-(8-Benzyloxy-2-ethyl-3-((4-n-pentylcyclohexyl)methyl) indolizin-1-yl)glyoxylamide 49o. Mp, 169–170° C. (EtOAc). 80% Yield.

2-(3-(Adamant-1-yl methyl)-8-benzyloxy-2-ethylindolizin-1-yl)glyoxylamide 49p. Mp, 225–226° C. (EtOAc). 21% Yield (3 steps).

2-(8-Benzyloxy-3-(biphenyl-2-ylmethyl)-2-methylindolizin-1-yl)-glyoxylamide 49q. Mp, 198–200° C. 82.7% Yield.

2-(3-Benzyl-8-benzyloxy-2-cyclopropylindolizin-1-yl)-glyoxylamide 49r. Mp, 206–207° C. 30% Yield.

2-(3-(p-n-Butylbenzyl)-2-ethyl-8-methoxyindolizin-1-yl) glyoxylamide 49s. Mp, 195–196° C., (benzene). 96.8% Yield.

2-(8-Benzyloxy-3-cyclohexylmethyl-2-methylindolizin-1-yl)glyoxylamide 49t. Mp, 222–223° C. (EtOAc). 88% Yield.

2-(8-Benzyloxy-3-cyclopentylmethyl-2-cyclopropylindolizin-1-yl)glyoxylamide 49v.

8-Benzyloxy-3-cyclopentylcarbonyl-2-cyclopropylindolizine 47v and 8-benzyloxy-3-cyclopentylmethyl-2-cyclopropylindolizine 48v were prepared by the above procedure and used to the next preparation without further purification. Mp, 186–187° C. 28% Yield.

2-(8-Benzyloxy-3-cyclopentylmethyl-2-methylindolizin-1-yl)glyoxylamide 49w.

Preparation of

Compound 48w was prepared by the general procedure 2) cited above and used in the next preparation without further purification. Mp, 174–175° C. 66% Yield.

Part G: General Procedures for Preparation of 2-(3-(Substituted Methyl)-8-hydroxy-2-ethylindolizin-1-yl)-glyoxylamide 50

General Procedure 1)

These compounds were prepared from 49, according to the procedure described for the synthesis of 36 from 35.

General Procedure 2)

A 1 M solution of borontribromide in dichloromethane (3.3 eq. mol) was added to a solution of 49 in dichloromethane. The mixture was stirred for 3 hours to 1 day. Ice-water was added. The organic phase was washed with water and dried ($Na_2SO_4$). After removing the solvent at reduced pressure, the residue was purified by recrystallization or column chromatography.

Preparation of 2-(2-Ethyl-8-hydroxy-3-(o-phenylbenzyl)indolizine-1-yl) glyoxylamide 50a.

Quantitative yield. $^1$H NMR ($CDCl_3$) δ 1.25 (3H, t, J=7.5 Hz), 2.93 (2H, q, J=7.5 Hz), 4.25 (2H, s), 5.76 (1H, br.s), 6.39 (1H, br.s), 6.70 (1H, d, J=7.2 Hz), 6.79 (1H, t, J=7.1 Hz), 7.08–7.78 (10H, m), 12.90 (1H, s).

Other Preparations:

2-(3-Cyclopentylmethyl-2-ethyl-8-hydroxyindolizin-1-yl) glyoxylamide 50c.

2-(3-Cycloheptylmethyl-2-ethyl-8-hydroxyindolizin-1-yl) glyoxylamide 50d.

2-(2-Ethyl-8-hydroxy-3-oxopentylindolizin-1-yl) glyoxylamide 50e.

3-(2,5-Di-t-butylbenzyl)-8-hydroxy-2-ethylindolizin-1-yl) glyoxylamide 50h.

2-(2-Ethyl-8-hydroxy-3-(thiophen-2-ylmethyl)indolizin-1-yl)glyoxylamide 50k. Mp, 163–164° C. (hexane:EtOAc). 40% Yield.

2-(2-Ethyl-8-hydroxy-3-((3-thiophen-2-yl)thiophen-2-ylmethyl)indolizine-1-yl)glyoxylamide 50l.

2-(2-Ethyl-8-hydroxy-3-(m-methoxybenzyl)indolizine-1-yl)glyoxylamide 50m. Mp, 140–143° C. 86% Yield.

2-(2-Ethyl-8-hydroxy-3-(o-nitrobenzyl)indolizine-1-yl) glyoxylamide 50n. Mp, 174–178° C. (dec.). 85% Yield.

8-Hydroxy-2-ethyl-3-(4-n-pentylcyclohexylmethyl) indolizin-1-yl)glyoxylamide 50o. Mp, 99–100° C. (hexane:EtOAc).

2-(3-(Biphenyl-2-ylmethyl)-8-hydroxy-2-methylindolizin-1-yl)-glyoxylamide 50q. Mp, 129–130° C. 77.6% Yield.

2-(3-Benzyl-2-cyclopropyl-8-hydroxyindolizin-1-yl)-glyoxylamide 50r. mp, 188–190° C. 96.7% Yield.

2-(3-(p-n-Butylbenzyl)-2-ethyl-8-hydroxyindolizin-1-yl) glyoxylamide 50s. Mp, 145–148° C., (benzene). 59.3% Yield.

2-(3-Cyclohexylmethyl-8-hydroxy-2-methylindolizin-1-yl) glyoxylamide 50t.

Part H: General Procedure for Preparation of 2-(8-Carbomethoxymethyloxy-2-ethyl-3-(substituted metyl)-indolizin-1-yl)-glyoxylamide 51

Compound 50 (1 m mol), methyl bromoacetate (1.1 m mol), $K_2CO_3$ (3 m mol), KI (0.2 m mol), DMF (3 ml) was stirred for 5 hours. Water was added. The mixture was extracted with ethyl acetate. The extracts were washed with water and dried ($Na_2SO_4$). After removing the solvent at reduced pressure, the residue was purified by recrystallization or column chromatography.

Other Preparations:

2-(2-Ethyl-8-(carbomethoxymethyloxy)-3-(o-phenylbenzyl)indolizine-1-yl)glyoxylamide 51a. Mp, 221–222° C. 54% Yield.

2-(8-(Carbomethoxymethyloxy)-3-cyclohexylmethyl-2-ethylindolizin-1-yl)glyoxylamide 51b. Mp, 149–150 C, (Hexane-EtOAc). 19% Yield from 49b.

2-(8-(Carbomethoxymethyloxy)-3-cyclopentylmethyl-2-ethylindolizin-1-yl)glyoxylamide 51c. Mp, 158–159 C, (AcOEt). Quantitative yield.

2-(8-(Carbomethoxymethyloxy)-3-cycloheptylmethyl-2-ethylindolizin-1-yl)glyoxylamide 51d. Mp, 147–148 C, (AcOEt). 79% Yield.

2-(8-(Carbomethoxymethyloxy)-2-ethyl-3-oxopentylindolizin-1-yl)glyoxylamide 51e. Mp, 140–141 C, (Hexane-EtOAc). 36% Yield.

2-(8-(Carbomethoxymethyloxy)-2-ethyl-3-(2-propylpentyl) indolizin-1-yl)glyoxylamide 51f. Mp, 114–115 C, (Hexane-EtOAc). 84% Yield.

2-(8-(Carbomethoxymethyloxy)-2-ethyl-3-(naphth-2-ylmethyl)indolizin-1-yl)glyoxylamide 51g. Mp, 195–196 C, (EtOAc). Quantitative yield.

2-(8-(Carboxyymethyloxy)-3-(3,5-di-t-butyl)benzyl)-2-ethylindolizin-1-yl)glyoxylamide 51h. Mp, 186–187° C. (EtOAc). 83% Yield (2 steps).

2-(8-(carbomethoxymethyloxy-2-ethyl-3-(2-phenylethyl) indolizin-1-yl)glyoxylamide 51i. Mp, 175–176° C. (EtOAc). 47% Yield (2 steps).

2-(3-o-Benzylbenzyl)-8-(carbomethoxymethyloxy)-2-ethylindolizin-1-yl)glyoxylamide 51j. Mp, 190–191° C. (EtOAc). 65% Yield (2 steps).

2-(8-(Carbomethoxymethyloxy)-2-ethyl-3-(thiophen-2-yl) indolizin-1-yl)glyoxylamide 51k. Mp, 182° C. (hexane:EtOAc). 75% Yield.

2-(8-(Carbomethoxymethyloxy)-2-ethyl-3-((3-thiophen-2-yl)thiophen-2-ylmethyl)indolizin-1-yl)glyoxylamide 51l. Mp, 176–177 0C.

2-(2-Ethyl-8-(carbomethoxymethyloxy)-3-(m-methoxybenzyl)indolizine-1-yl)glyoxylamide 51m. Mp, 155–157° C. 85% Yield.

2-(2-Ethyl-8-(carbomethoxymethyloxy)-3-(o-nitrobenzyl) indolizine-1-yl)glyoxylamide 51n. Mp, 156–157° C. 96% Yield.

2-(8-(Carbomethoxymethyloxy)-2-ethyl-3-((4-n-pentylcyclohexyl)methylindolizin-1-yl)glyoxylamide 51o. Mp, 175–176° C. (hexane:EtOAc). 92% Yield (2 steps).

2-(3-(Adamant-1-ylmethyl)-8-(carbomethoxymethyloxy)-2-methylindolizin-1-yl)glyoxylamide 51p. Mp, 191–192° C. (EtOAc). 38% Yield (2 steps).

2-(3-Benzyl-8-carbomethoxymethyloxy-2-cyclopropylindolizin-1-yl)-glyoxylamide 51r. Mp, 186–188° C. 74.5% Yield.

2-(3-(p-n-Butylbenzyl)-8-(carbomethoxymethyloxy)-2-ethylindolizin-1-yl)glyoxylamide 51s. Mp, 174–176° C., (EtOAc:benzene). 70.9% Yield.

2-(8-(Carbomethoxymethyoxy-3-cyclohexylmethyl-2-5 methylindolizin-1-yl)glyoxylamide 51t. Mp, 177–178° C. (hexane:EtOAc). 68% Yield (2 steps).

2-(8-(Carbomethoxymethyloxy)-3-cyclopentylmethyl-2-cyclopropylindolizin-1-yl)glyoxylamide 51v.

2-(3-Cyclopentylmethyl-2-cyclopropyl-8-hydroxyindolizin-1-10 yl)glyoxylamide 50v was prepared by the general procedure 2) cited above and used to the next preparation without further purification. Mp, 175–176 0C. 70.4% Yield.

2-(8-(Carbomethoxymethyloxy)-3-cyclopentylmethyl-2-methylindolizin-1-yl)glyoxylamide 51w Other Preparations:

Compound 50w was prepared by the general procedure 2) cited above and used in the next preparation without further purification. Mp, 149–150 0C. 63% Yield.

Part I: General Procedure for Preparation of 2-(8-Carboxymethyloxy-2-ethyl-3-(substituted methyl)-indolizin-1-yl)glyoxylamide 52

Hydrolysis of 51 was carried out by the procedure described for the preparation of 22 with lithium hydroxide.

Other Preparations:

2-(2-Ethyl-8-(carboxyymethyloxy)-3-(p-phenylbenzyl)indolizine-1-yl)glyoxylamide 52a Mp, 229–234° C. (dec.). 84% Yield. IR $v_{max}$ (nujol) 3417, 1734, 1653, 1629, 1496, 1237 cm$^{-1}$. $^1$H NMR (d$_6$-DMSO) δ 1.14 (3H, t, J=7.5 Hz), 2.83 (2H, q, J=7.5 Hz), 4.36 (2H, s), 4.72 (2H, s), 6.44 (1H, d, J=7.5 Hz), 6.70 (1H, t, J=7.2 Hz), 7.20 (2H, d, J=8.4 Hz), 7.30–7.36 (2H, m), 7.43 (2H, t, J=7.5 Hz), 7.55–7.64 (4H, m), 7.67 (1H, br.s), 7.73 (1H, d, J=6.6 Hz), 12.80–13.60 (1H, br.). Analyses: Calc'd for $C_{27}H_{24}N_2O_5$.0.1H$_2$O: C, 70.76; H, 5.32; N, 6.11. Found: C, 70.53; H, 5.40; N, 6.19.

2-(8-Carboxymethyloxy-3-cyclohexylmethyl-2-ethylindolizin-1-yl)glyoxylamide 52b

Mp, 224–225° C. (AcOEt). Na salt: $^1$H NMR (d$_6$-DMSO) 1.0–1.15 (8H, m), 1.5–1.66 (6H, m), 2.6–2.7 (4H, m), 4.1 (2H, s), 6.46 (1H, d, J=7.5 Hz), 6.76 (1H, dd, J=6.6, 7.5 Hz), 7.8 (1H, d, J=6.6 Hz).

2-(8-Carboxymethyloxy-3-cyclopentylmethyl-2-ethylindolizin-1-yl)glyoxylamide 52c 43% Yield. IR $v_{max}$ (KBr) 3461, 2952, 1703, 1636, 1583, 1536, 1306, 1262 cm$^{-1}$.

Calc'd for $C_{20}H_{24}N_2O_5$0.4H$_2$O: C, 63.28; H, 6.58; N, 7.38. Found: C, 63.25; H, 6.40; N, 7.28.

Na salt: IR $v_{max}$ (KBr) 3450, 1664, 1618, 1489 cm$^{-1}$.

2-(8-Carboxymethyloxy-3-cycloheptylmethyl-2-ethylindolizin-1-yl)glyoxylamide 52d 76% Yield. IR $v_{max}$ (KBr) 3474, 2924, 1724, 1623 cm$^{-1}$.

Na salt: IR $v_{max}$ (KBr) 3474, 2924, 1675, 1618, 1493 cm$^{-1}$.

Calc'd for $C_{22}H_{27}N_2NaO_5$.1.5H$_2$O: C, 58.79; H, 6.73; N, 6.23, Na, 5.11. Found: C, 58.86; H, 6.70; N, 6.34; Na, 5.13.

2-(8-Carboxymethyloxy-2-ethyl-3-pentylindolizin-1-yl)glyoxylamide 52e

Mp, 232–233° C. (acetone:AcOEt). 37% Yield. IR $v_{max}$ (KBr) 3476, 2931, 1709, 1638, 1613 cm$^{-1}$. $^1$H NMR (CDCl$_3$+CD$_3$OD) δ 0.87–0.95 (3H, m), 1.19 (3H, t, J=7.6 Hz), 1.32–1.62 (6H, m), 2.73–2.86 (4H, m), 4.74 (2H, s), 6.36 (1H, d, J=7.6 Hz), 6.70 (1H, dd, J=6.6, 7.6 Hz), 7.61 (1H, d, J=6.6 Hz). [MS] m/z 360 [M]$^+$.

2-(8-Carboxymethyloxy-2-ethyl-3-(2-propylpentyl)indolizin-1-yl)glyoxylamide 52f

Mp, 176–177° C. (hexane:AcOEt). 81% Yield. IR $v_{max}$ (KBr) 3388, 2931, 2871, 1736, 1644, 1619, 1237 cm$^{-1}$. $^1$H NMR (CDCl$_3$+CD$_3$OD) δ 0.85–0.90 (6H, m), 1.15–1.5 (1H, m), 1.70 (1H, m), 2.72–2.83 (4H, m), 4.72 (2H, s), 6.36 (1H, d, J=7.8 Hz), 6.68 (1H, dd, J=6.9. 7.8 Hz), 7.58 (1H, d, J=6.9 Hz). [MS] m/z 402 [M]$^+$. Calc'd for $C_{22}H_{30}N_2O_5$.1.1H$_2$O: C, 62.57; H, 7.69; N, 6.63. Found: C, 62.57; H, 7.28; N, 6.59.

2-(8-Carboxymethyloxy-2-ethyl-3-(naphth-2-yl)indolizin-1-yl)glyoxylamide 52g

Mp, 236–237° C. (AcOEt). 33% Yield. IR $v_{max}$ (KBr) 3441, 1730, 1643, 1619, 1500, 1243 cm$^{-1}$. $^1$H NMR (CDCl$_3$+CD$_3$OD) δ 1.25 (3H, t, J=7.4 Hz), 2.94 (2H, q, J=7.4 Hz), 3.80 (3H, s), 4.42 (2H, s), 4.73 (2H, s), 6.35 (1H, d, J=7.4 Hz), 6.52 (1H, dd, J=7.0, 7.4 Hz), 7.25–7.82 (13H, m). [MS] m/z 430 [M]$^+$. Calc'd for $C_{25}H_{22}N_2O_5$.0.6H$_2$O: C, 68.05; H, 5.30; N, 6.35. Found: C, 67.94; H, 5.18; N, 6.33.

2-(8-(Carboxymethyloxy)-3-(3,5-di-t-butylbenzyl)-2-ethylindolizin-1-yl)glyoxylamine 52h Mp, 144–145° C. (hexane:EtOAc). 43% Yield.

2-(8-(Carboxymethyoxy)-2-ethyl-3-(2-phenylethyl)indolizin-1-yl)glyoxylamide 52i

Mp, 233–234° C. (EtOAc). 48% Yield. IR $v_{max}$ (KBr) 3477, 1707, 1637, 1491 cm$^{-1}$. $^1$H NMR (CDCl$_3$+CD$_3$OD) δ 1.13 (3H, t, J=7.4 Hz), 2.71 (2H, q, J=7.4 Hz), 2.84–2.92 (2H, m), 3.10–3.18 (2H, m), 4.73 (2H, s), 6.38 (1H, d, J=7.4 Hz), 6.69 (1H, dd, J=6.8, 7.4 Hz), 7.15–7.33 (5H, m), 7.60 (1H, d, J=6.8 Hz). [MS] m/z 394 [M]$^+$. Analyses: Calc'd for $C_{22}H_{22}N_2O_5$: C, 66.99; H, 5.62; N, 7.1. Found: C, 66.85; H, 5.73; N, 7.01.

2-(8-(Carboxymethyloxy)-3-o-benzylbenzyl-2-ethylindolizin-1-yl)glyoxylamide 52j

Mp, 220–221° C. (EtOAc). 42% Yield. IR $v_{max}$ (KBr) 3438, 1731, 1620, 1494, 1217 cm$^{-1}$. $^1$H NMR (CDCl$_3$+CD$_3$OD) δ 1.11 (3H, t, J=7.4 Hz), 2.72 (2H, q, J=7.4 Hz), 4.07 (2H, s), 4.19 (2H, s), 4.69 (2H, s), 6.30 (1H, d, J=6.8 Hz), 6.38 (1H, dd, J=6.8, 7.8 Hz), 6.54 (1H, d, J=7.4 Hz), 6.71 (1H, d, J=5.8 Hz), 7.00–7.36 (8H, m). [MS] m/z 470 [M]$^+$. Analyses: Calc'd for $C_{28}H_{26}N_2O_5$: C, 71.48; H, 5.57; N, 5.95. Found: C, 71.27; H, 5.64; N, 5.92.

2-(8-(Carboxymethyloxy)-2-ethyl-3-(thiophen-2-ylmethyl)indolizin-1-yl)glyoxylamide 52k Mp, 251–252° C. (EtOAc). 32% Yield. IR $v_{max}$ (KBr) 3422, 1702, 1659, 1625, 1535, 1494 cm$^{-1}$. $^1$H NMR (d$_6$-DMSO) δ 1.14 (3H, t, J=6.8 Hz), 2.80 (2H, q, J=6.8 Hz), 4.50 (2H, s), 4.71 (2H, s), 6.45 (1H, d, J=8.0 Hz), 6.72 (1H, dd, J=6.8, 8.0 Hz), 6.90–6.94 (2H, m), 7.29–7.32 (2H, m), 7.67 (1H, br.s), 7.82 (1H, d, J=6.8 Hz). [MS] m/z 386 [M]$^+$. Analyses: Calc'd for $C_{19}H_{18}N_2O_5S$.0.6H$_2$O: C, 57.45; H, 4.87; N, 7.05; S, 8.07. Found: C, 57.50; H, 4.71; N, 6.89; S, 8.11.

2-(8-(Carboxymethyloxy)-2-ethyl-3-((3-thiophen-2-yl)thiophen-2-ylmethyl)indolizin-1-yl)glyoxylamide 52l Mp, 209–210° C. 54.5% Yield. $^1$H NMR (d$_6$-DMSO) δ 1.11 (3H, t, J=7.4 Hz), 2.75 (2H, q, J=7.4 Hz), 4.60 (2H, s), 4.71 (2H, s), 6.45 (1H, d, J=7.4 Hz), 6.69 (1H, dd, J=7.0, 7.4 Hz), 7.20–7.34 (4H, m), 7.46–7.65 (4H, m). IR $v_{max}$ (KBr) 3400, 1645, 1591 cm$^{-1}$. Analyses: Calc'd for $C_{23}H_{20}N_2O_5S_2$: C, 58.96; H, 4.30; N, 5.98; S, 13.69. Found: C, 58.59; H, 4.31; N, 5.92; S, 13.45.

2-(2-Ethyl-8-(carboxymethyloxy)-3-(m-methoxybenzyl)indolizine-1-yl)glyoxylamide 52m Mp, 219–221° C. (dec.). 80% Yield. IR $v_{max}$ (nujol) 3310, 3173, 1703, 1596, 1492 cm$^{-1}$. $^1$H NMR (d$_6$-DMSO) δ 1.11 (3H, t, J=7.5 Hz), 2.80 (2H, q, J=7.5 Hz), 3.70 (3H, s), 4.28 (2H, s), 4.71 (2H, s), 6.43 (1H, d, J=7.5 Hz), 6.60–6.81 (4H, m), 7.18 (1H, t, J=7.8 Hz), 7.32 (1H, br.s), 7.63–7.72 (2H, m), 12.70–13.30 (1H, br.). Analyses: Calc'd for $C_{22}H_{22}N_2O_6$.0.8H$_2$O: C, 62.20; H, 5.60; N, 6.59. Found: C, 62.00; H, 5.37; N, 6.54.

2-(2-Ethyl-8-(carboxymethyloxy)-3-(o-nitrobenzyl)indolizine-1-yl)glyoxylamide 52n Mp, 208–210° C. (dec.) 69% Yield. IR $v_{max}$ (nujol) 3350, 1750, 1600, 1493, 1344, 1235 cm$^{-1}$. $^1$H NMR (d$_6$-DMSO) δ 1.04 (3H, t, J=7.5 Hz), 2.72 (2H, q, J=7.5 Hz), 4.64 (2H, s), 4.73 (2H, s), 6.46 (1H, d, J=7.5 Hz), 6.56–6.61 (1H, m), 6.68 (1H, t, J=7.5 Hz), 7.36 (1H, br.s), 7.45–7.59 (2H, m), 7.64–7.75 (2H, m), 8.10–8.16 (1H, m), 12.80–13.40 (1H, br.). Analyses: Calc'd for $C_{21}H_{19}N_3O_7$.0.3H$_2$O: C, 58.55; H, 4.59; N, 9.75. Found: C, 58.57; H, 4.77; N, 9.47.

2-(8-(Carboxymethyloxy)-2-ethyl-3-(4-n-pentylcyclohexylmethyl)indolizin-1-yl)glyoxylamide 52o Mp, 224–225° C. (EtOAc). 59% Yield (from Na salt). IR $\nu_{max}$ (KBr) 3472, 2922, 1706, 1636, 1489 cm$^{-1}$. $^1$H NMR (d$_6$-DMSO) δ 0.70–1.80 (24H, m), 2.60–2.80 (4H, m), 4.70 (2H, s), 6.41 (1H, d, J=7.8 Hz), 6.74 (1H, dd, J=6.6, 7.8 Hz), 7.29 (1H, br.s), 7.62 (1H, br.s), 7.89 (1H, d, J=6.6 Hz). [MS] m/z 479 [M+H]$^+$, 501 [M+Na]$^+$. Analyses: Calc'd for C$_{26}$H$_{36}$N$_2$O$_5$·0.7H$_2$O: C, 66.56; H, 8.03; N, 5.97. Found: C, 66.42; H, 7.65; N, 5.93.

Na salt: 89% Yield. IR $\nu_{max}$ (KBr) 3469, 2921, 1619, 1490 cm$^{-1}$. $^1$H NMR (d$_6$-DMSO) δ 0.80–1.80 (24H, m), 2.60–2.80 (4H, m), 4.14 (2H, s), 6.21 (1H, d, J=7.8 Hz), 6.67 (1H, dd, J=6.6, 7.8 Hz), 7.16 (1H, br.s), 7.75 (1H, d, J=6.6 Hz), 7.90 (1H, br.s).

2-(3-(Adamant-1-ylmethyl)-8-(carboxymethyloxy)-2-methylindolizin-1-yl)glyoxylamide 52p. Mp, 237–238° C. (EtOAc). 60% Yield.

2-(3-Benzyl-8-carboxymethyloxy-2-cyclopropylindolizin-1-yl)-glyoxylamide 52r. Mp, 235–237° C. 74.6% Yield. IR $\nu_{max}$ (nujol) 3414, 3304, 2722, 2600, 2530, 1727, 1647 (sh), 1623, 1605 (sh) cm$^{-1}$. $^1$H NMR (CDCl$_3$) δ 0.47–0.55 (2H, m), 0.90–1.00 (2H, m), 2.05–2.18 (1H, m), 4.43 (2H, s), 4.75 (2H, s), 6.27 (1H, br.s), 6.41 (1H, d, J=7.6 Hz), 6.59 (1H, t, J=7.1 Hz), 7.02–7.06 (2H+1H, m+br.s), 7.25–7.36 (4H, m). Analyses: Calc'd for C$_{22}$H$_{20}$N$_2$O$_5$·0.2H$_2$O: C, 66.73; H, 5.19; N, 7.07. Found: C, 66.77; H, 5.20; N, 7.13.

2-(3-(p-n-Butylbenzyl)-8-(carboxymethyloxy)-2-ethylindolizin-1-yl)glyoxylamide 52s Mp, 217–220° C., (EtOAc). 92.4% Yield. IR $\nu_{max}$ (nujol) 3422, 1735, 1653, 1630, 1497 cm$^{-1}$. $^1$H NMR (CDCl$_3$+CD$_3$OD) δ 0.91 (3H, t, J=7.4 Hz), 1.22 (3H, t, J=7.5 Hz), 1.44 (2H, m), 1.56 (2H, m), 2.56 (2H, t, J=7.8 Hz), 2.88 (2H, q, J=7.5 Hz), 4.21 (2H, s), 4.72 (2H, s), 6.35 (1H, d, J=7.8 Hz), 6.56 (1H, t, J=6.9 Hz), 6.99 (1H, d, J=7.8 Hz), 7.08 (1H, d, J=8.1 Hz), 7.40 (1H, d, J=6.9 Hz). Analyses: Calc'd for C$_{23}$H$_{26}$N$_2$O$_3$·0.1H$_2$O: C, 72.65; H, 6.94; N, 7.37. Found: C, 72.57; H, 6.93; N, 7.39.

2-(8-(Carboxymethyloxy)-3-cyclohexylmethyl-2-methylindolizin-1-yl)glyoxylamide 52t Mp, 235–236° C. (hexane:EtOAc). IR $\nu_{max}$ (KBr) 3475, 2924, 1703, 1637, 1602, 1488, 1301 cm$^{-1}$. $^1$H NMR (d$_6$-DMSO) δ 1.00–1.80 (11H, m). 2.25 (3H, s), 2.75 (2H, d, J=6.2 Hz), 4.7 (2H, s), 6.42 (1H, d, J=7.4 Hz), 6.75 (1H, dd, J=7.0, 7.4 Hz), 7.29 (1H, br.s), 7.60 (1H, br.s), 7.90 (1H, d, J=7.0 Hz). [MS] m/z 372 [M]$^+$. Analyses: Calc'd for C$_{20}$H$_{24}$N$_2$O$_5$·0.8H$_2$O: C, 62.10; H, 6.67; N, 7.24. Found: C, 62.02; H, 6.40; N, 6.98.

Na salt: 76% Yield. IR $\nu_{max}$ (KBr) 3447, 2923, 1665, 1619, 1489, 1409 cm$^{-1}$. $^1$H NMR (d$_6$-DMSO) δ 0.95–1.75 (11H, m), 2.22 (3H, s), 2.72 (2H, d, J=6.3 Hz), 4.15 (2H, s), 6.22 (1H, d, J=7.5 Hz), 6.68 (1H, dd, J=6.9, 7.5 Hz), 7.77 (1H, d, J=6.9 Hz). [MS] m/z 395 [M+H]$^+$, 417 [M+Na]$^+$.

2-(8-(Carboxymethyloxy)-3-cyclopentylmethyl-2-cyclopropylindolizin-1-yl)glyoxylamide 52v. Mp, 237–238° C. 20% Yield. IR $\nu_{max}$ max (KBr) 3430, 2951, 1730, 1647, 1623, 1499, 1240 cm$^{-1}$. $^1$H NMR (CDCl$_3$) d 0.38–0.44 (2H, m), 0.78–0.90 (2H, m), 1.16–1.90 (9H, m), 2.16 (1H, m), 2.96 (2H, d, J=7.4 Hz), 4.69 (2H, s), 6.33 (1H, d, J=7.8 Hz), 6.69 (1H, dd, J=6.6, 7.8 Hz), 7.33 (1H, br.s), 7.67 (1H, br.s), 7.88 (1H, d, J=6.6 Hz). Analyses: Calc'd for C$_{21}$H$_{24}$N$_2$O$_5$: C, 65.61; H, 6.29; N, 7.29. Found: C, 65.33; H, 6.20; N, 7.28.

2-(8-(Carboxymethyloxy)-3-cyclopentylmethyl-2-methylindolizin-1-yl)glyoxylamide 52w. Mp, 249–251° C. (dec.). 85% Yield. IR $\nu_{max}$ (nujol) 3470, 3254, 1704, 1636, 1598, 1537, 1488, 1302 cm$^{-1}$. $^1$H NMR (CDCl$_3$) d 1.16–1.31 (2H, m), 1.42–1.73 (6H, m), 2.03–2.20 (1H, m), 2.28 (3H, s), 2.87 (2H, d, J=7.5 Hz), 4.71 (2H, s), 6.43 (1H, d, J=7.2 Hz), 6.75 (1H, t, J=7.2 Hz), 7.29 (1H, br.s), 7.61 (1H, br.s), 7.95 (1H, d, J=6.9 Hz,), 12.70–13.38 (1H, br.s). Analyses: Calc'd for C$_{19}$H$_{22}$N$_2$O$_5$: C, 63.68; H, 6.19; N, 7.82. Found: C, 63.42; H, 6.18; N, 7.69.

Na salt: Mp, >250° C. IR $\nu_{max}$ (nujol) 3221, 1677, 1653, 1499, 1415 cm$^{-1}$. Analyses: Calc'd for C$_{19}$H$_{21}$N$_2$O$_5$Na: C, 60.00; H, 5.57; N, 7.36; Na, 6.04. Found: C, 60.28; H, 5.70; N, 7.30; Na, 6.06.

Example 6

Part A: Preparation of 3-(Carbomethoxymethyloxy)-2-methylpyridine 53

A solution of methyl bromoacetate (1.31 g, 8.56 m mole) in tetrahydrofuran (5 ml) was added dropwise to a mixture of 3-hydroxy-2-methylpyridine (0.793 g, 7.27 m mole), pulverized potassium hydroxide (0.768 g, 11.8 m mole) and tetrabutylammonium bromide (30 mg, 0 09 m mole) in tetrahydrofuran (10 ml) with cooling in ice. The mixture was stirred at room temperature for 1 hour. Ice-water was added. The mixture was extracted with dichloromethane. The extracts were washed with water, dried (Na$_2$SO$_4$) and concentrated under reduced pressure. The residue was chromatographed on silica gel (25 g) in ethyl acetate:hexane (2:1) to give an oil, 791 mg (60.1%).

$^1$H NMR (CDCl$_3$) δ 2.55 (3H, s), 3.81 (3H, s), 4.67 (2H, s), 6.97 (1H, dd, J=8.2 Hz), 7.09 (1H, dd, J=8.2, 4.8 Hz), 8.14 (1H, dd, J=1.4, 4.6 Hz).

Preparation of (8-Carbomethoxymethyloxy)-2-methylindolizine 54a (2-Methylpyridin-3-yloxy)acetic acid methyl ester (53, 1.75 g, 9.66 m mol) and chloroacetone (0.77 ml, 9.66 m mol) were heated at 95° C. under N$_2$ for 2 hours. The DBU (3.2 ml, 21.3 m mol) in benzene (11 ml) were added to the salt. The mixture was then refluxed under N$_2$ for 1 hr, poured to ice-water and then extracted with ethyl acetate. The extracts were washed with water and dried (Na$_2$SO$_4$). After removing the solvents at reduced pressure, the residue was recrystallized from ether-hexane to give 804 mg (40% yield) of the titled compound. Mp, 59–62° C. $^1$H NMR (CDCl$_3$) δ 2.30 (3H, s), 3.80 (3H, s), 4.72 (2H, s), 5.82 (1H, d, J=7.5 Hz), 6.26 (1H, t, J=6.9 Hz), 6.46 (1H, s), 7.08 (1H, s), 7.51 (1H, d, J=6.6 Hz).

Part B: Preparation of 8-(Carbomethoxymethyloxy)-2-ethylindolizine 54b

A solution of 1-bromo-2-butanone (470 mg, 3.12 m mole) in ethyl acetate (3 ml) was added to a solution of 53 (565 mg, 3.12 m mole) in ethyl acetate (5 ml). The solution was heated under reflux for 1 hour and the volatile materials were removed by distillation under reduced pressure to give an oil.

$^1$H NMR (CDCl$_3$+CD$_3$OD) δ 1.17 (3H, t, J=7.2 Hz), 2.63 (3H, s), 2.87 (2H, q, J=7.2 Hz), 3.84 (3H, s), 5.01 (2H, s), 6.16 (2H, s), 7.84 (1H, dd, J=8.6, 6.0 Hz), 8.02 (1H, dd, J=8.8, 1.0 Hz), 8.78 (1H, dd, J=6.4, 1.0 Hz).

A mixture of the salt and DBU (1.20 g) in benzene (5 ml) was heated under reflux for 1 hour. washed with water, dried (Na$_2$SO$_4$) and concentrated under reduced pressure. The residue was chromatographed on silica gel (40 g) in hexane:ethyl acetate (3:2) to give an oil, 601 mg (82.6% from 53). $^1$H NMR (CDCl$_3$) δ 1.29 (3H, t, J=7.5 Hz), 2.70 (2H, q, J=7.8 Hz), 3.81 (3H, s), 4.74 (2H, s), 5.86 (1H, d, J=6.9 Hz), 6.30 (1H, t, J=7.1 Hz), 6.51 (1H, s), 7.11 (1H, s), 7.56 (1H, d, J=4.2 Hz).

Other Preparations:

(2-Isopropylindolizin-8-yloxy)acetic acid methyl ester 54c

This compound was prepared by the procedure cited above. 59% Yield. Oil. $^1$H NMR (CDCl$_3$) δ 1.30 (6H, d, J=6.6 Hz), 3.02 (1H, sept, J=6.6 Hz), 3.81 (3H, s), 4.73 (2H, s), 5.82 (1H, d, J=7.4 Hz), 6.27 (1H, t, J=7.0 Hz), 6.53 (1H, s), 7.12 (1H, s), 7.53 (1H, d, J=7.0 Hz).

8-(Carbomethoxymethyloxy)-2-cyclopropylindolizine 54d

This compound was prepared by the procedure cited above. Oil. 76% Yield. $^1$H NMR (CDCl$_3$) δ 0.65 (2H, m), 0.92 (2H, m), 1.90 (1H, m), 3.81 (3H, s), 4.71 (2H, s), 5.82 (1H, d, J=7.4 Hz), 6.28 (1H, d, J=7.4 Hz), 6.28 (1H, t, J=7.2 Hz), 6.34 (1H, s), 7.13 (1H, d, J=1.4 Hz), 7.50 (1H, d, J=6.8 Hz).

2-t-Butyl-8-(carbomethoxymethyloxy)indolizine 54e

This compound was prepared by the procedure cited above. Oil. 48.0% Yield.

8-(Carbomethoxymethyloxy)-2-cyclopentylindolizine 54f

This compound was prepared by the procedure cited above. Oil. 14.3% Yield. $^1$H NMR (CDCl$_3$) δ 1.6–2.2 (8H, m), 3.11 (1H, m), 3.83 (3H, s), 4.74 (2H, s), 5.84 (1H, d, J=7.4 Hz), 6.29 (1H, t, J=7.0 Hz), 6.53 (1H, s), 7.14 (1H, s), 7.34 (1H, d, J=7.2 Hz).

Part C: Preparation of 8-(Carbomethoxymethyloxy)-2-ethyl-3-(o-phenylbenzoyl)indolizine 55b This compound was prepared from 54b, according to the procedure cited for the preparation of 47 from 46. 83% Yield. $^1$H NMR (CDCl$_3$) δ 1.05 (3H, t, J=7.5 Hz), 2.07 (2H, q, J=7.5 Hz), 3.82 (3H, s), 4.74 (2H, s), 6.31 (1H, d, J=7.4 Hz), 6.49 (1H, d, J=0.6 Hz), 6.65 (1H, t, J=7.4 Hz), 7.10–7.25 (3H, m), 7.30–7.40 (2H, m), 7.42–7.58 (5H, m), 9.40 (1H, d, J=7.4 Hz).

Preparation of 8-(Carbomethoxymethyloxy)-3-cyclohexanecarbonyl-2-cyclopropylindolizine 55d This compound was prepared from 54d, according to the procedure, described for the preparation of 47 from 46. Mp, 110–111.5° C. 74% Yield.

Part D: General Procedure for Preparation of 2-Alkyl-8-(carbomethoxymethyloxy)-3-(substituted methyl)indolizine 56

A solution of 54 (1.30 m mole) and alkyliodide (1.56 m mole) in benzene (5 ml) was allowed to stand at room temperature for 2 days. Ethyl acetate was added. The mixture was washed with sodium hydrogencarbonate and washed with water, dried (Na$_2$SO$_4$) and concentrated under reduced pressure. The residue was chromatographed on silica gel in hexane:benzene (1:2).

Other Preparations:

8-(Carbomethoxymethyloxy)-2-ethyl-3-(o-phenylbenzyl)indolizine 56b. 56% Yield. Oil. $^1$H NMR (CDCl$_3$) δ 1.25 (3H, t, J=7.5 Hz), 2.64 (2H, q, J=7.5 Hz), 3.81 (3H, s), 4:11 (2H, s), 4.72 (2H, s), 5.80 (1H, d, J=7.2 Hz), 6.17 (1H, t, J=7.2 Hz), 6.59 (1H, s), 6.68 (1H, d, J=7.8 Hz), 6.95 (1H, d, J=6.9 Hz), 7.1–7.55 (7H, m).

(3-(Biphenyl-2-ylmethyl)-8-(carbomethoxymethyloxy)-2-isopropylindolizine 56c. Mp, 115–117° C. 37% Yield.

8-(Carbomethoxymethyloxy)-2-cyclopropyl-3-(o-phenylbenzyl)indolizine 56d. Mp, 130–131° C. (hexane). 33% Yield.

2-t-Butyl-8-(carbomethoxymethyloxy)-3-(o-phenylbenzyl)indolizine 56e. Mp, 155–157° C. (hexane). 22.5% Yield.

8-(Carbomethoxymethyloxy)-2-cyclopentyl-3-(o-phenylbenzyl)indolizine 56f. Mp, 145–148° C. (hexane). 26.2% Yield.

8-(Carbomethoxymethyloxy)-2-ethyl-3-(m-phenylbenzyl)indolizine 56g.

The product could not be isolated from 1,3-disubstituted indolizine and used in the next preparation without further purification.

8-(Carbomethoxymethyloxy)-2-ethyl-3-(3-phenyl-2-propenyl)indolizine 56h.

The product could not be isolated from 1,3-disubstituted indolizine and used in the next preparation without further purification.

8-(Carbomethoxymethyloxy)-2-cyclopropyl-3-(1-naphthylmethyl)indolizine 56j.

The product could not be isolated from 1,3-disubstituted indolizine and used in the next preparation without further purification.

8-(Carbomethoxymethyloxy)-3-cyclohexylmethyl-2-cyclopropylindolizine 56k. 42.8% Yield. $^1$H NMR (CDCl$_3$) δ 0.64–0.69 (2H, m), 0.88–0.94 (2H, m), 1.04–1.17 (5H, m), 1.62–1.74 (6H, m), 1.80–1.89 (1H, m), 2.80 (2H, d, J=6.6 Hz), 3.81 (3H, s), 4.72 (2H, s), 5.81 (1H, d, J=6.9 Hz), 6.22 (1H, s), 6.33 (1H, t, J=7.1 Hz), 7.40 (1H, d, J=7.2 Hz).

Part E: General Procedure for Preparation of 2-(2-Alkyl-8-(carbomethoxymethyloxy)-3-(substituted methyl)indolizin-1-yl)glyoxylamide 57

These compounds were prepared from 56, according to the procedure described for the synthesis of 34.

Preparation of 2-(3-(Biphenyl-2-ylmethyl)-8-(carbomethoxymethyloxy)-2-methylindolizin-1-yl)glyoxylamide 57a Mp, 150–152° C. 91% Yield. IR ν$_{max}$ (CHCl$_3$) 3502, 3390, 1759, 1695, 1630 cm$^{-1}$. $^1$H NMR (CDCl$_3$) δ 2.40 (3H, s), 3.77 (3H, s), 4.12 (2H, s), 4.71 (2H, s), 5.65 (1H, br.s), 6.23 (1H, d, J=7.4 Hz), 6.44 (1H, d, J=7.6 Hz), 6.64 (1H, br.s), 6.81 (1H, d, J=7.2 Hz), 7.05 (1H, d, J=7.2 Hz), 7.14–7.25 (1H, m), 7.26–7.50 (7H, m). Analyses: Calc'd for C$_{27}$H$_{24}$N$_2$O$_5$.0.2H$_2$O: C, 70.48; H, 5.35; N, 6.09. Found: C, 70.55; H, 5.37; N, 6.10.

Other Preparations:

2-(3-(Biphenyl-2-ylmethyl)-8-(carbomethoxymethyloxy)-2-isopropylindolizin-1-yl)glyoxylamide 57c. Mp, 124–130° C. 48.6% Yield.

2-(2-t-Butyl-8-carbomethoxymethyloxy-3-(o-phenylbenzyl)indlolin-1-yl)glyoxylamide 57e. Mp, 206–207° C. (EtOAc). 77.6% Yield.

2-(8-Carbomethoxymethyloxy-2-cyclopentyl-3-(o-phenylbenzyl)indlolin-1-yl)glyoxylamide 57f. Mp, 119–121° C. (benzene). 77.6% Yield.

2-(8-Carbomethoxymethyloxy-2-ethyl-3-(m-phenylbenzyl)indlolin-1-yl)glyoxylamide 57g. Mp, 204–205° C. (EtOAc). 11.5% Yield.

2-(8-Carbomethoxymethyloxy-2-ethyl-3-(3-phenyl-2-propenyl)indlolin-1-yl)glyoxylamide 57h. Mp, 260–262° C. (EtOAc). 73.7% Yield.

Preparation of 2-(8-Carbomethoxymethyloxy-2-ethyl-3-(3-phenyl-2-propanyl)indlolin-1-yl)glyoxylamide 57i A mixture of the olefin (180 mg, 0.428 m mol) and 10% palladium-coal (13 mg) in ethyl acetate (15 ml) was stirred in hydrogen for 4 hours. The catalyst was filtered and washed with ethyl acetate. The filtrate was concentrated under reduced pressure. The residue was recrystallized from ethyl acetate. Mp, 167° C. 103 mg (56.9%).

2-(8-Carbomethoxymethyloxy-2-cyclopropyl-3-(1-naphthylmethyl)indlolin-1-yl)glyoxylamide 57j. Amorphous. 44.3% Yield. 2-(8-Carbomethoxymethyloxy-3-cyclohexylmethyl-2-cyclopropylindolizin-1-yl) glyoxylamide 57k. Mp, 153–157° C. 53.7% Yield.

Part F: General Prodedure for Preparation of 2-(2-Alkyl-8-(carbomethoxymethyloxy)-3-(substituted methyl)indolizin-1-yl)glyoxylamide 58

These compound was prepared by hydrolysis of 57 with lithium hydroxide cited above.

Other Preparations:

2-(3-(Biphenyl-2-ylmethyl)-8-carboxymethoxyl-2-methylindolizin-1-yl)glyoxylamide 58a Mp, 221–224° C. 62.1% Yield. IR $\nu_{max}$ (nujol) 3448, 3344, 1735, 1635 (sh), 1615 cm$^{-1}$. $^1$H NMR (CDCl$_3$) δ 2.40 (3H, s), 4.14 (2H, s), 4.74 (2H, s), 6.38 (1H, d, J=8.1 Hz), 6.54 (1H, t, J=6.9 Hz), 6.81 (1H, d, J=7.5 Hz), 7.05–7.53 (8H, m). Analyses: Calc'd for C$_{26}$H$_{22}$N$_2$O$_5$.0.5H$_2$O: C, 69.17; H, 5.13; N, 6.20. Found: C, 69.07; H, 5.06; N, 6.17.

2-(3-(Biphenyl-2-ylmethyl)-8-carbomethoxymethyloxy-2-isopropylindolizin-1-yl)glyoxylamide 58c. Mp, 139–141° C. 59% Yield. IR $\nu_{max}$ (CHCl$_3$) 3462, 3382, 3292, 1737, 1686, 1639 cm$^{-1}$. $^1$H NMR (CDCl$_3$) δ 1.32 (6H, d, J=7.0 Hz), 3.42 (1H, sept, J=7.0 Hz), 4.19 (2H, s), 4.59 (2H, s), 6.23 (1H, d, J=7.4 Hz), 6.45 (1H, t, J=7.0 Hz), 6.69 (1H, d, J=7.8 Hz), 6.91 (1H, br.s), 7.03–7.58 (11H, m). Analyses: Calc'd for C$_{28}$H$_{26}$N$_2$O$_5$.1.3H$_2$O: C, 68.09; H, 5.84; N, 5.67. Found: C, 68.02; H, 5.74; N, 5.65.

2-(2-t-Butyl-8-carboxymethoxyl-3-(o-phenylbenzyl)indlolin-1-yl)glyoxylamide 58e

Mp, 221–222° C. (EtOAc). Quantitative yield. IR $\nu_{max}$ (nujol) 3417, 3378, 1732, 1679, 1650, 1542, 1305, 1238 cm$^{-1}$. $^1$H NMR (CDCl$_3$) δ 1.39 (9H, s), 4.30 (2H, s), 4.65 (2H, s), 6.09 (1H, d, J=7.5 Hz), 6.38 (1H, t, J=7.2 Hz), 6.67 (1H, d, J=7.5 Hz), 7.08 (1H, d, J=6.9 Hz), 7.17 (2H, m), 7.2–7.3 (2H, m), 7.35–7.5 (4H, m). Analyses: Calc'd: C$_{29}$H$_{28}$N$_2$O$_5$.0.6C$_6$H$_6$: C, 73.68; H, 5.99; N, 5.27. Found: C, 73.53; H, 6.28; N, 5.04.

2-(8-Carboxymethyloxy-2-cyclopentyl-3-(o-phenylbenzyl)indlolin-1-yl)glyoxylamide 58f Mp, 147–148° C. (EtOAc). 73.4% Yield. IR $\nu_{max}$ (nujol) 3428, 1739, 1655 cm$^{-1}$. $^1$H NMR (CDCl$_3$) δ 1.65 (2H, m), 1.79 (4H, m), 1.97 (2H, m), 3.42 (1H, m), 4.16 (2H, s), 4.69 (2H, s), 6.29 (1H, d, J=7.5 Hz), 6.48 (1H, t, J=6.6 Hz), 6.74 (1H, d, J=8.1 Hz), 7.05 (1H, br.s), 7.07 (1H, d, J=7.2 Hz), 7.11 (1H, dt, J=7.5, 1.8 Hz), 7.18 (1H, br.s), 7.29 (2H, m), 7.4–7.55 (5H, m).

2-(8-Carboxymethyloxy-2-ethyl-3-(m-phenylbenzyl)indlolin-1-yl)glyoxylamide 58g

Mp, 241–244° C. (EtOAc). 73.5% Yield. IR $\nu_{max}$ (nujol) 3314, 3180, 1702, 1600, 1492 cm$^{-1}$. $^1$H NMR (CDCl$_3$+CD$_3$OD) δ 1.26 (3H, t, J=7.3 Hz), 2.93 (2H, q, J=7.2 Hz), 4.33 (2H, s), 4.72 (2H, s), 6.37 (1H, d, J=7.4 Hz), 6.59 (1H, t, J=7.6 Hz), 7.03 (1H, d, J=8.2 Hz), 7.3–7.6 (9H, m).

2-(8-Carboxymethyloxy-2-ethyl-$^3$-(3-phenyl-2-propenyl)indlolin-1-yl)glyoxylamide 58h Mp, 222–224° C. (EtOAc). 71.3% Yield. IR $\nu_{max}$ (nujol) 3429. 3334, 1728, 1644, 1619, 1501 cm$^{-1}$. $^1$H NMR (CDCl$_3$+CD$_3$OD) δ 1.23 (3H, t, J=7.2 Hz), 2.85 (2H, q, J=7.5 Hz), 3.79 (2H, d, J=5.4 Hz), 4.74 (2H, s), 6.23 (1H, dt, J=15.9, 5.4 Hz), 6.30–6.42 (2H, m), 6.67 (1H, t, J=7.5 Hz), 7.2–7.35 (5H, m), 7.65 (1H, d, J=7.2 Hz). Analyses: Calc'd: C$_{23}$H$_{22}$N$_2$O$_5$: C, 67.97; H, 5.46; N, 6.89. Found: C, 67.84; H, 5.50; N, 6.82.

2-(8-Carboxymethyloxy-2-ethyl-3-(3-phenyl-2-propanyl)indlolin-1-yl)glyoxylamide 58i Mp, 215–217° C. 93.1% Yield. IR $\nu_{max}$ (nujol) 3469, 3252, 1703, 1637, 1596, 1535, 1487 cm$^{-1}$. $^1$H NMR (CDCl$_3$) δ 1.17 (3H, t, J=7.8 Hz), 1.91 (2H, m), 2.7–2.9 (6H, m), 4.71 (2H, s), 6.35 (1H, d, J=7.5 Hz), 6.64 (1H, t, J=6.6 Hz), 7.2–7.45 (6H, m). Analyses: Calc'd: C$_{23}$H$_{24}$N$_2$O$_5$.0.4H$_2$O: C, 66.46; H, 6.01; N, 6.74. Found: C, 66.32; H, 5.88; N, 6.72.

2-(8-carboxymethoxyl-2-cyclopropyl-3-(1-naphthylmethyl)indlolin-1-yl)glyoxylamide 58j Mp, 205–207° C. (EtOAc). 70.7% Yield. IR $\nu_{max}$ (nujol) 3439, 3341, 1737, 1648, 1621, 1597, 1495 cm$^{-1}$. $^1$H NMR (CDCl$_3$) δ 0.48 (2H, m), 0.88 (2H, m), 2.13 (1H, m), 4.76 (2H, s), 4.81 (2H, s), 6.42 (1H, d, J=7.2 Hz), 6.55 (1H, t, J=7.2 Hz), 6.30 (1H, br.s), 7.07 (1H, br.s), 7.2–7.3 (2H, m), 7.55–7.7 (2H, m), 7.76 (1H, d, J=7.8 Hz), 7.94 (1H, d, J=6.9 Hz), 8.25 (1H, d, J=8.4 Hz). Analyses: Calc'd: C$_{26}$H$_{22}$N$_2$O$_5$.0.4H$_2$O: C, 69.45; H, 5.11; N, 6.23. Found: C, 69.33; H, 5.14; N, 6.21.

2-(8-carboxymethoxyl-3-cyclohexylmethyl-2-cyclopropylindolizin-1-yl)glyoxylamide 58k Mp, 229–234° C. 79% Yield. IR $\nu_{max}$ (nujol) 3434, 3334, 1731, 1650 (sh), 1620, 1593 cm$^{-1}$. $^1$H NMR (CDCl$_3$) δ 0.41–0.46 (2H, m), 0.91–1.01 (2H, m), 1.08–1.79 (11H, m), 1.89–2.05 (1H, m), 2.85 (2H, d, J=6.6 Hz), 4.73 (2H, s), 6.38 (1H, d, J=7.4 Hz), 6.59 (1H, br.s), 6.71 (1H, t, J=7.2 Hz), 7.00 (1H, br.s), 7.59 (1H, d, J=7.0 Hz).

Part G-1: Preparation of 2-(3-(Biphenyl-2-yl-methyl-8-(carboxymethyloxy)-2-ethylindolizine-1-yl)glyoxylamide Sodium Salt 59a Mp, >250° C. 86% Yield. IR $\nu_{max}$ (nujol) 3240, 1644, 1496, 1409, 1277 cm$^{-1}$.

Other Preparations:

2-(3-Biphenyl-2-ylmethyl-8-(1-methoxycarbonyloxyethoxycarbonylmethoxy)-2-ethylindolizin-1-yl)glyoxylamide 59b 20% Yield. IR $\nu_{max}$ (CHCl$_3$) 3500, 3390, 1764, 1731, 1697, 1630 cm$^{-1}$.

2-(3-Biphenyl-2-ylmethyl-2-ethyl-8-(1-isopropyloxycarbonyloxyethoxycarbonylmethoxy)indolizin-1-yl)glyoxylamide 59c. 44% Yield. IR $\nu_{max}$ (CHCl$_3$) 3674, 3500, 3390, 1755, 1693, 1631 cm$^{-1}$.

2-(3-(Biphenyl-2-yl-methyl-8-(t-butoxycarbonylmethyloxycarbonylmethyloxy)-2-ethylindolizine-1-yl)glyoxylamide 59d. Mp, 102–104 C. 36%.Yield. IR $\nu_{max}$ (nujol) 3408, 3306, 3169, 1771, 1692, 1672, 1630, 1603 cm$^{-1}$.

2-(3-(Biphenyl-2-yl-methyl-8-(1-cyclohexyloxycarbonylethyloxycarbonylmethyloxy)-2-ethylindolizine-1-yl)glyoxylamide 59e. Mp, 80–82° C. (dec). 57% Yield. IR $\nu_{max}$ (nujol) 3471, 3356, 1753, 1693, 1630, 1496, 1261, 1077 cm$^{-1}$.

2-(3-Biphenyl-2-ylmethyl-8-(1-cyclopentyloxycarbonyloxymethyloxy-carbamoanecarbonyl-2-ethylindolizin-1-yl)glyoxylamide 59f. Mp, 80–85° C. 35% Yield. IR $\nu_{max}$ (CHCl$_3$) 3666, 3498, 3390, 1754, 1694, 1629 cm$^{-1}$.

2-(3-Biphenyl-2-ylmethyl-8-(1-cyclopentyloxycarbonyloxyethyloxycarbonylmethyloxy)-2-ethylindolizin-1-yl)glyoxylamide 59g. Mp, 74–80° C. 25% Yield. IR $\nu_{max}$ (CHCl$_3$) 3674, 3500, 3390, 1760 (sh), 1745, 1695, 1628 cm$^{-1}$.

2-(3-Biphenyl-2-ylmethyl-2-ethyl-8-(1-methylcyclopentyloxycarbonylethyloxycarbonyl-methyloxy)-indolizin-1-yl)glyoxylamide 59h. 15.7% Yield. IR $\nu_{max}$ (CHCl$_3$) 3500, 3390, 1772, 1737, 1694, 1631 cm$^{-1}$.

2-(3-(Biphenyl-2-yl-methyl)-2-ethyl-8-(2-morpholinoethyloxycarbonylmethyloxy)indolizine-1-yl)glyoxylamide 59i. Mp, 113–120° C. (dec). 75% Yield. IR $\nu_{max}$ (nujol) 3367, 1754, 1679, 1628, 1535, 1494, 1309, 1197 cm$^{-1}$.

2-(3-(Biphenyl-2-yl-methyl)-8-(carboxymethyloxy)-2-ethylindolizine-1-yl)glyoxylamide diglycolate 59j Mp, 185–188° C. 59% Yield. IR $\nu_{max}$ (nujol) 3441, 3228, 1762, 1724, 1685, 1643, 1501, 1200 cm$^{-1}$.

2-(3-(Biphenyl-2-yl-methyl)-2-ethyl-8-(2-oxopropyloxycarbonylmethoxy)indolizine-1-yl)glyoxylamide 59k.

Mp, 159–162 0C. 77% Yield. IR $\nu_{max}$ (nujol) 3417, 3302, 3169, 1727, 1691, 1672, 1630, 1601, 1306 cm$^{-1}$.

Part G-2: General Procedure for Preparation of 2-(3-(Biphenyl-2-ylmethyl)-2-ethyl-8-(substituted methyloxy)indolizin-1-yl)glyoxylamide 59l-p 2-(3-(Biphenyl-2-ylmethyl)-2-ethyl-8-(hydroxymethyloxy)indolizin-1-yl)glyoxylamide 36d was treated with the same procedure of the preparation of 51 from 50.

Other Preparations:

2-(3-(Biphenyl-2-yl-methyl)-2-ethyl-8-(1-tritytretrazol(-5-yl)methyloxy)indolizine-1-yl)glyoxylamide 59l
Mp, 119–121° C. 66% Yield. IR $\nu_{max}$ (nujol) 3439, 3363, 3166, 1734, 1685, 1607, 1495, 1249 cm$^{-1}$.

2-(3-(Biphenyl-2-yl-methyl)-2-ethyl-8-(1H-tetracol-5-ylmethyloxy)indolizine-1-yl)glyoxylamide 59m. Mp, 206–209° C. (dec). 60% Yield. IR $\nu_{max}$ (nujol) 3488, 3437, 3322, 1681, 1631, 1530, 1496, 1309 cm$^{-1}$.

2-(3-Biphenyl-2-ylmethyl-2-methyl-8-(pyridin-2-ylmethoxy)-indolizin-1-yl)-glyoxylamide 59n. Mp, 196–197° C. (hexane-AcOEt). 4.2% Yield.

2-(3-Biphenyl-2-ylmethyl-2-methyl-8-(pyridin-4-ylmethoxy)-indolizin-1-yl)-glyoxylamide 59o. Mp, 195–197° C. (hexane-AcOEt). 3.4% Yield.

2-(3-Biphenyl-2-ylmethyl-2-methyl-8-(quinolin-2-ylmethoxy)-indolizin-1-yl)-glyoxylamide 59p. Mp, 165–167° C. (hexane-AcOEt). 3.4% Yield.

Example 7

Part A: Preparation of 2-Ethyl-7-methoxyindolizine 61a and 2-Cyclopropyl-7-methoxyindolizine 61b 4-Methoxypicoline was treated with the same procedure of the preparation of 45 from 44.

61a: 29.4% Yield. IR $\nu_{max}$ (KBr) 2962, 1648 cm$^{-1}$. $^1$H NMR (CDCl$_3$) δ 1.27 (3H, t, J=7.2 Hz), 2.67 (2H, q, J=7.4 Hz), 3.77 (3H, s), 6.06 (1H, s), 6.14 (1H, dd, J=7.6, 2.6 Hz), 6.52 (1H, d, J=2.4 Hz), 6.94 (1H, s), 7.66 (1H, d, J=7.6 Hz). m/z 175.0982 [M]$^+$.

61b: Mp, 101–102° C. (hexane). 27.3% Yield. IR $\nu_{max}$ (KBr) 3073, 3059, 2994, 2963, 2939, 2829, 1649 cm$^{-1}$. $^1$H NMR (CDCl$_3$) δ 3.76 (3H, s), 5.12 (1H, s), 6.13 (1H, dd, J=2.7, 7.2 Hz), 6.49 (1H, d, J=2.7 Hz), 6.95 (1H, d, J=1.2 Hz), 7.64 (1H, d, J=7.2 Hz). Analyses: Calc'd for C$_{12}$Hl$_3$NO: C, 76.98; H, 7.00; N, 7.48. Found: C, 76.81; H, 7.09; N, 7.47.

Part B: Preparation of 2-Alkyl-7-methoxy-3-(substituted carbonyl)indolizine 62

Indolizine compound 61 was converted to 62 by the same procedure cited for the preparation of 18 from 17

3-Benzoyl-2-ethyl-7-methoxyindolizine 62a Mp, 105–106° C. (hexane). 70.5% Yield. IR $\nu_{max}$ (KBr) 3057, 2966, 2926, 2868, 1645 cm$^{-1}$. $^1$H NMR (CDCl$_3$) δ 1.02 (3H, t, J=7.5 Hz), 2.17 (2H, q, J=7.5 Hz), 3.88 (3H, s), 6.23 (1H, s), 6.54 (1H, dd, J=2.7, 7.8 Hz), 6.72 (1H, d, J=2.1 Hz), 7.40–7.49 (3H, m), 7.56–7.60 (2H, m), 9.67 (1H, d, J=7.5 Hz). Analyses: Calc'd for C$_{18}$H$_{17}$NO$_2$.0.5H$_2$O: C, 74.98; H, 6.29; N, 4.86. Found: C, 74.77; H, 6.10; N, 5.02.

Other Preparations:

2-Cyclopropyl-7-methoxy-3-(o-phenylbenzoyl)indolizine 62b. A yellow oil. Quantitative yield. $^1$H NMR (CDCl$_3$) δ 0.48 –0.69 (2H, m), 1.11 (1H, m), 3.82 (3H, s), 5.71 (1H, s), 6.45 (1H, dd, J=2.8, 7.6 Hz), 6.57 (1H, d, J=2.6 Hz), 7.15–7.54 (9H, m), 9.76 (1H, d, J=7.6 Hz).

2-Ethyl-7-methoxy-3-(o-phenylbenzoyl)indolizine 62c Mp, 140–141° C. (ether). 90.2% Yield.

3-Cyclohexylcarbonyl-2-ethyl-7-methoxyindolizine 62d Mp, 112–113° C. (hexane). 41.1% Yield.

Part C: Preparation of 2-Alkyl-7-methoxy-3-(substituted methyl)indolizine 63

Indolizine compound 62 was converted to 63 by the same procedure cited for the preparation of 48 from 47.

Other Preparations:

3-Benzyl-2-ethyl-7-methoxyindolizine 63a Amorphous solid. 22.0% Yield. IR $\nu_{max}$ (KBr) 3002, 2956, 2926, 1646 cm$^{-1}$.

2-Cyclopropyl-7-methoxy-3-(o-phenylbenzyl)indolizine 63b
Mp, 109–110° C. (hexane). 44.3% Yield.

2-Ethyl-7-methoxy-3-(o-phenylbenzyl)indolizine 63c.
Mp, 100–101° C. (hexane). 39.2% Yield. IR $\nu_{max}$ (KBr) 2964, 2927, 1645 cm$^{-1}$.

3-Cyclohexylmethyl-2-ethyl-7-methoxyindolizine 63d
Amorphous yellow solid. 48.2% Yield. IR $\nu_{max}$ (CHCl$_3$) 2988, 2956, 2920, 2846, 1645 cm$^{-1}$.

Part D: Preparation of (2-Alkyl-7-methoxy-3-(substituted methyl)indolizin-1-yl)glyoxylamide 64

Indolizine compound 63 was converted to 64 by the same procedure cited for the preparation of 49 from 48.

Other Preparations:

2-(3-Benzyl-2-ethyl-7-methoxyindolizin-1-yl)glyoxylamide 64a
Amorphous solid. 78.9% Yield. IR $\nu_{max}$ (KBr) 3500, 3386, 3004, 2962, 1689, 1644, 1601 cm$^{-1}$. $^1$H NMR (CDCl$_3$) δ 1.23 (3H, dt, J=7.5, 1.2 Hz), 2.98 (2H, q, J=7.8 Hz), 3.87 (3H, s), 4.21 (2H, s), 5.57 (1H, br.s), 6.42 (1H, dd, J=2.7, 7.5 Hz), 6.79 (1H, br.s), 7.08 (1H, d, J=6.9 Hz), 7.21 (3H, m), 7.51 (1H, d, J=7.5 Hz), 7.82 (1H, d, J=2.7 Hz).

2-(2-Cyclopropyl-7-methoxy-3-(o-phenylbenzyl)indolizin-1-yl)glyoxylamide 64b. Mp, 194–195° C. (benzene-hexane). 50.1% Yield.

2-(2-Ethyl-7-methoxy-3-(o-phenylbenzyl)indolizin-1-yl)glyoxylylamide 64c. Mp, 101–106° C. (benzene-hexane). 75.9% Yield.

2-(3-Cyclohexylmethyl-2-ethyl-7-methoxyindolizin-1-yl)glyoxylamide 64d. Mp, 178–180° C. (THF-hexane). 50.4% Yield.

Part E: Preparation of 2-(2-Alkyl-7-hydroxy-3-(substituted methyl)indolizin-1-yl)glyoxylamide 65

Indolizine compound 64 was converted to 65 by the same procedure cited for the preparation of 50 from 49.

Other Preparations:

2-(3-Benzyl-2-ethyl-7-hydroxyindolizin-1-yl)glyoxylamide 65a
BBr$_3$ method. An amorphous solid: 49% Yield. $^1$H NMR (CDCl$_3$) δ 1.11 (3H, t, J=7.2 Hz), 2.86 (2H, t, J=7.2 Hz), 4.24 (2H, s), 6.52 (1H, dd, J=2.1, 7.5 Hz), 7.08–7.30 (6H, m), 7.43 (1H, d, J=2.4 Hz), 7.51 (1H, s), 7.92 (1H, d, J=6.9 Hz), 7.98 (1H, s).

2-(2-Cyclopropyl-7-hydroxy-3-(o-phenylbenzyl)indolizin-1-yl)glyoxylamide 65b. Amorphous solid. 12.6% Yield. $^1$H NMR (CDCl$_3$) δ 0.50–0.54 (2H, m), 0.86–0.91 (2H, m), 2.26 (1H, m), 4.21 (2H, s), 6.40 (1H, dd, J=2.4, 7.2 Hz), 6.79 (1H, d, J=8.0 Hz), 7.08–7.51 (9H, m), 7.67 (1H, d, J=2.8 Hz).

2-(2-Ethyl-7-hydroxy-3-(o-phenylbenzyl)indolizin-1-yl)glyoxylylamide 65c. Mp, 125–129° C. (benzene-hexane). 36.9% Yield.

2-(3-Cyclohexylmethyl-2-ethyl-7-hydroxyindolizin-1-yl)glyoxylamide 65d
Amorphous solid. 28.0% Yield. $^1$H NMR (CDCl$_3$+CD$_3$OD) δ 1.00–1.20 (5H, m), 1.17 (3H, t, J=7.2 Hz), 1.44–1.76 (6H, m), 2.64 (2H, d, J=7.2 Hz), 2.83 (2H, m), 6.60 (1H, dd, J=2.1, 6.9 Hz), 7.49 (1H, br.s), 7.77 (1H, d, J=7.2 Hz).

Part F: General Procedure for Preparation of 2-(2-Alkyl-7-(3-carbethoxypropyloxy)-3-(substituted methyl)indolizin-1-yl)glyoxylamide 66

Indolizine compound 65 was converted to 66 by the same procedure cited for the preparation of 51 from 50.

Other Preparations:

2-(3-Benzyl-7-(3-carbethoxypropyloxy)-2-ethylindolizin-1-yl)glyoxylamide 66a

Mp, 146–149° C. 54.% Yield. IR $v_{max}$ (KBr) 3430, 3170, 2958, 2928, 1731, 1674, 1645 cm$^{-1}$. $^1$H NMR (CDCl$_3$) δ 1.22 (3H, t, J=7.5 Hz), 1.25 (3H, t, J=7.2 Hz), 2.13 (2H, m), 2.49 (2H, q, J=7.2 Hz), 2.97 (2H, q, J=7.5 Hz), 4.08 (2H, t, J=6.3 Hz), 4.14 (2H, q, J=7.2 Hz), 4.21 (2H, s), 5.56 (1H, br.s), 6.40 (1H, dd, J=2.7, 7.2 Hz), 6.78 (1H, br.s), 7.08 (2H, d, J=7.8 Hz), 7.21–7.29 (3H, m), 7.50 (1H, d, J=7.2 Hz), 7.78 (1H, d, J=2.7 Hz). Analyses: Calc'd for C$_{25}$H$_{28}$N$_2$O$_3$.0.2H$_2$O: C, 68.23; H, 6.50; N, 6.37. Found: C, 68.30; H, 6.52; N, 6.52.

2-(7-(3-Carbethoxypropyloxy)-2-cyclopropyl-3-(o-phenylbenzyl)indolizin-1-yl)glyoxylamide 66b. Amorphous solid. 84.2% Yield. $^1$H NMR (CDCl$_3$) δ 0.47–0.52 (2H, m), 0.85–0.91 (2H, m), 1.25 (3H, t, J=6.9 Hz), 2.08–2.17 (3H, m), 2.48 (2H, td, J=7.2 Hz), 4.06 (2H, t, J=6.3 Hz), 4.14 (2H, q, J=6.9 Hz), 4.23 (2H, s), 5.52 (1H, br.s), 6.35 (1H, dd, J=2.7, 7.5 Hz), 6.58 (1H, br.s), 6.67 (1H, d, J=7.2 Hz), 7.11–7.54 (9H, m), 7.72 (1H, d, J=2.1 Hz).

2-(7-(3-Carbethoxypropyloxy)-2-ethyl-3-(o-phenylbenzyl)indolizin-1-yl)glyoxylylamide 66c. Mp, 131–133° C. (benzene-hexane). 70.9% Yield.

2-(7-(3-Carbethoxypropyloxy)-3-cyclohexylmethyl-2-ethyl-hydroxyindolizin-1-yl)glyoxylamide 66d. Mp, 150–151° C. (THF-hexane). 87.0% Yield.

Part G: General Procedure for Preparation of 2-(2-Alkyl-7-(3-carboxypropyloxy)-3-(substituted methyl)indolizin-1-yl)glyoxylamide 67

Indolizine compound 66 was converted to 67 by the same procedure cited for the preparation of 52 from 51.

Other Preparations:

2-(3-Benzyl-7-(3-carboxylpropyloxy)-2-ethylindolizin-1-yl)glyoxylamide 67a

Mp, 178–183° C. (dec.). 77.0% Yield. IR $v_{max}$ (KBr) 3700–2400, 3085, 2925, 1710, 1644 cm$^{-1}$. $^1$H NMR (CDCl$_3$) δ 1.22 (3H, t, J=7.5 Hz), 2.14 (2H, t, J=6.9 Hz), 2.97 (2H, q, J=7.5 Hz), 4.11 (2H, t, J=6.3 Hz), 4.20 (2H, s), 6.38 (1H, br.s), 6.41 (1H, dd, J=7.2, 2.4 Hz), 6.96 (2H, br.s), 7.08 (2H, d, J=6.9 Hz), 7.23–7.26 (3H, m), 7.51 (1H, d, J=7.5 Hz), 7.75 (1H, d, J=2.7 Hz). Analyses: Calc'd for C$_{23}$H$_{24}$N$_2$O$_3$.0.3H$_2$O: C, 66.75; H, 5.99; N, 6.77. Found: C, 66.71; H. 5.91; N, 6.77.

2-(7-(3-Carboxypropyloxy)-2-cyclopropyl-3-(o-phenylbenzyl)indolizin-1-yl)glyoxylamide 67b. Mp, 112–121° C., (dec.). 69.6% Yield. IR $v_{max}$ (KBr) 3700–2400, 3081, 3019, 2927, 1710, 1644 cm$^{-1}$. $^1$H NMR (CDCl$_3$) δ 0.50 (2H, m), 0.88 (2H, m), 2.49 (2H, t, J=6.3 Hz), 4.10 (2H, m), 4.23 (2H, s), 6.37 (1H, d, J=6.9 Hz), 6.67 (1H, d, J=7.5 Hz), 7.11–7.54 (9H, m), 7.74 (1H, s). Analyses: Calc'd for C$_{30}$H$_{28}$N$_2$O$_5$.1.2H$_2$O: C, 69.54; H, 5.91; N, 5.41. Found: C, 69.43; H, 5.93; N, 5.35.

2-(7-(3-Carboxypropyloxy)-2-ethyl-3-(o-phenylbenzyl)indolizin-1-yl)glyoxylamide 67c Mp, 112–116° C. (dec.). 67.0% Yield. IR $v_{max}$ (KBr) 3700–2400, 2967, 2931, 1709, 1644 cm$^{-1}$. $^1$H NMR (CDCl$_3$) δ 1.19 (3H, t, J=7.5 Hz), 2.17 (2H, br.t), 2.53 (2H, br.t), 2.92 (2H, q, J=7.2 Hz), 4.07 (2H, br.s), 6.35 (1H, dd, J=1.8, 7.5 Hz), 6.79 (1H, d, J=7.5 Hz), 6.98 (1H, br.s), 7.12–7.31 (4H, m), 7.42–7.53 (5H, m), 7.70 (1H, br.s).

Analyses: Calc'd for C$_{29}$H$_{28}$N$_2$O$_5$.0.9H$_2$O: C, 69.56; H, 6.00; N, 5.59. Found: C, 69.57; H, 5.87; N, 5.44.

2-(7-(3-Caboxypropyloxy)-3-cyclohexylmethyl-2-ethyl-hydroxyindolizin-1-yl)glyoxylamide 67d Mp, 201–202.5° C. 92.4% Yield. IR $v_{max}$ (KBr) 3700–2400, 2923, 2849, 1716, 1646 cm$^{-1}$. $^1$H NMR (CDCl$_3$) δ 0.95–1.19 (5H, m), 1.17 (3H, t, J=7.2 Hz), 1.43–1.75 (6H, m), 2.14 (2H, m), 2.53 (2H, t, J=7.2 Hz), 2.65 (2H, d, J=6.9 Hz), 2.86 (2H, q, J=7.5 Hz), 4.12 (2H, t, J=6.3 Hz), 6.57 (2H, dd, J=2.4, 7.5 Hz), 7.68 (1H, d, J=2.4 Hz), 7.75 (1H, d, J=7.5 Hz). Analyses: Calc'd for C$_{23}$H$_{30}$N$_2$O$_5$.0.3H$_2$O: C, 65.79; H, 7.34; N, 6.67. Found: C, 65.83; H, 7.36; N, 6.78.

Part H-1: Preparation of 2-(7-(Carboxymethylenoxy)-2-ethyl-3-(o-phenylbenzyl)indolizin-1-yl)glyoxylamide 69, 70, 71

1) Indolizine compound 50a or 65c was converted to 68 by the same procedure cited for the preparation of 51 from 50.

Other Preparations:

2-(8-(3-Carbomethoxyproyloxy)-2-ethyl-3-(o-phenylbenzyl)indolizin-1-yl)glyoxylamide 68a Mp, 126–127° C. 42% Yield. IR $v_{max}$ (nujol) 3396, 3221, 1737, 1725, 1698, 1639, 1310, 1188 cm$^{-1}$. $^1$H NMR (CDCl$_3$) δ 1.13–1.34 (6H, m), 2.17 (2H, quint., J=6.9 Hz), 2.54 (2H, t, J=7.4 Hz), 2.79 (2H, q, J=7.6 Hz), 4.03–4.20 (6H, m), 5.66 (1H, br.s), 6.31 (1H, d, J=7.4 Hz), 6.46 (1H, t, J=7.2 Hz), 6.70–6.84 (2H, m), 7.02 (1H, d, J=6.4 Hz), 7.08–7.20 (1H, m), 7.21–7.35 (2H, m), 7.37–7.58 (5H, m). Analyses: Calc'd for C$_{31}$H$_{32}$N$_2$O$_5$.0.5H$_2$O: C, 71.38; H, 6.38; N, 5.37. Found: C, 71.12; H, 6.57; N, 5.00.

2-(7-(Carboethoxymethyloxy)-2-ethyl-3-(o-phenylbenzyl)indolizin-1-yl)glyoxylamide 68b.

Mp, 119–121° C. (THF-hexane). 86.6% Yield. IR $v_{max}$ (KBr) 3434, 3356, 3180, 3060, 2969, 2929, 1765, 1682, 1643, 1627 cm$^{-1}$. $^1$H NMR (CDCl$_3$) δ 1.20 (3H, t, J=7.5 Hz), 1.32 (3H, t, J=7.2 Hz), 2.94 (2H, q, J=7.5 Hz), 4.09 (2H, s), 4.29 (2H, q, J=7.2 Hz), 4.66 (2H, s), 5.50 (1H, br.s), 6.48 (1H, dd, J=2.4, 7.5 Hz), 6.77 (1H, br.s), 6.79 (1H, d, J=7.8 Hz), 7.75 (1H, d, J=7.8 Hz). Analyses: Calc'd for C$_{29}$H$_{28}$N$_2$O$_5$.0.3H$_2$O: C, 71.09; H, 5.88; N, 5.72. Found: C, 71.11; H, 6.02; N, 5.86.

2-(7-(5-Carboethoxypentyloxy)-2-ethyl-3-(o-phenylbenzyl)indolizin-1-yl)glyoxylamide 68c.

Mp, 122–123° C. (MeOH-Et$_2$O-hexane). 81.0% Yield. IR $v_{max}$ (KBr) 3406, 3351, 3207, 2967, 2931, 2871, 1724, 1684, 1645 cm$^{-1}$. $^1$H NMR (CDCl$_3$) δ 1.20 (3H, t, J=7.5 Hz), 1.25 (3H, t, J=7.2 Hz), 1.77–1.85 (4H, m), 2.37 (2H, t, J=6.9 Hz), 2.93 (2H, q, J=7.5 Hz), 4.03 (2H, t, J=5.8 Hz), 4.08 (2H, s), 4.12 (2H, q, J=7.5 Hz), 5.57 (1H, br.s), 6.35 (1H, dd, J=2.7, 7.5 Hz), 6.76 (1H, br.s), 6.80 (1H, d, J=7.8 Hz), 7.12–7.32 (4H, m), 7.40–7.54 (5H, m). Analyses: Calc'd for C$_{32}$H$_{34}$N$_2$O$_5$.0.3H$_2$O: C, 72.24; H, 6.55; N, 5.27. Found: C, 72.16; H, 6.55; N, 5.40.

2-(3-(Biphenyl-2-yl-methyl)-8-(carboxypropyloxy)-2-ethylindolizine-1-yl)glyoxylamide 69a Mp, 185–187° C. 71% Yield. IR $v_{max}$ (nujol) 3475, 1729, 1666, 1628, 1497, 1308 cm$^{-1}$. $^1$H NMR (CDCl$_3$) δ 1.19 (3H, t, J=7.5 Hz), 2.19 (2H, quint., J=7.3 Hz), 2.51 (2H, t, J=7.5 Hz), 2.80 (2H, q, J=7.5 Hz), 4.04–4.16 (4H, m), 6.34 (1H, d, J=7.5 Hz), 6.48 (1H, t, J=7.2 Hz), 6.79 (1H, d, J=7.8 Hz), 6.94–7.06 (2H, m), 7.10–7.19 (1H, m), 7.22–7.34 (2H, m), 7.38–7.55 (6H, m). Analyses: Calc'd for C$_{29}$H$_{28}$N$_2$O$_5$.0.3H$_2$O: C, 71.09; H, 5.88; N, 5.72. Found: C, 70.87; H, 5.83; N, 5.75.

2-(7-(Carboxymethyloxy)-2-ethyl-3-(o-phenylbenzyl)
indolizin-1-yl)glyoxylamide 69b
Mp, 226° C. (dec.). 81.0% Yield.
2-(7-(5-Carboxypentyloxy)-2-ethyl-3-(o-phenylbenzyl)
indolizin-1-yl)glyoxylamide 69c
Mp, 84–94° C. (dec.). 72.0% Yield.
2-(3-(Biphenyl-2-yl-methyl)-8-(carboxyethyloxy)-2-
ethylindolizine-1-yl)glyoxylamide 70a. Mp, 185–187° C. 11% Yield. IR $v_{max}$ (nujol) 3388, 3215, 1730, 1644, 1600, 1585, 1498 cm$^{-1}$. $^1$H NMR (d$_6$-DMSO) δ 0.99 (3H, t, J=7.5 Hz), 2.63 (2H, q, J=7.2 Hz), 2.81 (2H, t, J=6.9 Hz), 4.16 (2H, s), 4.23 (2H, t, J=6.9 Hz), 6.56–6.63 (2H, m), 6.67 (1H, t, J=7.2 Hz), 7.13–7.22 (1H, m), 7.24–7.34 (3H, m), 7.35–7.49 (2H, m), 7.50–7.59 (4H, m), 7.63 (1H, br.s).

Other Preparations:

2-(7-(2-Carboethoxyethyloxy)-2-ethyl-3-(o-phenylbenzyl)
indolizin-1-yl)glyoxylamide 70b Propiolactone (25 mg, 0.336 m mol) was added dropwise to a solution of 65c (133.7 mg, 0.336 m mol) and potassium t-butoxide (37.6 mg, 0.336 m mol) in tetrahydrofuran (4 ml) under nitrogen. The mixture was stirred for 21 hr. Water was added. The mixture was washed with ethyl acetate. The aqueous phase was acidified with hydrochloric acid. The precipitate was collected with filtration to give 70b, 96.2 mg (60.9%). Mp, 99–108° C. (dec.). IR n$_{max}$ (KBr) 3700–2400, 3182, 2968, 2931, 1719, 1677, 1644 cm$^{-1}$. $^1$H NMR (CDCl$_3$) δ 1.19 (3H, t, J=7.5 Hz), 2.80 (2H, t, J=6.3 Hz), 2.92 (2H, q, J=7.5 Hz), 4.08 (2H, s), 4.30 (2H, t, J=6.3 Hz), 6.35 (1H, dd, J=2.7, 7.8 Hz), 6.84 (1H, d, J=7.8 Hz), 7.12–7.53 (9H, m), 7.72 (1H, d, J=2.7 Hz). Analyses: Calc'd for C$_{28}$H$_{26}$N$_2$O$_5$.1.2H$_2$O: C, 68.34; H, 5.82; N, 5.69. Found: C, 68.40; H, 5.76; N, 5.43.

2-(3-(Biphenyl-2-yl-methyl)-8-(2-carbomethoxyethyloxy)-
2-ethylindolizine-1-yl)glyoxylamide 70c Mp, 159–162 C. 6% Yield. IR $v_{max}$ (nujol) 3434, 3323, 1739, 1709, 1621, 1497 cm$^{-1}$. $^1$H NMR (CDCl$_3$) δ 1.18 (3H, t, J=7.5 Hz), 2.79 (2H, q, J=7.5 Hz), 2.89 (2H, t, J=6.3 Hz), 3.73 (3H, s), 4.11 (2H, s), 4.36 (2H, t, J=6.3 Hz), 5.45 (1H, br.s), 6.36 (1H, d, J=7.8 Hz), 6.48 (1H, t, J=7.2 Hz), 6.70 (1H, br.s), 6.78 (1H, d, J=7.5 Hz), 7.03 (1H, d, J=6.9 Hz), 7.11–7.19 (1H, m), 7.22–7.33 (2H, m), 7.39–7.55 (5H, m). Analyses: Calc'd for C$_{29}$H$_{28}$N$_2$O$_5$.0.3H$_2$O: C, 71.09; H, 5.88; N, 5.72. Found: C. 70.93; H, 6.05; N, 5.50.

Part H-2: Preparation of 2-(7-(3-Carbethoxypropyloxy)-2-
ethyl-3-(o-phenylbenzyl)indolizin-1-yl)acetamide 71a Borane-t-butylamine complex (125 mg, 1.44 m mol) was added to a mixture of aluminumtrichloride (13 mg, 0.097 m mol) in toluene (10 ml) with cooling in ice. The mixture was stirred at 0° C. for 10 min. A solution of the glyoxylamide (66c, 246 mg, 0.48 m mol) in toluene (5 ml) was added to the solution. The solution was heated at 60° C. for 2 hours. After cooling the solution was poured to ice-cold dilute hydrochloric acid. The mixture was extracted with dichloromethane. The extracts were washed with water, dried (Na$_2$SO$_4$) and concentrated under reduced pressure. The residue was chromatographed on silica gel in ethyl acetate: hexane (4:1) and recrystallized from hexane, 190 mg (79.4%). Mp, 128–130° C.

IR $v_{max}$ (KBr) 3458, 3132, 2964, 2932, 1730, 1682, 1648 cm$^{-1}$. $^1$H NMR (CDCl$_3$) δ 1.11 (3H, t, J=7.5 Hz), 1.26 (3H, t, J=7.2 Hz), 2.10 (2H, m), 2.48 (2H, t, J=7.2 Hz), 2.59 (2H, q, J=7.5 Hz), 3.64 (2H, s), 3.94 (2H, t, J=6.3 Hz), 4.10 (2H, s), 4.14 (1H, q, J=7.2 Hz), 5.42 (1H, br.s), 5.63 (1H, br.s), 6.06 (1H, dd, J=7.5, 2.4 Hz), 6.44 (1H, d, J=2.4 Hz), 6.68 (1H, d, J=7.5 Hz), 7.07–7.51 (9H. m). Analyses: Calc'd for C$_{31}$H$_{34}$N$_2$O$_4$.0.6H$_2$O: C, 73.09; H, 6.96; N, 5.50. Found: 73.05; H, 7.00; N, 5.49.

Preparation of
2-(7-(3-Carboxypropyloxy)-2-ethyl-3-(o-phenylbenzyl)
indolizin-1-yl)acetamide 71b
Mp, 105–120° C. (dec.). 62.0% Yield.

Example 8

Part A: Preparation of Diethyl 2-(3-benzyloxypyridinium)-
3-thioniumhept-4-thia-2-enoate 73

A solution of benzyloxypyridine (21.73 g, 0.117 mole) and ethyl bromoacetate (19.6 g, 0.117 mole) in benzene (85 ml) was stirred at 65° C. for 2 hours and concentrated under reduced pressure. The residue was washed with ethyl acetate. A solution of aqueous sodium hydroxide (11.80 g, 0.295 mole, 35 ml) was added dropwise to a solution of the residue, carbon disulfide (10.8 g, 0.142 mole), water (24 ml) and ethanol (120 ml). The mixture was stirred for 30 min. Ethyl acrylate (11.8 g, 0.118 mole) was added dropwise. The mixture was stirred for 1 hour. Ice-water was added. The solid was collected by filtration, washed with water and dried (10.9 g, 20.8%) and recrystallized from chloroform-ether. Mp, 162–164° C.

IR $v_{max}$ (nujol) 1719, 1644 cm$^{-1}$. $^1$H NMR (CDCl$_3$) δ 1.16 (3H, t, J=6.9 Hz), 1.26 (3H, t, J=7.2 Hz), 2.80 (2H, t, J=7.5 Hz), 3.58 (2H, t, J=7.5 Hz), 4.13 (2H, q, J=6.9 Hz), 4.15 (2H, q, J=7.2 Hz), 5.21 (2H, s), 7.42 (5H, s), 7.73 (1H, dd, J=9.0, 6.0 Hz), 7.87 (1H, ddd, J=8.7, 2.4, 1.2 Hz), 8.12 (1H, dt, J=6.0, 1.2 Hz), 8.22 (1H, dd, J=2.1, 0.9 Hz). Analyses: Calc'd for C$_{22}$H$_{25}$NO$_5$S$_2$.0.5CHCl$_3$.0.3H$_2$O: C, 57.51; H, 5.63; N, 3.05; S, 13.97; Cl, 1.16. Found: C, 57.59; H, 5.52; N, 3.18; S, 14.08; Cl, 1.14.

Part B: Preparation of Triethyl 8- and 6-Benzyloxy-1,3-
dicarbethoxy-2-(2-carbethoxyethylthio)indolizine 74a+74b A solution of ethyl bromoacetate (2.70 g, 16.2 m mol) and the salt (73, 6.03 g, 13.5 m mol) in chloroform (40 ml) was allowed to stand for 3 days and cooled in ice. A solution of DBU (2.47 g, 16.2 m mol) and chloranil (3.32 g, 13.5 m mol) were added. The mixture was stirred at 0° C. for 6 hours and chromatographed on silica gel (120 g) in chloroform to give a ca. 10:1 mixture of 62a and 62b, (6.0 g, 89.1%) as an oil.

Part C: Preparation of Diethyl 8- and 6-Benzyloxy-1,3-
dicarbethoxy-2-mercaptoindolizine 75a and 75b Potassium t-butoxide (2.73 g, 24.3 m mol) was added in small portions to a solution of the ester (74a+b 9.88 g, 19.8 m mol) in DMF (25 ml) with cooling in ice. The mixture was stirred at 50° C. for 5 hours. Ice-water and then dilute hydrochloric acid were added. The mixture was extracted with ethyl acetate. The extracts were washed with water, dried (Na$_2$SO$_4$) and concentrated under reduced pressure. The residue was chromatographed on silica gel (200 g) in hexane:ethyl acetate (2:1). Both fractions of larger and smaller Rf values were crystallized from benzene-hexane.

Preparation of 75a: The fraction of the larger Rf value: Mp, 125–127° C. 1.12 g (16.7%). IR $v_{max}$ (nujol) 1661, 1508 cm$^{-1}$. $^1$H NMR (CDCl$_3$) δ 1.46 (3H, t, J=6.9 Hz), 1.48 (3H, t, J=7.5 Hz), 4.42 (2H, q, J=6.9 Hz), 4.46 (2H, q, J=7.2 Hz), 5.09 (2H, s), 7.04 (1H, s), 7.15 (1H, dd, J=9.9, 2.4 Hz), 7.3–7.55 (5H, m), 8.09 (1H, dd, J=9.6, 0.6 Hz), 9.41 (1H, s). Analyses: Calc'd for C$_{21}$H$_{21}$NO$_5$S: C, 63.14; H, 5.30; N, 3.51; S, 8.03. Found: C, 62.98; H, 5.42; N, 3.50; S, 7.97.

Preparation of 75b: The fraction of the smaller Pf value: Mp, 81–82° C. 4.59 g (58.1%). IR $v_{max}$ (nujol) 1686, 1655, 1543, 1493 cm$^{-1}$.

Part D: Preparation of Diethyl 8-Benzyloxy-1,3-
dicarbethoxy-2-methylthioindolizine 76

76: 60% Sodium hydride (76 mg) was added to a solution of the thiol (75a, 690 mg, 1.73 m mol) in DMF (4 ml) with cooling in ice under nitrogen. A solution of iodomethane (295 mg, 2.08 m mol) in DMF (1 ml) was added dropwise to the mixture with cooling in ice. The mixture was stirred at room temperature for 2 hours, acidified with dilute hydrochloric acid and extracted with ethyl acetate. The extracts were washed with water, dried ($Na_2SO_4$) and concentrated under reduced pressure. The residue was chromatographed on silica gel in hexane:ethyl acetate (5:1 to 3:2) to give an oil 732 mg (quantitative yield).

$^1$H NMR (CDCl$_3$) δ 1.13 (3H, t, J=6.9 Hz), 1.45 (3H, t, J=7.2 Hz), 2.47 (3H, s), 4.00 (2H, q, J=7.2 Hz), 4.45 (2H, q, J=7.5 Hz), 5.13 (2H, s), 6.46 (1H, d, J=7.5 Hz), 6.70 (1H, t, J=7.2 Hz), 7.3–7.5 (5H, m), 9.06 (1H, dd; J=6.9, 0.6 Hz).

Part E: Preparation of 8- and 6-Benzyloxy-2-methylthioindblizine 78

10% Aqueous potassium hydroxide (5 ml) was added to a solution of the diester (76, 337 mg, 0.815 m mol) in DMSO (5 ml). The mixture was heated under reflux for 8 hours. After cooling, the mixture was acidified with dilute hydrochloric acid with cooling in ice and extracted with ethyl acetate. The extracts were washed with water, dried ($Na_2SO_4$) and concentrated under reduced pressure to give a mixture of 77 and 78.

The solid in toluene (5 ml) was heated under reflux for 1 hour and concentrated under reduced pressure. The residue was chromatographed on silica gel (25 g) in hexane:ethyl acetate (5:1) and crystallized from hexane, 191 mg (87.0%). Mp, 94° C.

IR ν$_{max}$ (nujol) 1541, 750 cm$^{-1}$. $^1$H NMR (CDCl$_3$) δ 2.47 (3H, s), 5.17 (3H, s), 6.03 (1H, d, J=7.4 Hz), 6.34 (1H, t, J=7.2 Hz), 6.61 (1H, dd, J=1.8, 1.0 Hz), 7.22 (1H, d, J=1.6 Hz), 7.3–7.5 (6H, m). Analyses: Calc'd for $C_{16}H_{15}NOS.0.05C_6H_6$: C, 71.80; H, 5.43; N, 5.14 S, 11.76. Found: C, 71.83; H, 5.83; N, 5.08; S, 11.78.

Part F: Preparation of 2-(8- and 6-Benzyloxy-2-methylthio-3-(o-phenylbenzyl)indolizin-1-yl)glyoxylamide 80

80: A solution of 2-iodomethylbiphenyl (197 mg, 0.676 m mol) and the indolizine (78, 191 mg, 0.644 m mol) in benzene (2 ml) was allowed to stand at room temperature for 3 days. Aqueous sodium hydrogencarbonate was added. The mixture was extracted with ethyl acetate. The extracts were washed with water, dried ($Na_2SO_4$) and concentrated under reduced pressure. The residue was chromatographed on silica gel (25 g) in hexane:ethyl acetate to give a mixture of 8-benzyloxy-2-methylthio-3-(o-phenylbenzyloxy)indolizine, 79 and the starting material, 265 mg. A solution of the residue in tetrahydrofuran (3 ml) was added dropwise to a solution of oxalyl chloride (0.5 ml) in tetrahydrofuran (1 ml) with cooling in ice. The mixture was stirred for 30 min and added dropwise to concentrated ammonium hydroxide (10 ml) with cooling in ice. The mixture was stirred at room temperature for 1 hour. Ethyl acetate was added. The insoluble materials were removed by filtration. The organic phase was separated from the filtrate, washed with water, dried ($Na_2SO_4$) and concentrated under reduced pressure. The residue was chromatographed on silica gel (25 g) in hexane:ethyl acetate (1:1) and crystallized from benzene:hexane, 96 mg (28.5% from 78). Mp, 199–201° C.

IR ν$_{max}$ (nujol) 3419, 3160, 1703, 1640, 1498 cm$^{-1}$. $^1$H NMR (CDCl$_3$) δ 2.42 (3H, s), 4.40 (2H, s), 4.77 (1H, br.s), 5.10 (2H, s), 6.28 (1H, br.s), 6.33 (1H, d, J=7.8 Hz), 6.44 (1H, t, J=6.6 Hz), 6.79 (1H, d, J=7.8 Hz), 6.96 (1H, d, J=6.0 Hz), 7.15 (1H, dt, J=7.2, 1.8 Hz), 7.2–7.55 (12H, m). Analyses: Calc'd for $C_{31}H_{26}N_2O_3S$: C, 73.50; H, 5.17; N, 5.53 S, 6.33. Found: C, 73.65; H, 5.21; N, 5.45; S, 6.18.

Part G: Preparation of 2-(8-(Carbomethoxymethyloxy)-2-methylthio-3-(o-phenylbenzyl)indolizin-1-yl)glyoxylamide 82

81: 1N-Solution of borontribromide in dichloromethane (0.7 ml, 0.7 m mol) was added to a solution of the benzylether (80, 85 mg, 0.168 m mol) in dichloromethane (1 ml) with cooling in ice. The mixture was stirred at 0° C. for 1 hour. Ice-water was added. The mixture was extracted with dichloromethane:methanol. The extracts were washed with water, dried ($Na_2SO_4$) and concentrated under reduced pressure. The residue was recrystallized from ethyl acetate, mp, 138–142° C.

$^1$H NMR (CDCl$_3$+CD$_3$OD) δ 2.31 (3H, s), 4.41 (2H, s), 6.65–6.80 (3H, m), 7.01 (1H, dd, J=6.2, 1.2 Hz), 7.17 (1H, m), 7.3–7.6 (7H, m).

82: A mixture of the crystals 81, methyl bromoacetate (33 mg, 0.216 m mol), potassium carbonate (90 mg, 0.65 m mol) and a few piece of potassium iodide in DMF (1.2 ml) was stirred at room temperature for 18 hours. Water was added. The mixture was extracted with ethyl acetate. The extracts were washed with water, dried ($Na_2SO_4$) and concentrated under reduced pressure. The residue was chromatographed on silica gel (10 g) in ethyl acetate and crystallized from benzene:hexane, 35 mg (41.3%). Mp, 88–91° C.

$^1$H NMR (CDCl$_3$) δ 2.44 (3H, s), 3.77 (3H, s), 4.41 (2H, s), 4.70 (2H, s), 5.69 (1H, br.s), 6.20 (1H, d, J=7.8 Hz), 6.44 (1H, t, J=6.9 Hz), 6.79 (1H, br.s), 6.79 (1H, d, J=7.5 Hz), 6.99 (1H, d, J=7.5 Hz), 7.16 (1H, dt, J=7.5, 1.8 Hz), 7.1–7.55 (7H, m). Preparation of 81b: Mp, 271–273° C. (dec.). 86.5% Yield.

Preparation of 2-(8-(Carboxymethyloxy)-2-methylthio-3-(o-phenylbenzyl)indolizin-1yl)-glyoxylamide 83

83: Mp, 200–205° C. 65.4% Yield. IR ν$_{max}$ (nujol) 3392, 3220, 1745, 1620, 1305 cm$^{-1}$.

Preparation of 3-(N-Benzyloxycarbonyl)-2-methylpyridine 85

A mixture of 3-aminopicoline (84, 0.60 g, 5.5 m mol), (N-benzyloxycarbonyl)succinimide (2.1 g, 8.3 m mol) and DMF (2 ml) was left for 2 days. The reaction mixture was poured into water, extracted with ethyl acetate, washed with water and dried ($Na_2SO_4$). The solvent was removed in vacuo. The residue was chromatographed on silica gel eluting with ethyl acetate—hexane to give 85 (0.92 g, 68%), mp, 76–78° C. IR ν$_{max}$ (nujol) 1725, 1551, 1227, 1061 cm$^{-1}$. $^1$H NMR (CDCl$_3$) δ 2.49 (3H, s), 5.22 (3H, s), 7.16 (1H, m), J=8.7 Hz), 7.36–7.45 (5H, m), 8.15–8.27 (2H, m). Analyses: Calc'd for $C_{14}H_{14}N_2O_2$: C, 69.41; H, 5.82; N, 11.56. Found: C, 69.62; H, 5.89; N, 11.31.

Example 9

Part A: Preparation of 3-(N-Benzyloxycarbonyl-N-methoxycarbonylmethyl)amino-2-methylpyridine 86

To a suspension of sodium hydride (60%. dispersion in oil, 0.17 g, 4.2 m mol) in DMF (3 ml) was added 85 (0.92 g, 3.8 m mol) in DMF (5 ml) at 0° C. with stirring under a nitrogen atmosphere. Stirring was continued for 1 hour, at which time methyl bromoacetate (0.40 ml, 4.2 m mol) was added. The reaction mixture was stirred at room temperature for an additional 2.5 hours. The reaction mixture was poured into water, extracted with ethyl acetate, washed with water and dried ($Na_2SO_4$). The solvent was removed in vacuo. The product was purified by silica gel column chromatography eluting with ethyl acetate:hexane (1:1) to yield 86 (1.07 g, 90%) as a yellow oil, 1H NMR (CDCl$_3$) δ 2.43 (3/4H, s), 2.51 (1/4H, m), 3.68 (1/4H, m), 3.76 (3/4H, s), 3.85 (1H, d, J=18 Hz), 4.69 (1H, d, J=18 Hz), 5.06–5.21 (3/2H, m), 5.22 (1/2H, s), 7.13–7.37 (6H, m), 7.73 (1H, m), 8.45 (1H, m).

Part B: Preparation of 3-Benzyl-8-(N-benzyloxycarbonyl-N-methoxycarbonylmethyl)amino-2-methyl-indolizine 87a Compound 86 was converted to 87a by the same procedure cited for the preparation of 31 from 29 and 24. 42%

Yield. ¹H NMR (CDCl₃) δ 2.34 (3H, s), 3.67–3.77 (3H, m), 4.21–4.46 (4H, m), 5.15 (2/3H, s), 5.25 (1/3H, s), 6.28–6.37 (2H, m), 6.77 (1H, m), 7.04–7.50 (11H, m).

Preparation of 8-(N-Benzyloxycarbonyl-N-methoxycarbonylmethyl)amino-3-cyclohexylmethyl-2-methyl-indolizine 87b 31% Yield. ¹H NMR (CDCl₃) δ 0.82–1.80 (11H, m), 2.25 (3H, s), 2.70 (2H, d, J=7 Hz), 3.66 (3/4H, s), 3.74 (9/4H, s), 4.10–4.55 (2H, m), 5.15 (3/2H, s), 5.23 (1/2H, s), 6.19 (3/4H, s), 6.23 (1/4H, s), 6.43 (1H, m), 6.73 (3/4H, d, J=7 Hz), 6.79 (1/4H, d, J=7 Hz), 7.12–7.42 (5H, m), 7.64 (1H, d, J=7 Hz).

Part C: Preparation of 2-(3-Benzyl-8-(N-benzyloxycarbonyl-N-methoxycarbonylmethyl)amino-2-methyl-indolizin-1-yl)-glyoxylamide 88a Compound 87a was converted to 88a by the same procedure cited for the preparation of 34 from 28. 66% Yield. ¹H NMR (CDCl₃) δ 2.44 (1H, s), 2.45 (2H, s), 3.67 (1H, s), 3.73 (2H, s), 3.80 (1H, d, J=18 Hz), 4.24 (2H, s), 4.71 (1H, d, J=18 Hz), 5.00–5.31 (2H, m), 6.64 (1H, m), 7.04–7.42 (11H, m), 7.62 (1H, m).

Preparation of 2-(8-(N-benzyloxycarbonyl-N-methoxycarbonylmethyl)amino-3-cyclohexylmethyl-2-methyl-indolizin-1-yl)-glyoxylamide 88b 72% Yield. ¹H NMR (CDCl₃) δ 1.00–1.26 (4H, m), 1.50–1.78 (7H, m), 2.32 (1H, s), 2.33 (2H, s), 2.70 (2H, d, J=7 Hz), 3.67 (1H, s), 3.73 (2H, s), 3.78 (2/3H, d, J=18 Hz), 3.79 (1/3H, d, J=18 Hz), 4.60 (1/3H, d, J=18 Hz), 4.69 (2/3H, d, J=18 Hz), 5.03 (2/3H, d, J=13 Hz), 5.19 (1/3H, d, J=13 Hz), 5.23 (2/3H, d, J=13 Hz), 5.25 (1/3H, d, J=13 Hz), 6.73 (2/3H, t, J=7 Hz), 6.79 (1/3H, t, J=7 Hz), 7.14–7.43 (6H, m), 7.79 (1H, m).

Part D: Preparation of 2-(3-Benzyl-8-methoxycarbonylmethylamino-2-methyl-indolizin-1-yl)-glyoxylamide 89a A mixture of the indolizine (88a, 88 mg, 0.17 m mol) and 10% palladium-coal (0.02 g) in ethyl acetate (5 ml) was stirred in hydrogen atmosphere for 3 hours. The catalyst was filtered and the filtrate was concentrated under reduced pressure. Crystallization of the residue from tetrahydrofuran-ether afforded 89a (51 mg, 78%). Mp, 186–188° C. IR $v_{max}$ (nujol) 3410, 3149, 1750, 1689, 1566, 1221 cm⁻¹.

Preparation of 2-(8-methoxycarbonylmethylamino-3-cyclohexylmethyl-2-methyl-indolizin-1-yl)-glyoxylamide 89b Mp, 173–177° C. (methanol:ether:hexane). 90% Yield.

Part E: Preparation of 2-(3-Benzyl-8-carboxymethylamino-2-methyl-indolizin-1-yl)-glyoxylamide 90a Compound 89a was converted to 90a by the same procedure cited for the preparation of 52 from 51. Mp, 293° C. (dec.) (methanol:ether). 61% Yield.

IR $v_{max}$ (nujol) 1722, 1670, 1621, 1535, 1219 cm⁻¹. ¹H NMR (d⁶-DMSO) δ 2.56 (3H, s), 4.43 (2H, s), 4.87 (2H, s), 7.10–7.36 (7H, m), 8.23 (1H, d, J=7 Hz).

Preparation of 2-(8-Carboxymethylamino-3-cyclohexylmethyl-2-methyl-indolizin-1-yl)-glyoxylamide 90b Mp, >300° C. (methanol:ether). 47% Yield. IR $v_{max}$ (nujol) 3450, 1656, 1623, 1604, 1524 cm⁻¹. ¹H NMR (d₆-DMSO) δ 0.95–1.35 (5H, m), 1.51–1.80 (6H, m), 2.43 (3H, s), 2.85 (2H, d, J=7 Hz), 4.42 (2H, s), 7.00 (1H, d, J=7 Hz), 7.12 (1H, t, J=7 Hz), 8.32 (1H, d, J=7 Hz). IR $v_{max}$ (KBr) 1722, 1670, 1621, 1535, 1219 cm⁻¹.

Part F: Preparation of 2-(3-Benzyl-8-methoxycarbonylmethylamino-2-methyl-indolizin-1-yl)-acetamide 91

Compound 88a was converted to 91 by the same procedure cited for the preparation of 71a from 66c. Mp, 147–150° C. (dec.) (ethanol:ether:hexane). 55% Yield. IR $v_{max}$ (nujol) 3450, 3151, 1747, 1691, 1221 cm⁻¹.

Part G: Preparation of 2-(3-Benzyl-8-carboxymethylamino-2-methyl-indolizin-1-yl)-acetamide 92

Compound 91 was converted to 92 by the same procedure cited for the preparation of 52 from 51. 60% Yield. IR $v_{max}$ (nujol) 3431, 3303, 1714, 1670, 1545, 1141 cm⁻¹.

¹H NMR (d₆-DMSO) δ 2.31 (3H, s), 3.79–3.90 (2H, m), 4.19 (2H, s), 5.36 (1H, s), 5.49 (1H, d, J=7 Hz), 6.29 (1H, t, J=7 Hz), 7.00–7.27 (7H, m).

Part H: Preparation of 8-Benzyloxy-1-carboethoxy-2-methoxyindolizine 94

A mixture of (1) (1 g, 3.69 m mol) and methyl bromoacetate (10 ml) was stirred at 50° C. for 18 hours in nitrogen. Diethyl ether was added to the reaction mixture. The insoluble oil was washed with diethyl ether and dried at a reduced pressure. A mixture of the pyridinium salt and potassium carbonate (4.2g, 36.85 m mol) was stirred in 2-butanone (17 ml) at room temperature for 4 hours. Dimethyl sulfate (2.5 ml, 26.38 m mol) in 2-butanone (3 ml) was added, then the mixture was heated to 60° C. Water was added. The mixture was extracted with ethyl acetate. The extracts were dried (Na₂SO₄). After removing the solvent at a reduced pressure, the residue was chromatographed on silica gel in hexane/ethyl acetate=5/1. 382 mg (32% yield) of the title compound was obtained. IR $v_{max}$ (Neat) 2970, 1693, 1555, 1527, 1452, 1370, 1304 cm⁻¹. ¹H NMR (CDCl₃) d 1.11 (3H, t, J=7.0 Hz), 3.86 (3H, s), 4.12 (2H, q, J=7.0 Hz), 5.15 (2H, s), 6.30 (1H, d, J=7.8 Hz), 6.46 (1H, dd, J=6.6, J=7.8 Hz), 7.26–7.54 (5H, m).

Part I: Preparation of 2-(8-Benzyloxy-3-(biphenyl-2-yl)-2-methoxyindolizin-1-yl)glyoxylamide 95

A mixture of 94 (915 mg, 2.81 m mol) and 50% aqueous sodium hydroxide (5 ml) in dimethyl sulfoxide (40 ml) was heated to 140° C. for 4 hours. After cooling at 0° C., the mixture was acidified carefully with 1N hydrochloric acid and extracted with ethyl acetate. The extracts were dried (Na₂SO₄). After removing the solvent at reduced pressure, the carboxylic acid was obtained. The mixture of the carboxylic acid in toluene (3 ml) was stirred at 80° C. for 2.5 hours. After cooling, o-iodomethyl biphenyl (909 mg, 3.09 m mol) in toluene (4 ml) was added at room temperature in nitrogen, and the mixture was stirred for 4 days. Water was added. The mixture was extracted with ethyl acetate. The extracts were dried (Na₂SO₄). After removing the solvent at a reduced pressure, the residue was chromatographed on silica gel in hexane/ethyl acetate=20/1. The purified oil in tetrahydrofuran (4 ml) was added dropwise to oxallyl chrolide (3 ml) in tetrahydrofuran (6 ml) at 0° C. in nitrogen, then warmed to room temperature and stirred for 2 hours. The reaction mixture was added to 28% aqueous ammonium hydoxide (40 ml) at 0° C. After diluting with water, the mixture was extracted with ethyl acetate. The extracts were dried (Na₂SO₄). After removing the solvent at a reduced pressure, the residue was chromatographed on silica gel in toluene/ethyl acetate. 316 mg (23% yield, 5 steps) of the title compound was obtained, Mp, 183–184° C. (hexane/ethyl acetate). IR $n_{max}$ (KBr) 3395, 1692, 1605, 1535, 1494, 1304, 1017 cm⁻¹. ¹H NMR (CDCl₃) d 3.89 (3H, s), 4.14 (2H, s), 5.10 (3H, m), 6.23 (1H, br, s), 6.35–6.48 (2H, m), 6.91–6.98 (2H, m), 7.12–7.52 (13H, m). Analysis: Calc'd for $C_{31}H_{26}N_2O_4$ 0.2H₂O: C, 75.35; H, 5.38; N, 5.67. Found: C, 75.31; H, 5.48; N, 5.82.

Part J: Preparation of 2-(3-(Biphenyl-2-yl)-8-(carbomethoxymethyloxy)-2-methoxyindolizin-1-yl) glyoxylamide 96

A mixture of 95 (290 mg, 0.59 m mol) and 10% palladium-coal (210 mg) in methanol (10 ml) and tetrahydrofuran (10 ml) was stirred in hydrogen for 10 hours. The catalyst was filtered and washed with methanol. The filtrate was concentrated under a reduced pressure. A mixture of the compound, methyl bromoacetate (0.28 ml, 2.96 m mol), potassium carbonate (247 mg, 1.77 m mol) and potassium iodode (110.8 mg, 0.66 m mol) in DMF (4 ml) was stirred at room temparature for 16 hours. The reaction mixture was quenched at 0° C. with 1N hydrochrolic acid. The mixture was extracted with ethyl acetate. The extracts were dried ($Na_2SO_4$). After removing the solvent at a reduced pressure, the residue was chromatographed on silica gel in toluene/ethyl acetate=1:1. 156 mg (56% yield, 2 steps) of the title compound was obtained, Mp, 188–189° C. (hexane/ethyl acetate). IR $n_{max}$ (KBr) 3395, 3175, 1761, 1685, 1589, 1490, 1310, 1208 $cm^{-1}$. $^1$H NMR ($CDCl_3$) d 3.78 (3H, s), 3.93 3H, s), 4.15 (2H, s), 4.70 (2H, s), 5.56 (1H, br s), 6.27 (1H, d, J=7.8 Hz), 6.47 (1H, dd, J=6.6Hz, 7.8Hz), 6.63 (1H, br s), 6.97 (2H, d, J=6.6Hz), 7.14–7.49 (8H, m). Analysis: Calc'd for $C_{27}H_{24}N_2O_6$ $0.2H_2O$: C, 68.12; H, 5.17; N, 5.88. Found: C, 68.23; H, 5.26; N, 5.97.

Part K: Preparation of 2-(3-(Biphenyl-2-yl)-8-(carboxymethyloxy)-2-methoxyindolizin-1-yl) glyoxylamide 97

A mixture of 96 (86.6 mg, 0.183 m mol) and 30% aqueous sodium hydroxide (2 ml) in methanol (40 ml) and tetrahydrofuran (10 ml) was stirred at room temparature for 17 hours. The reaction mixture was quenched with 1N hydrochloric acid. The mixture was extracted with ethyl acetate. The extracts were dried ($Na_2SO_4$). After removing the soluvent at a reduced presure, the residue was recrystallized from ethyl acetate. 26.5 mg (32% yield) of the title compound was obtained. Mp, 197–198° C. (ethyl acetate). IR $n_{max}$ (KBr) 3461, 3351, 1731, 1639, 1618, 1496, 1238, $cm^{-1}$. $^1$H NMR (DMSO) d 3.74 (3H, s), 4.15 (2H, s), 4.71 (2H, s), 6.49 (1H, d, J=7.6 Hz), 6.67–6.77 (2H, m), 7.23–7.72 (11H, m). Analysis: Calc'd for $C_{26}H_{22}N_2O_6$: C, 68.12; H, 4.84; N, 6.11. Found: C, 67.89; H, 4.96; N, 6.12.

Therapeutic Use of Indolizine Compounds

The indolizine-1-functional and indolizine-3-functional compounds of the invention are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA2 mediated release of fatty acids comprises contacting a mammal, including a human, suffering from or susceptible to a disease in which sPLA2 mediated release of fatty acids is a cause with a therapeutically effective amount of compound corresponding to formulae (IA), (IIA), (IIIA), (IB), (IIB), or (IIIB) or a salt or a prodrug derivative thereof.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administrating to a mammal at least one compound represented by formulae (IA), (IIA), (IIIA), (IB), (IIB), or (IIIB) or any combination thereof in a therapeutically effective amount. A therapeutically effective amount is an amount sufficient to inhibit $sPLA_2$ mediated release of fatty acid and to thereby inhibit or prevent the arachidonic acid cascade and its deleterious products. The therapeutic amount of compound of the invention needed to inhibit $sPLA_2$ may be readily determined by taking a sample of body fluid and assaying it for $sPLA_2$ content by conventional methods.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the indolizine-1-functional and indolizine-3-functional compounds of the invention (represented by formulae (IA), (IIA), (IIIA), (IB), (IIB), or (IIIB)) together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound.

The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include susrsensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to formulae (IA), (IIA), (IIIA), (IB), (IIB), or (IIIB) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The Components are Blended and Compressed to Form Tablets Each Weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, ae made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

Assay Experiments

Assay 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:
REACTION BUFFER—

| $CaCl_2.2H_2O$ | (1.47 g/L) |
|---|---|
| KCl | (7.455 g/L) |

Bovine Serum Albumin (fatty acid free) (1 g/L) (Sigma A-7030, product of Sigma Chemical Co. St. Louis Mo., USA)

TRIS HCl (3.94 g/L)

pH 7.5 (adjust with NaOH)

ENZYME BUFFER—

0.05 NaOAc.3H2O, pH 4.5

0.2 NaCl

Adjust pH to 4.5 with acetic acid

DTNB—5,5'-dithiobis-2-nitrobenzoic acid

RACEMIC DIHEPTANOYL THIO—PC racemic 1,2-bis(heptanoylthio)-1,2-dideoxy-sn-glycero-3-phosphorylcholine TRITON X-100™ prepare at 6.249 mg/ml in reaction buffer to equal 10 uM.

REACTION MIXTURE—

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoyl thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to, 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

The results of Human Secreted Phospholipase $A_2$ Inhibition tests are displayed in the Table below:

TABLE sPLA$_2$ Chromogenic Assay Data

| Compd. | $IC_{50}$ ($\mu$M) |
|---|---|
| 11 | 1.1 |
| 20x | 0.84 |
| 21x | 0.14 |
| 21y | 0.35 |
| 22x | 0.014 |
| 22y | 0.015 |
| 34 | 0.89 |
| 35a | 0.4 |
| 35g | 0.047 |
| 37a | 0.044 |
| 37d | 0.013 |
| 37g | 0.023 |
| 38a | 0.052 |
| 39d | 0.017 |
| 40a | 0.008 |
| 40b | >50* |
| 40c | >50* |
| 40d | 0.006 |
| 40f | >50* |
| 40g | 0.008 |
| 49k | 0.79 |
| 49s | 0.36 |
| 51a | 0.81 |
| 51b | 0.31 |
| 51c | 0.43 |
| 51d | 0.55 |
| 51f | 0.59 |
| 51g | 0.17 |
| 51j | 0.02 |
| 51k | 0.22 |
| 51l | 0.096 |
| 51m | 0.31 |
| 51s | 0.15 |
| 51t | 0.13 |
| 52a | 0.018 |
| 52b | 0.021 |
| 52c | 0.019 |
| 52d | 0.023 |
| 52e | 0.062 |
| 52f | 0.017 |
| 52g | 0.017 |
| 52i | 0.051 |
| 52j | 0.006 |
| 52k | 0.011 |
| 52l | 0.010 |
| 52m | 0.021 |
| 52n | 0.036 |
| 52o | 0.025 |
| 52r | 0.046 |
| 52s | 0.011 |
| 52t | 0.01 |
| 52v | 0.029 |
| 52w | 0.014 |
| 57a | 0.033 |
| 57g | 0.08 |
| 57j | 0.79 |
| 58a | 0.008 |
| 58c | 0.035 |
| 58e | 0.1 |
| 58f | 0.28 |
| 58g | 0.009 |
| 58h | 0.038 |
| 58i | 0.051 |
| 58j | 0.023 |
| 58k | 0.043 |
| 59a | 0.007 |
| 59b | 0.011 |
| 59c | 0.046 |
| 59d | 0.083 |
| 59e | 0.055 |
| 59f | 0.07 |
| 59g | 0.039 |
| 59h | 0.061 |
| 59i | 0.022 |
| 59j | 0.053 |
| 59k | 0.113 |
| 59l | 0.11 |
| 59m | 0.007 |
| 59n | 0.6 |
| 59o | 0.49 |
| 59p | 0.2 |
| 67a | 0.2 |
| 67c | 0.14 |
| 69a | 0.08 |
| 70a | 0.044 |
| 70b | 0.24 |
| 70c | 0.13 |
| 71a | 0.6 |
| 82 | 0.12 |
| 83 | 0.016 |
| 97 | 0.015 |

*= comparative example

Effect of Indolizines on PLA2 induced Pancreatitis in Rats

Experimental Protocol:

Male Wistar rats weighing 220–270g were fasted overnight. Under pentobarbital anesthesia (40 mg/kg intraperitoneally), laparotomy was made and pancreatitis was induced by the retrograde infusion of a mixture of porcine pancreas PLA2 (300U/rat) and sodium taurocholate (10 mg/rat) into the common bile duct in a volume of 0.2 ml. The survival rate at 12 hours after the induction of pancreatitis was checked.

Compound 39d was suspended in a 0.6% gum arabic solution used as vehicle. Eleven to twelve animals were used in each test group.

Results:

Compound 39d (1, 3, 10 mg/kg) significantly improved the animal survival rate at 12 hour. Rat survival (%) for (vehicle), (1), (3), and (10) mg/kg of compound 39d group were 33.3, 81.8*, 91.7, and 91.7, respectively (*$P<0.05$, **$P<0.01$, Chi-square test).

(39d)

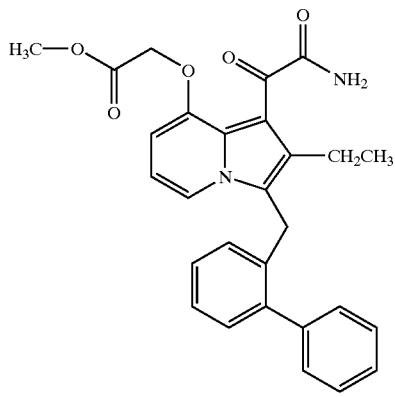

While the present invention has been illustrated above by certain specific embodiments, it is not intended that these specific examples should limit the scope of the invention as described in the appended claims.

We claim:

1. An indolizine-1-acetamide compound or a pharmaceutically acceptable salt or an ester or amide prodrug derivative thereof; wherein said compound is represented by the formula (IA);

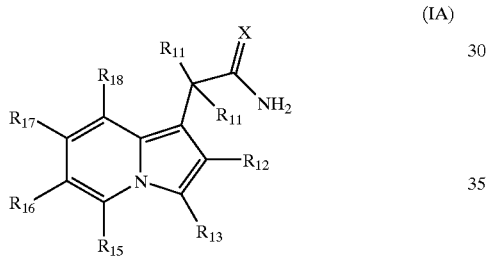

(IA)

wherein;

X is oxygen or sulfur;

each $R_{11}$ is independently hydrogen, $C_1$–$C_3$ alkyl, or halo;

$R_{13}$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_{17}$ and $R_{18}$ are independently selected from hydrogen, a non-interfering substituent, or the group, —($L_a$)—(acidic group); wherein —($L_a$)—, is an acid linker having an acid linker length of 1 to 10; provided, that at least one of $R_{17}$ and $R_{18}$ must be the group, —($L_a$)—(acidic group);

$R_{15}$ and $R_{16}$ are each independently selected from hydrogen, non-interfering substituent, carbocyclic radical, carbocyclic radical substituted with non-interfering substituents, heterocyclic radical, and heterocyclic radical substituted with non-interfering substituents;

provided that the non-interfering substituent for $R_{13}$, $R_{12}$, $R_{17}$, $R_{18}$, $R_{15}$, or $R_{16}$ is selected from $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, or $C_1$–$C_6$ carbonyl; where n is from 1 to 8.

2. The compound of claim 1 wherein;

(i) X is oxygen;

(ii) $R_{12}$ is selected from the group; halo, cyclopropyl, methyl, ethyl, and propyl;

(iii) $R_{13}$ has as a linking group —(L)— an alkylene chain of 1 or 2 carbon atoms and $R_{80}$ is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

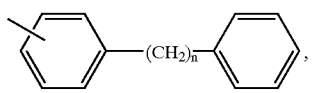

(bb)

where n is a number from 1 to 8;

(iv) $R_{17}$ or $R_{18}$ have an (acidic group) on the group —($L_a$)—(acidic group) selected from:

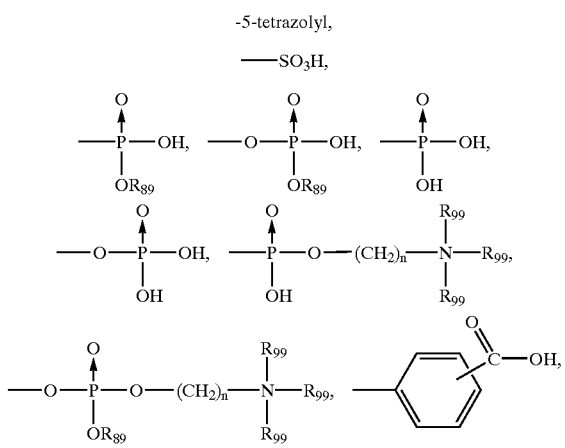

-continued

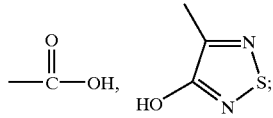

where n is 1 to 8, $R_{89}$ is a metal or $C_1$–$C_{10}$ alkyl, and $R_{99}$ is hydrogen or $C_1$–$C_{10}$ alkyl; and (v) $R_{15}$ and $R_{16}$ are each independently selected from hydrogen and non-interfering substituents, with the non-interfering substituents being selected from the group consisting of the following: $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

3. The compound of claim 2, wherein, (A) for (iii), the group $R_{13}$ is selected from the group consisting of

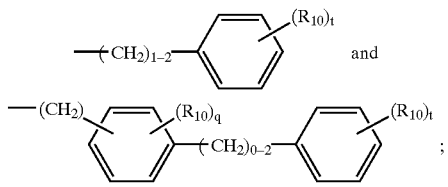

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5; and (B) for (iii) the linking group —(L)— of $R_{13}$ is selected from the group consisting of:

—C≡C—, —CH=CH—, —CH$_2$—,

—(CH$_2$)$_2$—, —(CH$_2$)$_s$—S—, —(CH$_2$)$_s$—O—, and

, where s = 0 or 1;

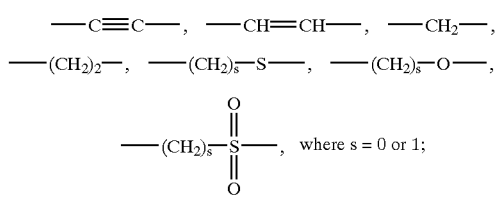

(C) for (iv) the (acidic group) of $R_{17}$ or $R_{18}$ is selected from:

—CO$_2$H, —SO$_3$H, —P(O)(OH)$_2$.

4. An indolizine-1-acetic acid hydrazide compound or a pharmaceutically acceptable salt or an ester or amide prodrug derivative thereof where said compound is represented by the formula (IIA);

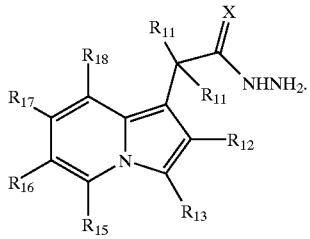

(IIA)

wherein:

X is oxygen or sulfur;

each $R_{11}$ is independently hydrogen, $C_1$–$C_3$ alkyl, or halo;

$R_{13}$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_{17}$ and $R_{18}$ are independently selected from hydrogen, a non-interfering substituent, or the group, —(L$_a$)— (acidic group); wherein —(L$_a$)—, is an acid linker having an acid linker length of 1 to 10; provided, that at least one of $R_{17}$ and $R_{18}$ must be the group, —(L$_a$)— (acidic group);

$R_{15}$ and $R_{16}$ are each independently selected from hydrogen, non-interfering substituent, carbocyclic radical, carbocyclic radical substituted with non-interfering substituents, heterocyclic radical, and heterocyclic radical substituted with non-interfering substituents; and provided that the non-interfering substituent for $R_{13}$, $R_{12}$, $R_{17}$, $R_{18}$, $R_{15}$, or $R_{16}$ is selected from $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkyithio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, or $C_1$–$C_6$ carbonyl; where n is from 1 to 8.

5. An indolizine-1-glyoxylamide compound or a pharmaceutically acceptable salt or an ester or amide prodrug derivative thereof; wherein said compound is represented by the formula (IIIA);

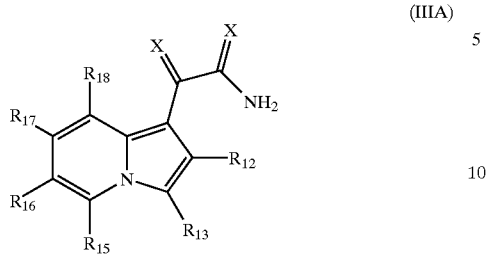

(IIIA)

X is oxygen or sulfur;
$R_{13}$ is selected from groups (a), (b) and (c) where;
  (a) is $C_7$–$C_{20}$ alkyl, $C_7$–$C_{20}$ alkenyl, $C_7$–$C_{20}$ alkynyl, carbocyclic radical, or heterocyclic radical, or
  (b) is a member of (a) substituted with one or more independently selected non-interfering substituents; or
  (c) is the group —(L)—$R_{80}$; where, —(L)— is a divalent linking group of 1 to 12 atoms and where $R_{80}$ is a group selected from (a) or (b);
$R_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;
$R_{17}$ and $R_{18}$ are independently selected from hydrogen, a non-interfering substituent, or the group, —($L_a$)—(acidic group); wherein —($L_a$)—, is an acid linker having an acid linker length of 1 to 10; provided, that at least one of $R_{17}$ and $R_{18}$ must be the group, —($L_a$)—(acidic group);
$R_{15}$ and $R_{16}$ are each independently selected from hydrogen, non-interfering substituent, carbocyclic radical, carbocyclic radical substituted with non-interfering substituents, heterocyclic radical, and heterocyclic radical substituted with non-interfering substituents; and
provided that the non-interfering substituent for $R_{13}$, $R_{12}$, $R_{17}$, $R_{18}$, $R_{15}$, or $R_{16}$ is selected from $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, or $C_1$–$C_6$ carbonyl; where n is from 1 to 8.

6. The compound of claim 5 wherein;
(i) X is oxygen;
(ii) $R_{12}$ is selected from the group; halo, cyclopropyl, methyl, ethyl, and propyl;
(iii) $R_{13}$ has as a linking group —(L)— an alkylene chain of 1 or 2 carbon atoms and $R_{80}$ is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

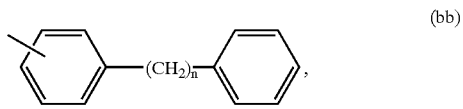

(bb)

where n is a number from 1 to 8;
(iv) $R_{17}$ or $R_{18}$ have an (acidic group) on the group —($L_a$)—(acidic group) selected from:

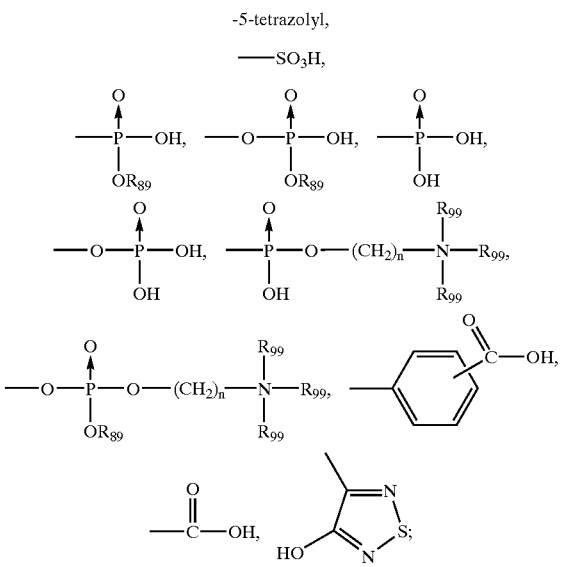

where n is 1 to 8, $R_{89}$ is a metal or $C_1$–$C_{10}$ alkyl, and $R_{99}$ is hydrogen or $C_1$–$C_{10}$ alkyl; and
(v) $R_{15}$ and $R_{16}$ are each independently selected from hydrogen and non-interfering substituents, with the non-interfering substituents being selected from the group consisting of the following: $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

7. The compound of claim 6, wherein, (A) for (iii), the group $R_{13}$ is selected from the group consisting of

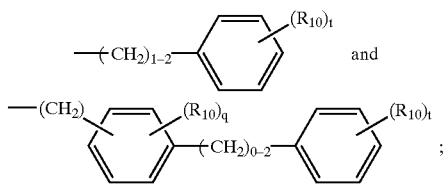

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5; and (B) for (iii) the linking group —(L)— of $R_{13}$ is selected from the group consisting of:

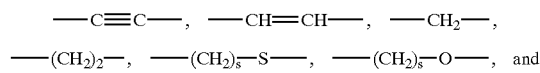

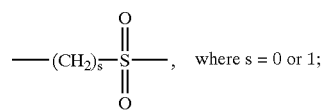, where s = 0 or 1;

(C) for (iv) the (acidic group) of $R_{17}$ or $R_{18}$ is selected from:

8. The compound of claim 5 wherein $R_{18}$ comprises an acidic group and has an acid linker with an acid linker length of 2 or 3 and the acid linker group, —($L_a$)—, for $R_{18}$ is represented by the formula;

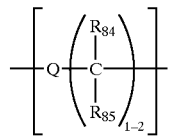

where Q is selected from the group —($CH_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

9. The compound of claim 8 wherein $R_{18}$ comprises an acidic group and the acid linker group, —($L_a$)—, for $R_{18}$ is selected from the group consisting of;

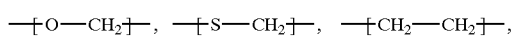

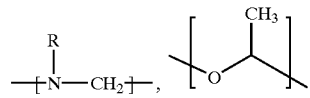

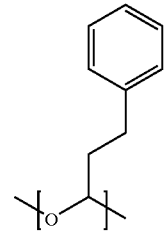

where R is H or $C_1$–$C_4$ alkyl.

10. The compound of claim 5 wherein $R_{17}$ comprises an acidic group and has an acid linker with an acid linker length of 3 to 10 atoms and the acid linker group, —($L_a$)—, for $R_{17}$ is selected from;

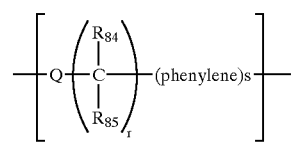

where r is a number from 1 to 7, s is 0 or 1, and Q is selected from the group —($CH_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

11. The compound of claim 10 wherein the acid linker, —($L_a$)—, for $R_{17}$ is selected from group consisting of;

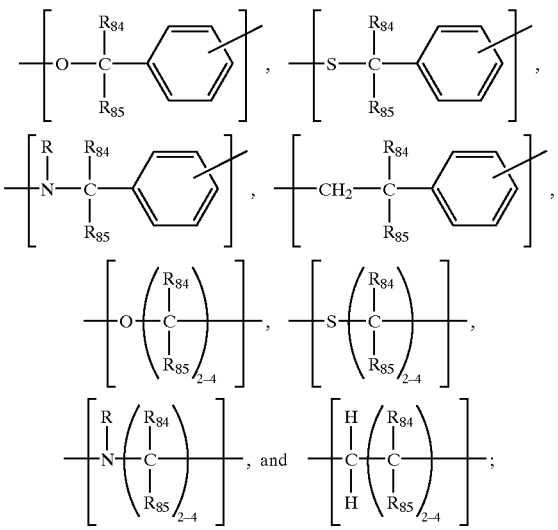

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

12. An indolizine-3-acetamide compound or a pharmaceutically acceptable salt or an ester or amide prodrug derivative thereof; wherein said compound is represented by the formula (IB), as set out below:

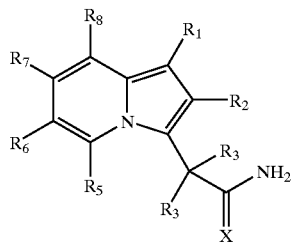

(IB)

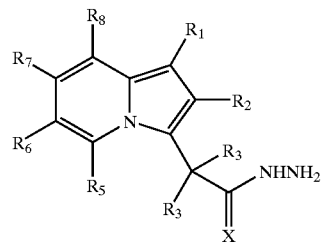

(IIB)

wherein;
  X is selected from oxygen or sulfur;
  each $R_3$ is independently hydrogen, $C_1$–$C_3$ alkyl, or halo;
  $R_1$ is selected from groups (a), (b) and (c) where;
    (a) is $C_7$–$C_{20}$ alkyl, $C_7$–$C_{20}$ alkenyl, $C_7$–$C_{20}$ alkynyl, carbocyclic radical, or heterocyclic radical, or
    (b) is a member of (a) substituted with one or more independently selected non-interfering substituents; or
    (c) is the group —(L)—$R_{80}$; where, —(L)— is a divalent linking group of 1 to 12 atoms and where $R_{80}$ is a group selected from (a) or (b);
  $R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;
  $R_5$ and $R_6$ are independently selected from hydrogen, a non-interfering substituent, or the group, —($L_a$)— (acidic group); wherein —($L_a$)—, is an acid linker having an acid linker length of 1 to 10; provided, that at least one of $R_5$ and $R_6$ must be the group, —($L_a$)— (acidic group);
  $R_7$ and $R_8$ are each independently selected from hydrogen, non-interfering substituent, carbocyclic radical, carbocyclic radical substituted with non-interfering substituents, heterocyclic radical, and heterocyclic radical substituted with non-interfering substituents; and
  provided that the non-interfering substituent for $R_3$, $R_2$, $R_5$, $R_6$, $R_7$, or $R_8$ is selected from $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, or $C_1$–$C_6$ carbonyl; where n is from 1 to 8.

13. A indolizine-3-hydrazide compound or a pharmaceutically acceptable salt or an ester or amide prodrug derivative thereof; wherein said compound is represented by the formula (IIB), as set out below:

wherein;
  X is selected from oxygen or sulfur;
  each $R_3$ is independently hydrogen, $C_1$–$C_3$ alkyl, or halo;
  $R_1$ is selected from groups (a), (b) and (c) where;
    (a) is $C_7$–$C_{20}$ alkyl, $C_7$–$C_{20}$ alkenyl, $C_7$–$C_{20}$ alkynyl, carbocyclic radical, or heterocyclic radical, or
    (b) is a member of (a) substituted with one or more independently selected non-interfering substituents; or
    (c) is the group —(L)—$R_{80}$; where, —(L)— is a divalent linking group of 1 to 12 atoms and where $R_{80}$ is a group selected from (a) or (b);
  $R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;
  $R_5$ and $R_6$ are independently selected from hydrogen, a non-interfering substituent, or the group, —($L_a$)— (acidic group); wherein —($L_a$)—, is an acid linker having an acid linker length of 1 to 10; provided, that at least one of $R_5$ and $R_6$ must be the group, —($L_a$)— (acidic group);
  $R_7$ and $R_8$ are each independently selected from hydrogen, non-interfering substituent, carbocyclic radical, carbocyclic radical substituted with non-interfering substituents, heterocyclic radical, and heterocyclic radical substituted with non-interfering substituents; and
  provided that the non-interfering substituent for $R_3$, $R_2$, $R_5$, $R_6$, $R_7$, or $R_8$ is selected from $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSC$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, or $C_1$–$C_6$ carbonyl; where n is from 1 to 8.

14. A indolizine-3-glyoxylamide compound or a pharmaceutically acceptable salt or an ester or amide prodrug derivative thereof; wherein said compound is represented by the formula (IIIB), as set out below:

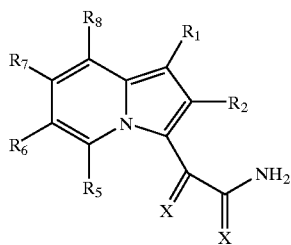

(IIIB)

wherein;
  each X is independently selected from oxygen or sulfur;
  each $R_3$ is independently hydrogen, $C_1$–$C_3$ alkyl, or halo;
  $R_1$ is selected from groups (a), (b) and (c) where;
    (a) is $C_7$–$C_{20}$ alkyl, $C_7$–$C_{20}$ alkenyl, $C_7$–$C_{20}$ alkynyl, carbocyclic radical, or heterocyclic radical, or
    (b) is a member of (a) substituted with one or more independently selected non-interfering substituents; or
    (c) is the group —(L)—$R_{80}$; where, —(L)— is a divalent linking group of 1 to 12 atoms and where $R_{80}$ is a group selected from (a) or (b);
  $R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;
  $R_5$ and $R_6$ are independently selected from hydrogen, a non-interfering substituent, or the group, —($L_a$)—(acidic group); wherein —($L_a$)—, is an acid linker having an acid linker length of 1 to 10; provided, that at least one of $R_5$ and $R_6$ must be the group, —($L_a$)—(acidic group);
  $R_7$ and $R_8$ are each independently selected from hydrogen, non-interfering substituent, carbocyclic radical, carbocyclic radical substituted with non-interfering substituents, heterocyclic radical, and heterocyclic radical substituted with non-interfering substituents; and
  provided that the non-interfering substituent for $R_3$, $R_2$, $R_5$, $R_6$, $R_7$, or $R_8$ is selected from $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, or $C_1$–$C_6$ carbonyl; where n is from 1 to 8.

15. The compound of claim 14 wherein;
  (i) X is oxygen;
  (ii) $R_2$ is selected from the group; halo, cyclopropyl, methyl, ethyl, and propyl;
  (iii) $R_1$ has as a linking group —(L)— an alkylene chain of 1 or 2 carbon atoms and $R_{80}$ is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

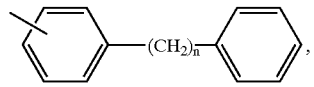

(bb)

where n is a number from 1 to 8;
  (iv) $R_5$ or $R_6$ have an (acidic group) on the group —($L_a$)—(acidic group) selected from:

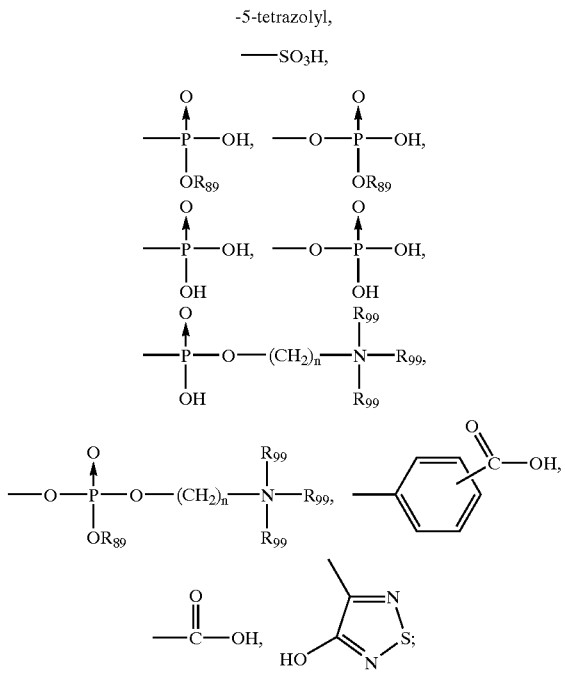

where n is 1 to 8, $R_{89}$ is a metal or $C_1$–$C_{10}$ alkyl, and $R_{99}$ is hydrogen or $C_1$–$C_{10}$ alkyl; and
  (v) $R_7$ and $R_8$ are each independently selected from hydrogen and non-interfering substituents, with the non-interfering substituents being selected from the group consisting of the following: $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —SO₃H, thioacetal, thiocarbonyl, and $C_1$–$C_6$ carbonyl; where n is from 1 to 8.

16. The compound of claim 15, wherein, (A) for (iii), the group $R_1$ is selected from the group consisting of

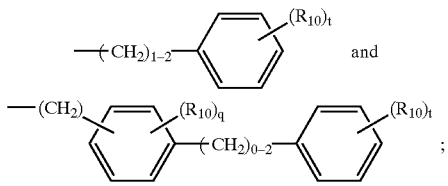

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5; and where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, and t is a number independently selected from 0 to 5; and (B) for (iii) the linking group —(L)— of $R_1$ is selected from the group consisting of:

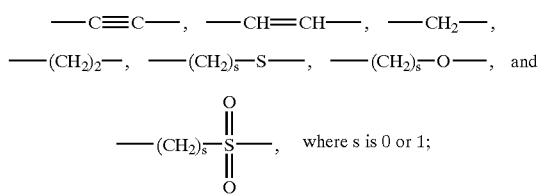

, where s is 0 or 1;

(C) for (iv) the (acidic group) of $R_5$ or $R_6$ is selected from:

—CO₂H, —SO₃H, —P(O)(OH)₂.

17. The compound of claim 14 wherein $R_5$ comprises an acidic group and has an acid linker with an acid linker length of 2 or 3 and the acid linker group, —($L_a$)—, for $R_5$ is represented by the formula;

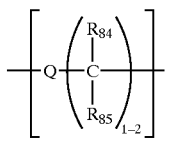

where Q is selected from the group —(CH₂)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

18. The compound of claim 17 wherein $R_5$ comprises an acidic group and the acid linker group, —($L_a$)—, for $R_5$ is selected from the group consisting of;

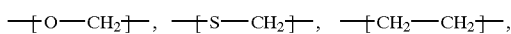

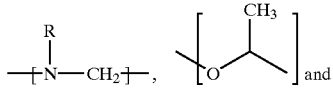

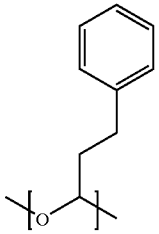

where R is H or $C_1$–$C_4$ alkyl.

19. The compound of claim 14 wherein $R_6$ comprises an acidic group and has an acid linker with an acid linker length of 3 to 10 atoms and the acid linker group, —($L_a$)—, for $R_6$ is selected from;

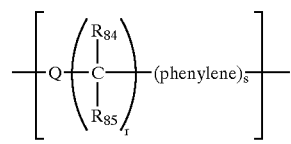

where r is a number from 1 to 7, C is 0 or 1, and Q is selected from the group —(CH₂)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

20. The compound of claim 19 wherein the acid linker, —($L_a$)—, for $R_6$ is selected from group consisting of;

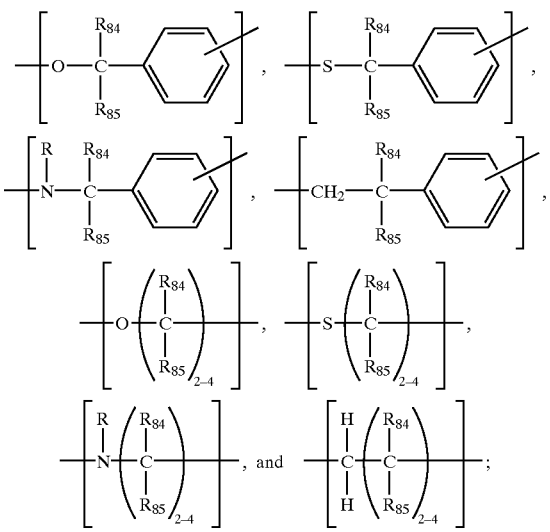

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

21. An indolizine-1-acetamide functional compound or a pharmaceutically acceptable salt, solvate or prodrug derivative thereof; wherein said compound is selected from the group represented by the following formulae:

(22v)
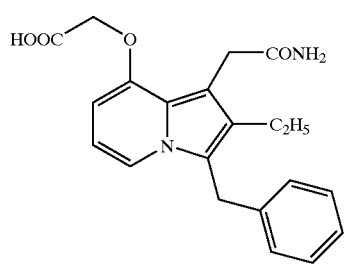
(22w)
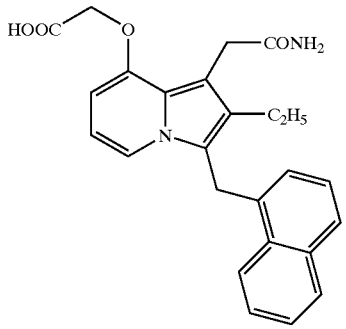
(22x)
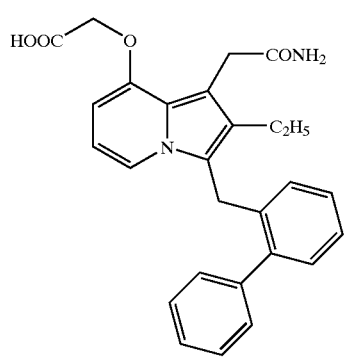
(22y)
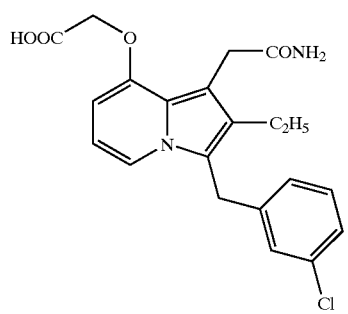
(22z)
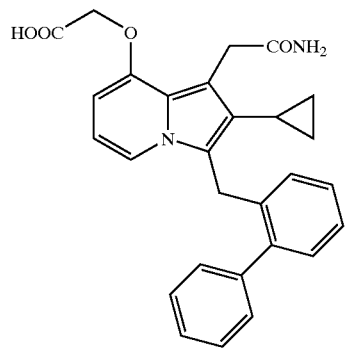
(92)
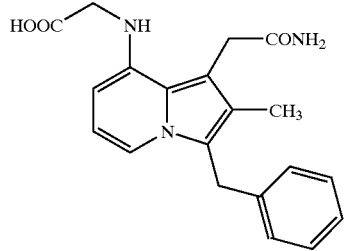
(71b)
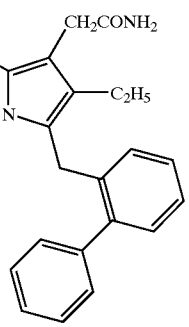
and mixtures of the above compounds.
22. An indolizine-1-glyoxylamide functional compound and a pharmaceutically acceptable salt, solvate or prodrug derivative thereof; wherein said compound is selected from the group represented by the following formulae:
(40a)
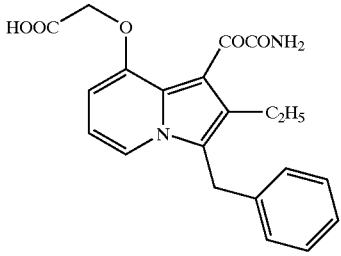
(40d)
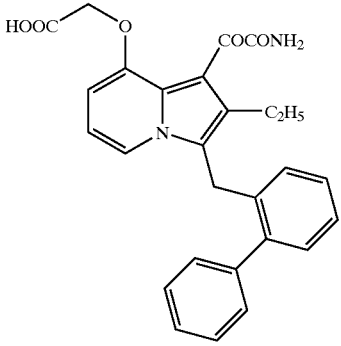

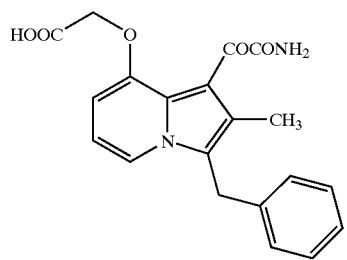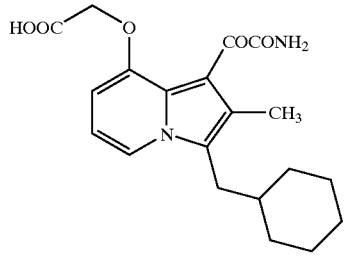

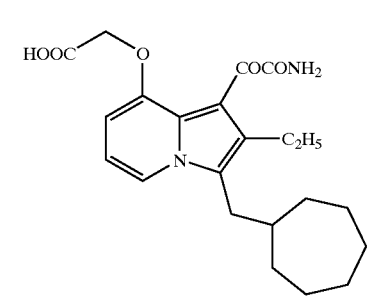
(52d)
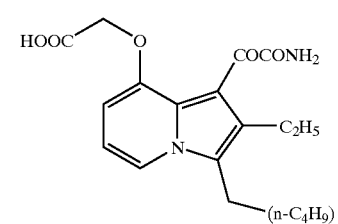
(52e)
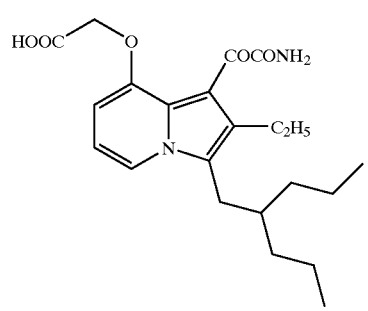
(52f)
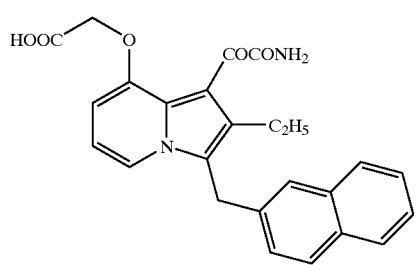
(52g)
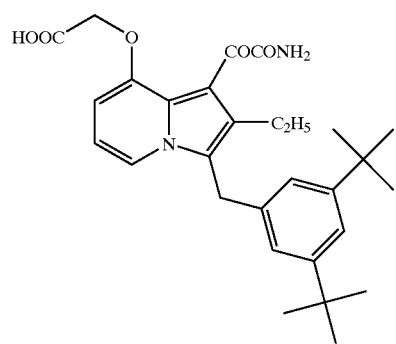
(52h)
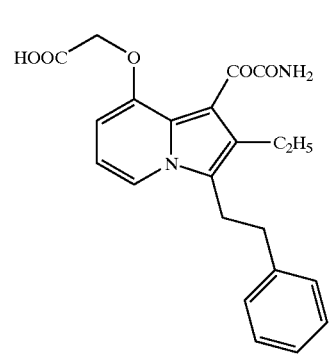
(52i)
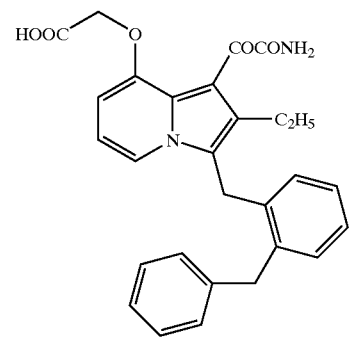
(52j)
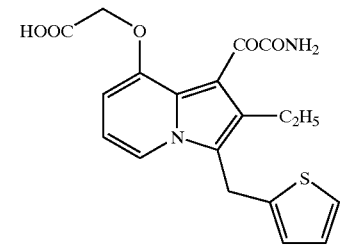
(52k)
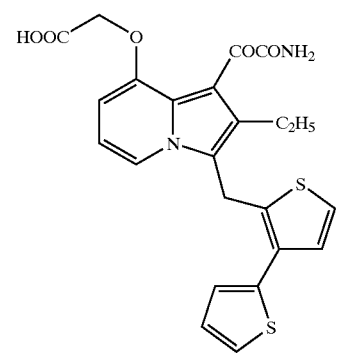
(52l)
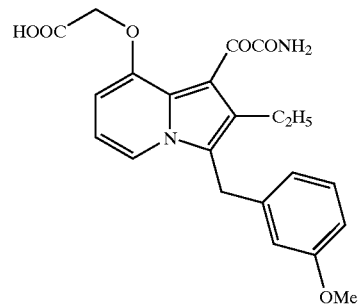
(52m)

(52n) 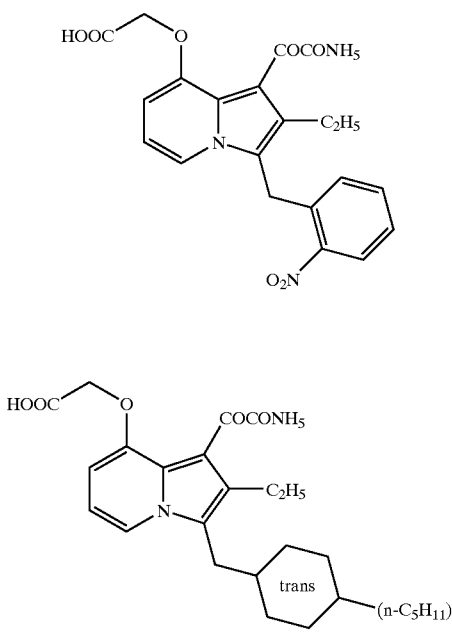
(52o) 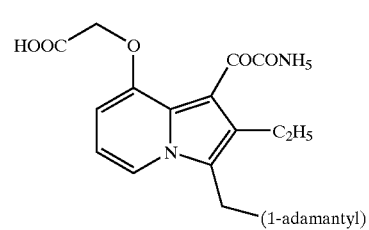
(52p) 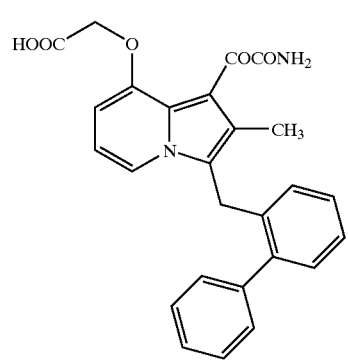
(52q) 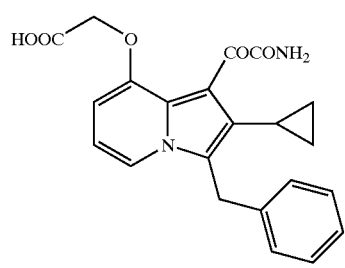
(52r) 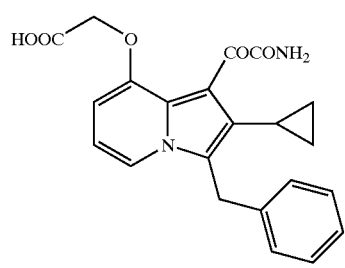
(52s) 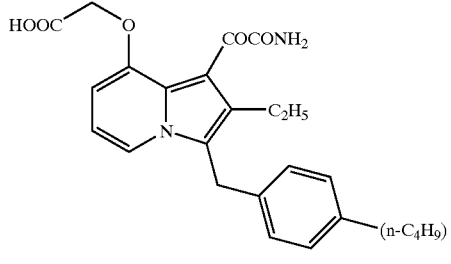
(52t) 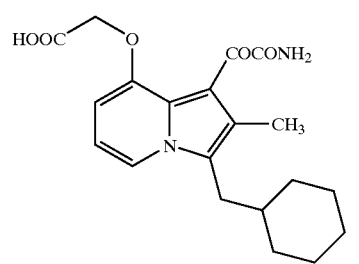
(52u) 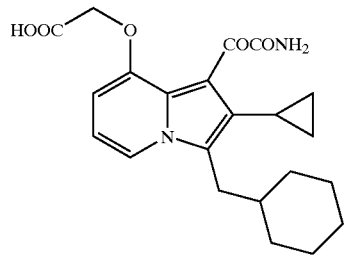
(52v) 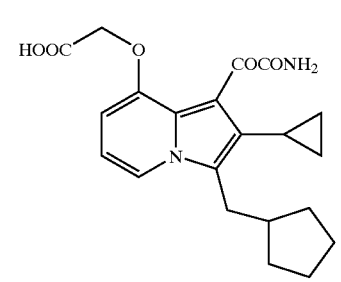
(52w) 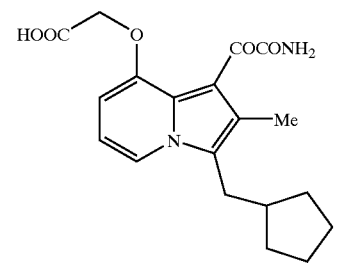

(58a)
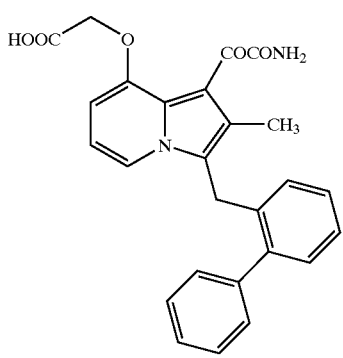
(58g)
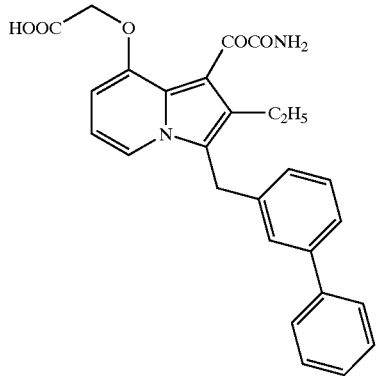
(58c)
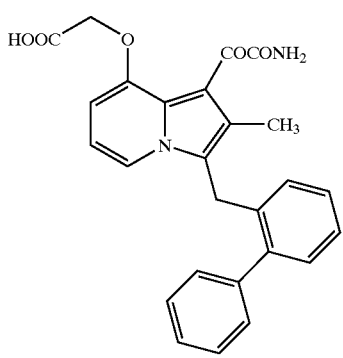
(58h)
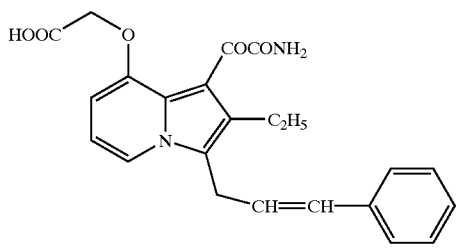
(58i)
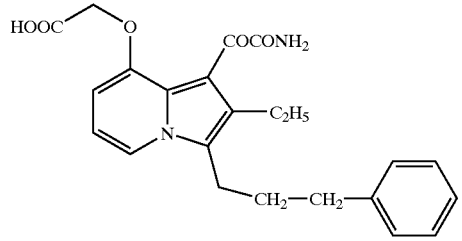
(58e)
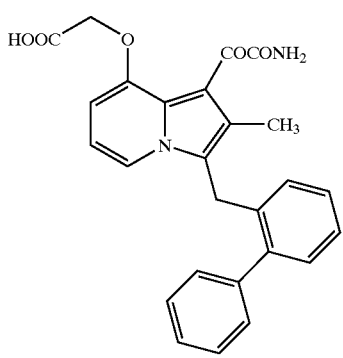
(58j)
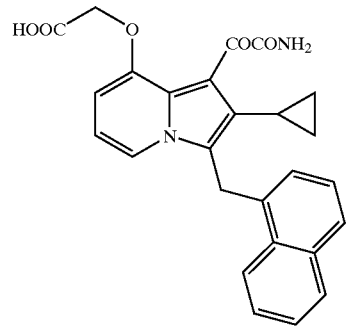
(58f)
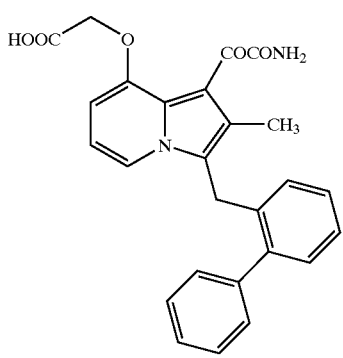
(58k)
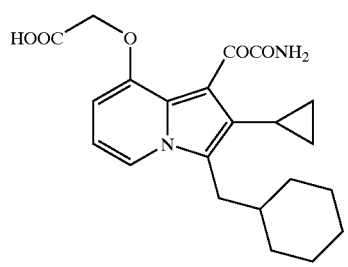

-continued
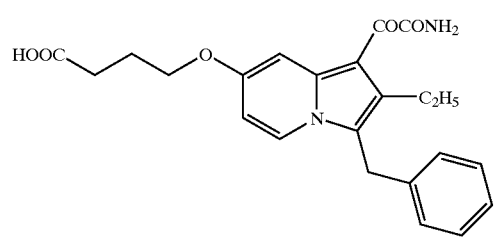
(67a)
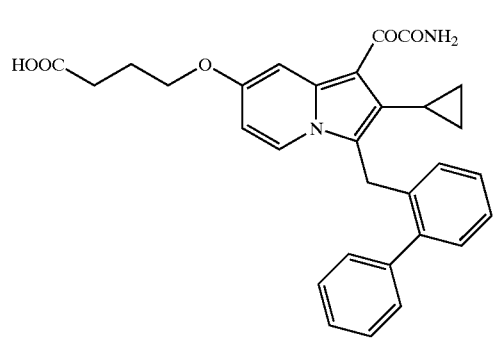
(67b)
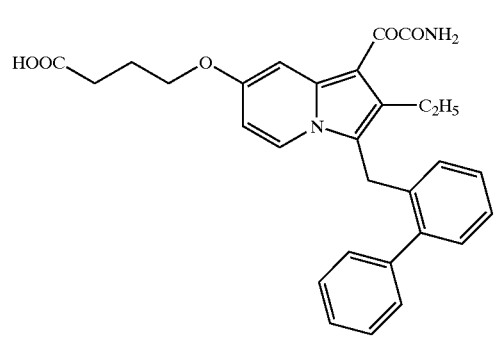
(67c)
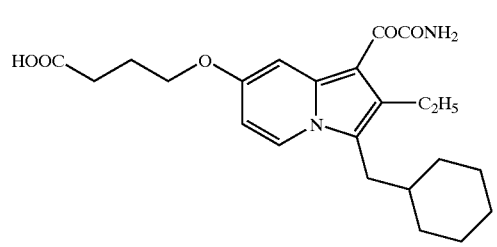
(67d)
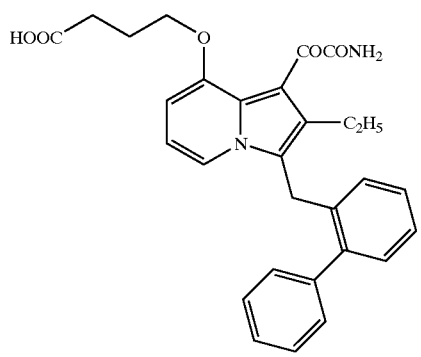
(69a)
-continued
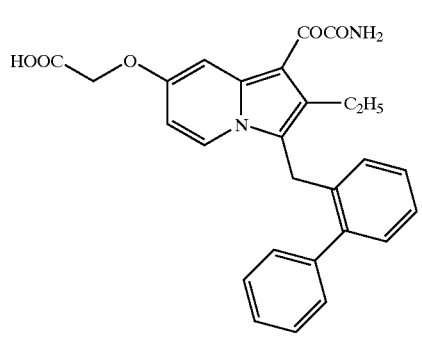
(69b)
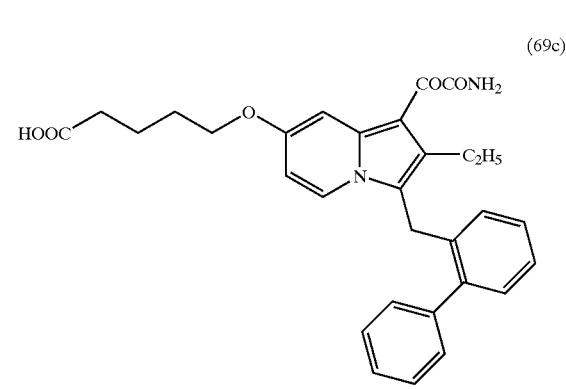
(69c)
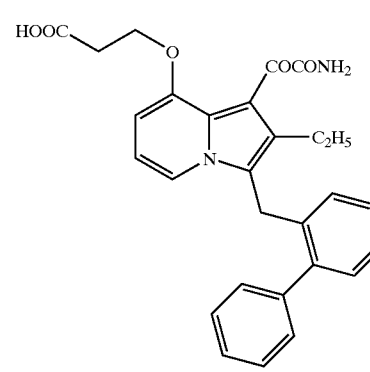
(70a)
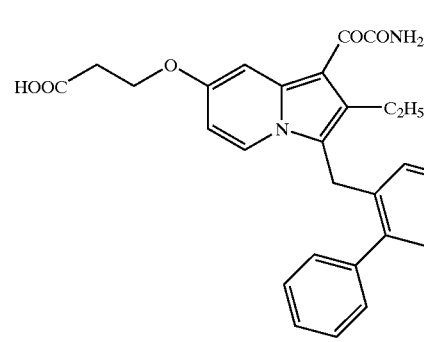
(70b)

-continued

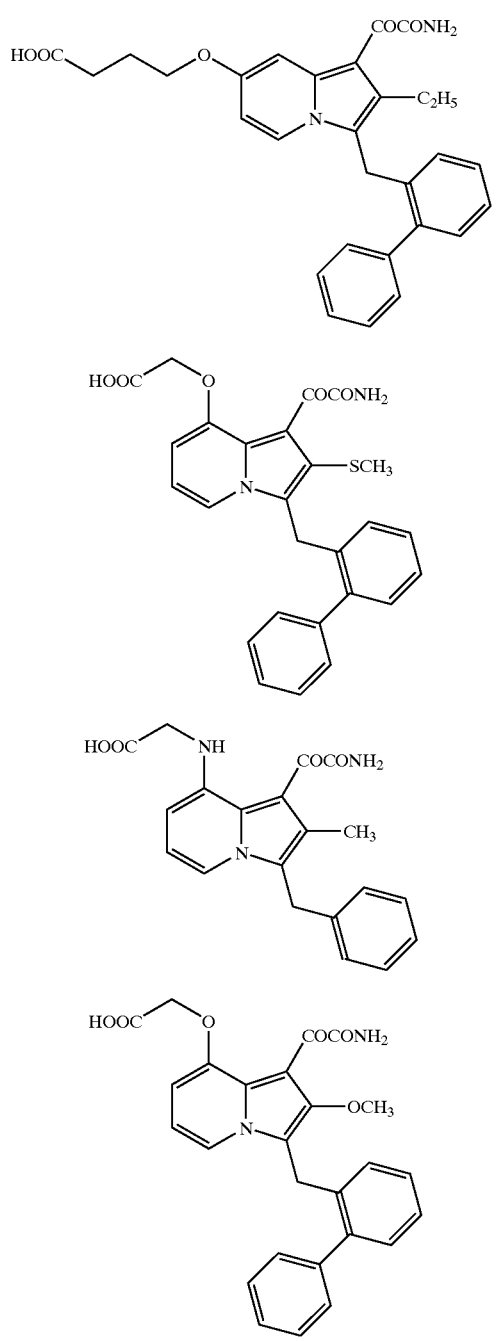

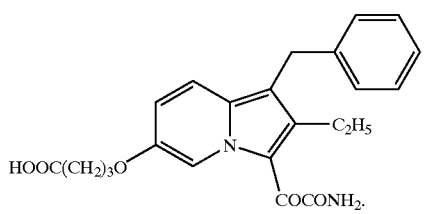

and mixtures of the above compounds.

23. An indolizine-3-acetamide functional compound and a pharmaceutically acceptable salt, solvate or prodrug derivative thereof; wherein said compound is selected from the group represented by the following formulae:

24. A pharmaceutical formulation comprising the indolizine-1-acetamide as claimed in claim 1 together with a pharmaceutically acceptable carrier or diluent therefor.

25. A pharmaceutical formulation comprising the indolizine-1-hydrazide as claimed in claim 4 together with a pharmaceutically acceptable carrier or diluent therefor.

26. A pharmaceutical formulation comprising the indolizine-1-glyoxylamide as claimed in claim 5 together with a pharmaceutically acceptable carrier or diluent therefor.

27. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal of at least one indolizine-1-acetamide as claimed in claim 1 in an amount sufficient to inhibit sPLA$_2$ mediated release of fatty acid and to thereby inhibit or prevent the arachidonic acid cascade and its deleterious products.

28. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal of at least one indolizine-1-hydrazide as claimed in claim 4 in an amount sufficient to inhibit sPLA$_2$ mediated release of fatty acid and to thereby inhibit or prevent the arachidonic acid cascade and its deleterious products.

29. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal of at least one indolizine-1-glyoxylamide as claimed in claim 5 in an amount sufficient to inhibit sPLA$_2$ mediated release of fatty acid and to thereby inhibit or prevent the arachidonic acid cascade and its deleterious products.

30. A method of treating a mammal, including a human, suffering from or susceptible to a disease in which sPLA$_2$ mediated release of fatty acids is a cause which comprises administering an effective amount of a compound according to claim 1.

31. A method of treating a mammal, including a human, suffering from or susceptible to a disease in which sPLA$_2$ mediated release of fatty acids is a cause which comprises administering an effective amount of a compound according to claim 4.

32. A method of treating a mammal, including a human, suffering from or susceptible to a disease in which sPLA$_2$ mediated release of fatty acids is a cause which comprises administering an effective amount of a compound according to claim 5.

* * * * *